United States Patent
Liu et al.

(10) Patent No.: US 11,591,326 B2
(45) Date of Patent: Feb. 28, 2023

(54) INHIBITORS OF PROTEIN ARGININE METHYLTRANSFERASE 5 (PRMT5), PHARMACEUTICAL PRODUCTS THEREOF, AND METHODS THEREOF

(71) Applicant: PHARMABLOCK SCIENCES (NANJING), INC., Jiangsu (CN)

(72) Inventors: Liu Liu, Ann Arbor, MI (US); Jin Li, Jiangsu (CN); Minmin Yang, Jiangsu (CN)

(73) Assignee: Pharmablock Sciences (Nanjing), Inc., Jiangsu (CN)

( * ) Notice: Subject to any disclaimer, the term of this patent is extended or adjusted under 35 U.S.C. 154(b) by 33 days.

(21) Appl. No.: 16/969,652

(22) PCT Filed: Mar. 8, 2019

(86) PCT No.: PCT/US2019/021497
§ 371 (c)(1),
(2) Date: Aug. 13, 2020

(87) PCT Pub. No.: WO2019/173804
PCT Pub. Date: Sep. 12, 2019

(65) Prior Publication Data
US 2020/0399261 A1    Dec. 24, 2020

Related U.S. Application Data

(60) Provisional application No. 62/641,241, filed on Mar. 9, 2018.

(51) Int. Cl.
| | | |
|---|---|---|
| C07D 413/14 | (2006.01) | |
| C07D 401/06 | (2006.01) | |
| C07D 471/04 | (2006.01) | |
| A61P 35/04 | (2006.01) | |
| C07D 401/14 | (2006.01) | |
| C07D 471/08 | (2006.01) | |

(52) U.S. Cl.
CPC ............ *C07D 413/14* (2013.01); *A61P 35/04* (2018.01); *C07D 401/06* (2013.01); *C07D 401/14* (2013.01); *C07D 471/04* (2013.01); *C07D 471/08* (2013.01)

(58) Field of Classification Search
CPC .. C07D 413/14; C07D 401/06; C07D 401/14; C07D 471/04; A61P 35/04
See application file for complete search history.

(56) References Cited

U.S. PATENT DOCUMENTS 9,611,257 B2    4/2017 Duncan et al.
9,777,008 B2    10/2017 Duncan et al.

FOREIGN PATENT DOCUMENTS

WO   WO2014100716   6/2014
WO   WO2014100719   6/2014

OTHER PUBLICATIONS

Lewis, R., ed. Hawleys' Condensed Chemical Dictionary 2007 John Wiley, p. 711.*
PubChem, Compound Summary, 3-[3-(3,4-Dihydro-1H-isoquinolin-2-yl)-2-hydroxypropyl]-8-methylquinazolin-4-one, Pubchem CID: 111149296, Create Date: Jan. 20, 2016.
International Search Report cited in PCT/US19/21497 dated Jul. 10, 2019.
European Search Report issued in Application No./Patent No. 19763499.1 - 1110 /3761978 PCT/U.S. Pat. No. 2019021497, dated Sep. 27, 2021.
Database Registry [Online], Chemical Abstracts Service, Columbus, Ohio, US; Apr. 29, 2012.

* cited by examiner

*Primary Examiner* — Sikarl A Witherspoon
(74) *Attorney, Agent, or Firm* — Workman Nydegger

(57) ABSTRACT

The present invention provides PRMT5 inhibitors of Formula (I), wherein $R_1$ is a non-hydrogen monovalent group; W is a direct bond or —NH—; T, U, and V are independently of each other selected from C and N; $R_2$ is H or a halo; m is 1 or 2; X is a carbon, a nitrogen, or an oxygen; Y is C or N; Z is a direct bond or a carbon; $R_3$ is H, a non-hydrogen monovalent group, an oxo group, a bivalent spiro ring-forming group, or a bivalent bridge-forming group; n is 1 or 2; and Formula (II) stands for a single bond or a double bond. Pharmaceutical products comprising the PRMT5 inhibitors and use thereof in treating proliferative disorders such as cancer, metabolic disorders, blood disorders, autoimmune diseases, and inflammatory diseases are also provided.

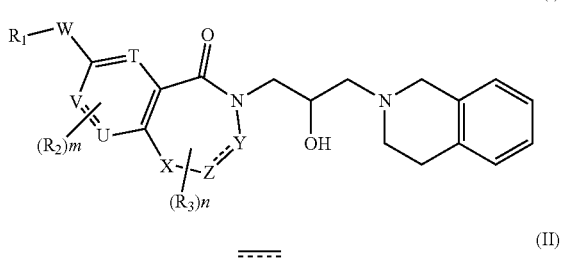

20 Claims, 1 Drawing Sheet

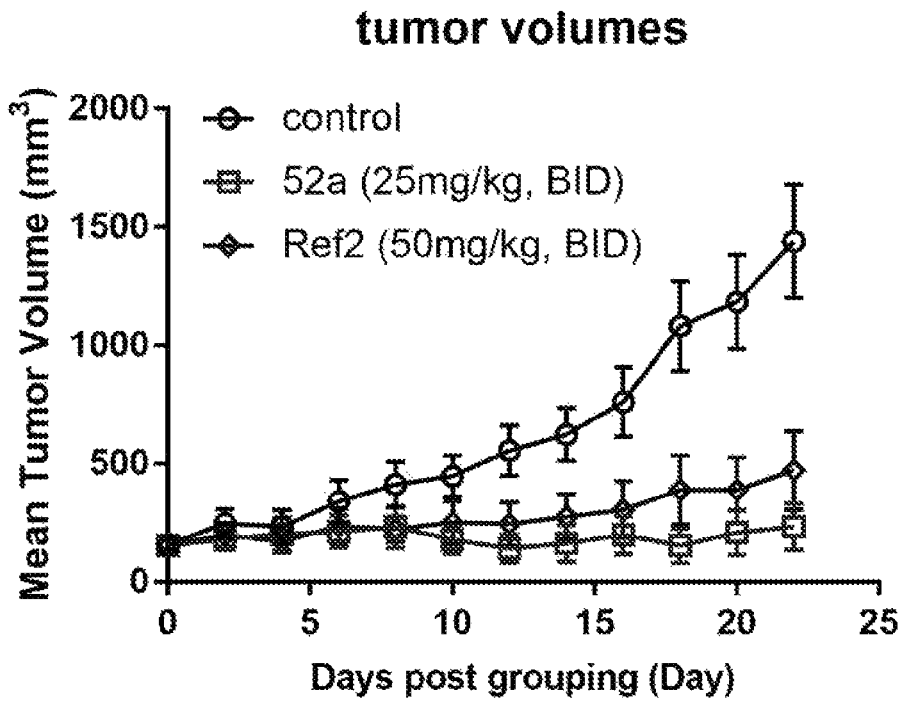
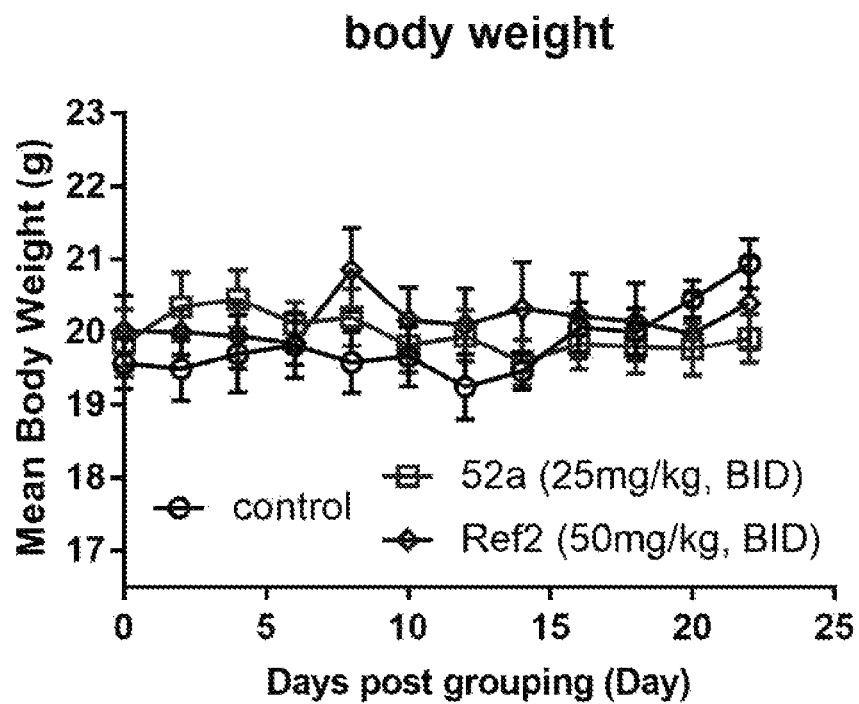

US 11,591,326 B2

INHIBITORS OF PROTEIN ARGININE METHYLTRANSFERASE 5 (PRMT5), PHARMACEUTICAL PRODUCTS THEREOF, AND METHODS THEREOF

CROSS-REFERENCE TO RELATED APPLICATIONS

This is a national stage application filed under 37 U.S.C. 371 based on International Patent Application No. PCT/US2019/021497, filed Mar. 8, 2019, which claims the benefit of U.S. Provisional Application No. 62/641,241, filed Mar. 9, 2018, which are incorporated herein by reference in their entireties.

FIELD OF THE INVENTION

The present invention generally relates to inhibitors of protein arginine methyltransferase 5 (PRMT5), pharmaceutical products thereof, and methods thereof. Although the invention will be illustrated, explained and exemplified by the application of a class of compounds in treating breast cancer, liver cancer, lung cancer, pancreas cancer, brain cancer, and disorders or diseases associated with lymphoma cell, it should be appreciated that the present invention can also include application of the class of compounds and derivatives thereof in treating other disorders or diseases related to PRMT5, for example, prostate cancer, colon cancer, ovarian cancer, skin cancer, testicular cancer, uterine cancer, cervical cancer, esophageal cancer, bladder cancer, gastric cancer, epidermoid cancer, hematopoietic cancer, leukemia such as acute myeloid leukemia (AML), acute lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), hemoglobinopathies such as beta-thalassemia and sickle cell disease (SCD), lymphoma, medulloblastoma, rectum adenocarcinoma, colon adenocarcinoma, adenoid cystic carcinoma, lung adenocarcinoma, head and neck squamous cell carcinoma, hepatocellular carcinoma, renal cell carcinoma, oligodendroglioma, ovarian clear cell carcinoma, ovarian serous cystadenocarcinoma, melanoma, and the like.

BACKGROUND OF THE INVENTION

Epigenetic regulation of gene expression is an important biological determinant of protein production and cellular differentiation, and it plays a significant pathogenic role in a number of human disorders and diseases. Typically, epigenetic regulation involves heritable modification of genetic material without changing its nucleotide sequence, and it is mediated by selective and reversible modification of DNA and proteins (e.g., histones) that control the conformational transition between transcriptionally active and inactive states of chromatin. These covalent modifications can be controlled by enzymes, many of which are associated with specific genetic alterations that can cause human diseases. For example, the methylation of protein arginine is catalyzed by the protein arginine methyl transferases (PRMTs) family of methyltransferases. Such methylation is a common post-translational modification that regulates numerous cellular processes, including gene transcription, mRNA splicing, DNA repair, protein cellular localization, cell fate determination, and signaling. Three types of methyl-arginine species exist: ω NG monomethylarginine (MMA), ω NG, NG asymmetric dimethylarginine (ADMA) and ω NG, N'G symmetric dimethylarginine (SDMA).

There are nine PRMTs annotated in the human genome. The majority of these enzymes are Type I enzymes (PRMT-1, -2, -3, -4, -6, -8) that are capable of mono- and asymmetric dimethylation of arginine, with S-adenosylmethionine (SAM) as the methyl donor. PRMT-5, -7 and -9 are Type II enzymes that catalyze symmetric dimethylation of arginines. Each PRMT species harbors the characteristic motifs of seven beta strand methyltransferases, as well as additional "double E" and "THW" sequence motifs particular to the PRMT subfamily.

PRMT5 is a general transcriptional repressor that functions with numerous transcription factors and repressor complexes, including BRG1 and hBRM, Blimp1, and Snail. This enzyme, once recruited to a promoter, symmetrically dimethylates H3R8 and H4R3. Importantly, the H4R3 site is a major target for PRMT1 methylation (ADMA) and is generally regarded as a transcriptional activating mark. Thus, both H4R3me2s (repressive; me2s indicates SDMA modification) and H4R3me2a (active; me2a indicates ADMA modification) marks are produced in vivo. The specificity of PRMT5 for H3R8 and H4R3 can be altered by its interaction with COPR5 and this could perhaps play an important role in determining PRMT5 corepressor status.

Chromatin-modifying enzymes may play a role in diseases such as proliferative disorders, metabolic disorders, and blood disorders. For example, PRMTs play an important role in cancer. Aberrant expression of PRMTs has been identified in human cancers, and PRMTs are considered to be therapeutic targets. For example, global analysis of histone modifications in prostate cancer has shown that the dimethylation of histone H4R3 is positively correlated with increasing grade, and these changes are predictive of clinical outcome.

PRMT5 levels have been shown to be elevated in a panel of lymphoid cancer cell lines as well as mantle cell lymphoma clinical samples. PRMT5 interacts with a number of substrates that are involved in a variety of cellular processes, including RNA processing, signal transduction, and transcriptional regulation. PRMT5 can directly modify histone H3 and H4, resulting in the repression of gene expression. PRMT5 overexpression can stimulate cell growth and induce transformation by directly repressing tumor suppressor genes. In addition to its oncogenic functions in transcription and translation, the transcription factor MYC also safeguards proper pre-messenger-RNA splicing as an essential step in lymphomagenesis.

The loss of the enzyme methylthioadenosine phosphorylase (MTAP) confers a selective dependence on PRMT5 and its binding partner WDR77. MTAP is frequently lost due to its proximity to the commonly deleted tumor suppressor gene, CDKN2A. Cells harboring MTAP deletions possess increased intracellular concentrations of methylthioadenosine (MTA, the metabolite cleaved by MTAP). Furthermore, MTA specifically inhibits PRMT5 enzymatic activity. Administration of either MTA or a small-molecule PRMT5 inhibitor shows a preferential impairment of cell viability for MTAP-null cancer cell lines compared to isogenic MTAP-expressing counterparts. It has been revealed that PRMT5 has a potential vulnerability across multiple cancer lineages augmented by a common "passenger" genomic alteration.

PRMT5 also plays a role in hemoglobinopathies. The developmental switch in human globin gene subtype from fetal to adult that begins at birth heralds the onset of the hemoglobinopathies, b-thalassemia and sickle cell disease (SCD). The observation that increased adult globin gene expression (in the setting of hereditary persistence of fetal hemoglobin [HPFH] mutations) significantly ameliorates the clinical severity of thalassemia and SCD has prompted the search for therapeutic strategies to reverse gamma-globin gene silencing. Central to silencing of the gamma-genes is DNA methylation, which marks critical CpG dinucleotides flanking the gene transcriptional start site in adult bone marrow erythroid cells. It has been shown that these marks are established as a consequence of recruitment of the DNA methyltransferase, DNMT3A to the gamma-promoter by PRMT5. PRMT5-mediated methylation of histone H4R3 recruits DNMT3A, coupling histone and DNA methylation in gene silencing. PRMT5 induces the repressive histone mark, H4R3me2s, which serves as a template for direct binding of DNMT3A, and subsequent DNA methylation. Loss of PRMT5 binding or its enzymatic activity leads to demethylation of the CpG dinucleotides and gene activation. In addition to the H4R3me2s mark and DNA methylation, PRMT5 binding to the gamma-promoter, and its enzymatic activity are essential for assembly of a multiprotein complex on the gamma-promoter, which induces a range of coordinated repressive epigenetic marks. Disruption of this complex leads to reactivation of gamma gene expression. These observations provide the basis for developing PRMT5 inhibitors as targeted therapies for thalassemia and SCD.

Therefore, there exists a need for the development of small molecules that are capable of inhibiting the activity of PRMT5, and treating various PRMT5-related disorders and diseases.

SUMMARY OF THE INVENTION

One aspect of the present invention provides a compound represented by Formula (I), or a pharmaceutically acceptable salt, ester, prodrug, complex, solvate, isomer, or hydrate thereof, in any crystalline form or in amorphous form. In Formula (I), $R_1$ may be any suitable non-hydrogen monovalent group; W may be a direct bond or —NH—; T, U, and V are independently of each other selected from carbon and nitrogen; $R_2$ is a hydrogen or a halo; m is 1 or 2; X is a carbon, a nitrogen, or an oxygen; Y is a carbon or a nitrogen; Z is a direct bond or a carbon; $R_3$ is a hydrogen, a non-hydrogen monovalent group, an oxo group or carbonyl group (O=), a bivalent spiro ring-forming group, or a bivalent bridge-forming group; n is 1 or 2; and ===== stands for a single bond or a double bond.

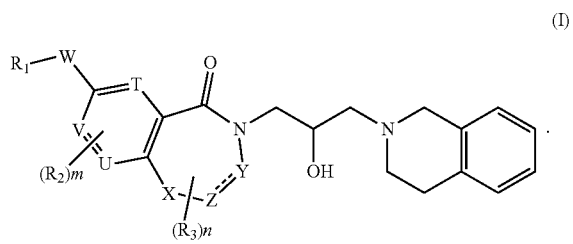

(I)

Another aspect of the invention provides a pharmaceutical composition comprising a compound of Formula (I), or a pharmaceutically acceptable salt, ester, prodrug, complex, solvate, hydrate, or isomer thereof, in any crystalline form or in amorphous form; and a pharmaceutically acceptable excipient.

Still another aspect of the invention provides a kit or packaged pharmaceutical comprising a compound of Formula (I), or a pharmaceutically acceptable salt, ester, prodrug, complex, solvate, hydrate or isomer thereof, in any crystalline form or in amorphous form; and instructions for use thereof.

Still another aspect of the invention provides a method of inhibiting PRMT5 enzyme, comprising: contacting the PRMT5 enzyme with an effective amount of a compound of Formula (I), or a pharmaceutically acceptable salt, ester, prodrug, complex, solvate, hydrate or isomer thereof, in any crystalline form or in amorphous form.

A further aspect of the invention provides a method of altering gene expression or altering transcription comprising contacting a cell in vitro or in a subject with an effective amount of a compound of Formula (I), or a pharmaceutically acceptable salt, ester, prodrug, complex, solvate, hydrate or isomer thereof, in any crystalline form or in amorphous form.

Another aspect of the invention provides a method of a method of treating a disorder or disease mediated by PRMT5 or associated with aberrant PRMT5 activity, comprising administering to a subject in need thereof a therapeutically effective amount of a compound of Formula (I), or a pharmaceutically acceptable salt, ester, prodrug, complex, solvate, hydrate or isomer thereof, in any crystalline form or in amorphous form; or a pharmaceutical composition thereof. The disorder or disease may be a proliferative disorder such as cancer, a metabolic disorder such as diabetes or obesity, or a blood disorder such as hemoglobinopathy, e.g. sickle cell anemia or beta-thalassemia.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements.

FIG. 1 shows the tumor volume change after the treatment in mantle cell lymphoma (MCL) Z-138 xenograft efficacy studies using a compound of formula (I) in accordance with an exemplary embodiment of the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

The present invention provides a compound of Formula (I), or a pharmaceutically acceptable salt, ester, prodrug, complex, solvate, or hydrate thereof.

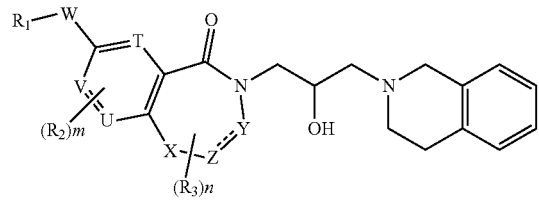

In Formula (I), $R_3$ may be an oxo or carbonyl group O=, a bivalent spiro ring-forming group, or a bivalent bridge-forming group, among others. For example, $R_3$ may be a methyl group and an oxo group (n=2) in an exemplary compound of the invention, i.e. 4-(3-(3,4-dihydroisoquinolin-2(1H)-yl)-2-hydroxypropyl)-1-methyl-7-(pyridazin-4-ylamino)-3,4-dihydro-1H-benzo[e][1,4]diazepine-2,5-dione (44):

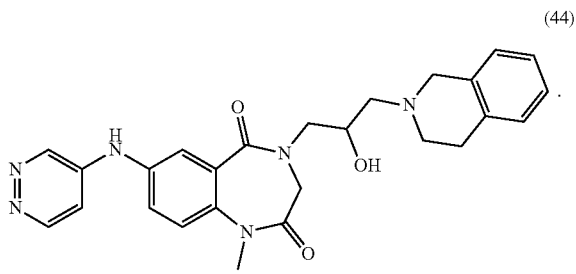 [SMILES: CN1C(=O)CN(CC(O)CN2CCc3ccccc3C2)C(=O)c2cc(Nc3ccnnc3)ccc21]

A bivalent spiro ring-forming group is defined as a group comprising two atoms (two valents) which can be bonded to a same ring member atom. For example, $R_3$ is a bivalent spiro ring-forming group such as an ethylene spiro ring-forming group —CH$_2$CH$_2$—, in which two carbon atoms each can be bonded to a same ring member atom such as C. For the purpose of illustration, two specific compounds of the invention include such an ethylene spiro ring-forming group —CH$_2$CH$_2$—, i.e. 2'-(3-(3,4-dihydroisoquinolin-2(1H)-yl)-2-hydroxypropyl)-7'-(pyridazin-4-ylamino)-2',3'-dihydro-1'H-spiro[cyclopropane-1,4'-isoquinolin]-1'-one (35); and 7'-((1-acetyl piperidin-4-yl)amino)-2'-(3-(3,4-dihydroisoquinolin-2(1H)-yl)-2-hydroxypropyl)-2',3'-dihydro-1'H-spiro[cyclopropane-1,4'-isoquinolin]-1'-one (53):

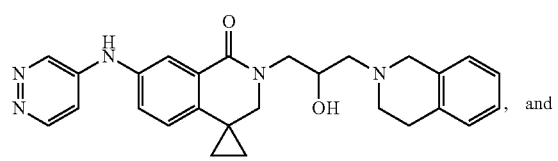

, and

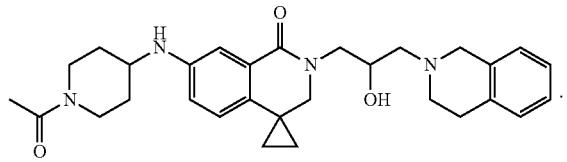

A bivalent bridge-forming group is defined as a group that can be bonded to two ring member atoms. The two ring member atoms may be adjacent to each other (fused), or not adjacent to each other in the ring (bridged). For example, $R_3$ is a bivalent bridge-forming group such as a methylene bridge-forming group —CH$_2$— that can be bonded or attached to two ring-member atoms such as two carbon atoms in a compound of the invention, e.g. 8-((1-acetyl piperidin-4-yl)amino)-2-(3-(3,4-dihydroisoquinolin-2(1H)-yl)-2-hydroxypropyl)-2,3,4,5-tetrahydro-1H-3,5-methano-benzo[c]azepin-1-one (57), in which "3,5-methano" indicates that the bivalent bridge-forming group —CH$_2$— bridges between C atom at position 3 and C atom at position 5:

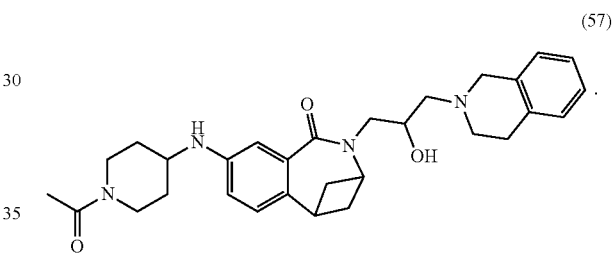

In Formula (I), $R_1$ or $R_3$ may be selected from any suitable non-hydrogen monovalent groups. The term "non-hydrogen monovalent group", as used herein, may include, but is not limited to, groups in the following 8 classes.

Class (1): Halo or halogen group, i.e. —F, —Cl, —Br or —I; —CN, —NO$_2$, —N$_3$, —SO$_2$H, —SO$_3$H, —OH, —OR, —ONR$_2$, —NR$_2$, —NR$_3$$^+$X$^-$, —N(OR)R, —SH, —SR, —SSR, —C(=O)R, —CO$_2$H, —CHO, —C(OR)$_2$, —CO$_2$R, —OC(=O)R, —OCO$_2$R, —C(=O)NR$_2$, —OC(=O)NR$_2$, —NRC(=O)R, —NRCO$_2$R, —NRC(=O)NR$_2$, —C(=NR)R, —C(=NR)OR, —OC(=NR)R, —OC(=NR)OR, —C(=NR)NR$_2$, —OC(=NR)NR$_2$, —NRC(=NR)NR$_2$, —C(=O)NRSO$_2$R, —NRSO$_2$R, —SO$_2$NR$_2$, —SO$_2$R, —SO$_2$OR, —OSO$_2$R, —S(=O)R, —OS(=O)R, —SiR$_3$, —OSiR$_3$, —C(=S)NR$_2$, —C(=O)SR, —C(=S)SR, —SC(=S)SR, —SC(=O)SR, —OC(=O)SR, —SC(=O)OR, —SC(=O)R, —P(=O)$_2$R, —OP(=O)$_2$R, —P(=O)R$_2$, —OP(=O)R$_2$, —OP(=O)(OR)$_2$, —P(=O)NR$_2$, —OP(=O)$_2$NR$_2$, —P(=O)(NR)$_2$, —OP(=O)(NR)$_2$, —NRP(=O)(OR)$_2$, —NRP(=O)(NR)$_2$, —PR$_2$, —PR$_3$, —OPR$_2$, —OPR$_3$, —BR$_2$, —B(OR)$_2$, —BR(OR), and the like. R is independently of each other any suitable group e.g. alkyl group. For example, —OR may be an alkoxy or alkyloxy group, i.e. an —O-alkyl group. The term $C_{1-6}$ alkoxy/alkyloxy is an —O—($C_{1-6}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

Class (2): Alkyl group, i.e. saturated aliphatic hydrocarbon including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_{1-6}$ alkyl" refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). An alkyl group optionally can be substituted by one or more (e.g., 1 to 5) suitable substituents.

Class (3): Alkenyl group, i.e. aliphatic hydrocarbon having at least one carbon-carbon double bond, including straight chains and branched chains having at least one carbon-carbon double bond. In some embodiments, the alkenyl group has 2 to 20 carbon atoms, 2 to 10 carbon atoms, 2 to 6 carbon atoms, 3 to 6 carbon atoms, or 2 to 4 carbon atoms. For example, the term "$C_{2-6}$ alkenyl" includes straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. The alkenyl group may exist as the pure E form, the pure Z form, or any mixture thereof.

Class (4): Alkynyl group, i.e. aliphatic hydrocarbons having at least one carbon-carbon triple bond, including straight chains and branched chains having at least one carbon-carbon triple bond. In some embodiments, the alkynyl group has 2 to 20, 2 to 10, 2 to 6, or 3 to 6 carbon atoms. For example, "$C_{2-6}$ alkynyl" includes straight or branched hydrocarbon chain alkynyl radicals as defined above, having 2 to 6 carbon atoms. An alkynyl group optionally can be substituted by one or more (e.g., 1 to 5) suitable substituents.

Class (5): Cycloalkyl group may be saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.). The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, "$C_{3-14}$ cycloalkyl" includes saturated or unsaturated, non-aromatic, monocyclic or polycyclic (such as bicyclic) hydrocarbon rings of 3 to 14 ring-forming carbon atoms (e.g., cyclopropyl, cyclobutyl, cyclopentyl, cyclohexyl, bicyclo[1.1.1]pentanyl, or cyclodecanyl). The cycloalkyl group optionally can be substituted by 1 or more (e.g., 1 to 5) suitable substituents.

Class (6): Aryl group, i.e. all-carbon monocyclic or fused-ring polycyclic aromatic groups having a conjugated pi-electron system. The aryl group may have 6 or 10 carbon atoms in the ring(s). Most commonly, the aryl group has 6 carbon atoms in the ring. For example, $C_{6-10}$ aryl is an aromatic radical containing from 6 to 10 carbon atoms such as phenyl or naphthyl. The aryl group optionally can be substituted by 1 or more (e.g., 1 to 5) suitable substituents.

Class (7): Heteroaryl group, i.e. monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono (i.e., =S) groups. In some embodiments, the heteroaryl group has 5 to 8 ring-forming atoms including one, two or three heteroatoms. For example, 5-membered heteroaryl group is a monocyclic heteroaryl group as defined above with 5 ring-forming atoms in the monocyclic heteroaryl ring; 6-membered heteroaryl is a monocyclic heteroaryl group as defined above with 6 ring-forming atoms in the monocyclic heteroaryl ring; 5~40-membered heteroaryl is a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms. Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like.

Class (8): Heterocycloalkyl group, i.e. monocyclic or polycyclic (including 2 or more rings that are fused together, including Spiro, fused, or bridged systems, for example, a bicyclic ring system), saturated or unsaturated, non-aromatic 4- to 15-membered ring system including 1 to 14 ring-forming carbon atoms and 1 to 10 ring-forming heteroatoms each independently selected from O, S, N, P and B. The heterocycloalkyl group can also optionally contain one or more oxo (i.e., =O) or thiono (i.e., =S) groups. For example, 4- to 12-membered heterocycloalkyl is a monocyclic or polycyclic, saturated or unsaturated, non-aromatic 4- to 12-membered ring system that comprises one or more ring-forming heteroatoms. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g., 2-oxaspiro[3.3]hept-6-yl}, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g., tetrahydro-2H-pyran-4-yl), imidazolidin-1-yl, imidazolidin-2-yl, imidazolidin-4-yl, pyrrolidin-1- yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

The term "non-hydrogen monovalent group" may include a combination of any number of groups selected from the above 8 classes. By a combination of two groups, it means that one group (G1) is substituted with another group (G2) to form a new group -G1-G2. By combination of three groups, it means that a first group (G1) is substituted with a second group (G2) which is substituted with a third group (G3), forming a new group -G1-G2-G3. For example, a group from Classes (2)-(8) may be substituted with a group from Class (1): (i) Haloalkyl group such as fluoroalkyl, i.e. an alkyl group having one or more halogen substituents such as F (up to perhaloalkyl, i.e., every hydrogen atom of the alkyl group has been replaced by a halogen atom). For example, C1-6 haloalkyl is a C1-6 alkyl group having one or more halogen substituents (up to perhaloalkyl, i.e., every hydrogen atom of the alkyl group has been replaced by a halogen atom). C1 haloalkyl is a methyl group having one, two, or three halogen substituents. (ii) Hydroxylalkyl or hydroxyalkyl, i.e. an alkyl group having one or more (e.g., 1, 2, or 3) OH substituents. (iii) Cyanoalkyl group, i.e an alkyl group having one or more (e.g., 1, 2, or 3) —CN substituents. A group from Class (1) may be substituted with another group from Class (1), e.g. haloalkoxy group such as fluoroalkoxy, i.e. an —O-haloalkyl group. C1-6 haloalkoxy refers to an —O—(C1-6 haloalkyl) group.

The term "non-hydrogen monovalent group" may also be any group selected from the above 8 classes and combination of any number of groups selected from the above 8 classes, that are substituted with one or more bivalent groups, i.e. two germinal hydrogens on a same atom are replaced with a group such as =O, =S, =NNR$_2$, =NNRC(=O)R, =NNRC(=O)OR, =NNRS(=O)$_2$R, =NR, =NOR, or the like.

In preferred embodiments, Formula (I) is Formula (Ia-1) or Formula (Id-1):

Ia-1

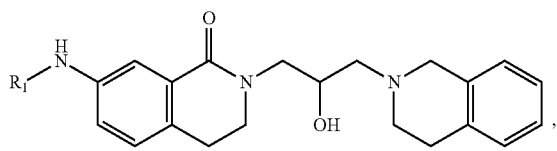

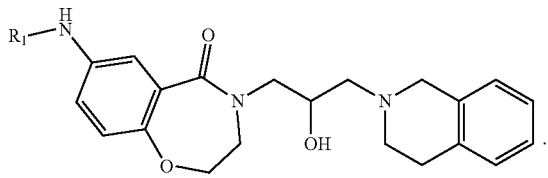

Id-1

In specific embodiments of the invention, R$_1$ in Formula (I), (Ia-1) and (Id-1) may be piperidinyl, acetylpiperidinyl, a C$_3$-C$_{12}$ Spiro-, fused-, or bridged-bicyclic group containing 0-2 hetero atoms, azaspiroheptanyl, acetylazaspiroheptanyl, azetidinyl, acetylazetidinyl, (methylsulfonyl)azetidinyl, azabicyclooctanyl, acetylazabicyclooctanyl, azabicyclohexanyl, acetylazabicyclohexanyl, cycloalkyl, pyrrolidinyl, oxopyrrolidinyl, alkyloxopyrrolidinyl, methyloxopyrrolidinyl, methylazetidinyl, pyrazolyl, alkylpyrazolyl, alkyl-1H-pyrazolyl, methyl-oxo-dihydropyridinyl, methyl-oxadiazolyl, oxetanyl, (oxetanyl)-1H-pyrazolyl, pyrimidinyl, pyridazinyl, tetrahydrofuranyl, tetrahydropyranyl, or tetrahydropyranyl-pyrazolyl.

Generally, the point of attachment of the non-hydrogen monovalent group can be from any suitable position. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl). The point of attachment of the non-hydrogen monovalent group can be specified to indicate the position where the non-hydrogen monovalent group is attached to another moiety. For example, "—C$_{1-2}$ alkyl-(C$_{3-4}$ cycloalkyl)" means the point of attachment occurs at the "C$_{1-2}$ alkyl" part. For another example, "(C$_{3-4}$ cycloalkyl)-C$_{1-2}$ alkyl-" also means the point of attachment occurs at the "C$_{1-2}$ alkyl" part. When a bond to a substituent is shown to cross a bond connecting two atoms in a ring, then such substituent may be bonded to any of the ring-forming atoms in that ring that are substitutable (i.e., one or more hydrogen atoms), unless otherwise specified or otherwise implicit from the context.

In specific embodiments of the invention, R$_1$ in Formula (I), (Ia-1) and (Id-1) may be 1-acetylpiperidin-4-yl, 2-acetyl-2-azaspiro[3.3]heptan-6-yl, 1-acetylazetidin-3-yl, 8-acetyl-8-azabicyclo[3.2.1]octan-3-yl, 3-acetyl-3-azabicyclo[3.1.0]hexan-6-yl, cyclobutyl, 1-methyl-5-oxopyrrolidin-3-yl, 1-(methylsulfonyl)azetidin-3-yl, 1-methylazetidin-3-yl, 1-methyl-1H-pyrazol-4-yl, 1-methyl-1H-pyrazol-3-yl, 1-methyl-1H-pyrazol-5-yl, 1-methyl-2-oxo-1,2-dihydropyridin-4-yl, 5-methyl-1,3,4-oxadiazol-2-yl, oxetan-3-yl, 1-(oxetan-3-yl)-1H-pyrazol-4-yl, pyrimidin-5-yl, pyrimidin-4-yl, pyridazin-4-yl, pyridazin-3-yl, pyrazin-2-yl, tetrahydrofuran-3-yl, tetrahydro-2H-pyran-4-yl, or 1-(tetrahydro-2H-pyran-4-yl)-1H-pyrazol-4-yl.

In exemplary embodiments, R$_2$ in Formula (I) is H or F, and m=1.

In other exemplary embodiments, R$_3$ in Formula (I) is H, a C1-C6 alkyl such as methyl, an oxo group or carbonyl (O=), a bivalent C2-C6 spiro ring-forming group such as an ethylene spiro ring-forming group, or a bivalent C1-C4 bridge-forming group such as a methylene bridge-forming group; and n=1 or 2.

Table 1A lists some representative examples of Formula (I) compound and their codes used through the present description. These compounds can effectively inhibit the enzymatic activity of PRMT5, as will be described in more details in the EXAMPLE section.

TABLE 1A

| # | Structure |
|---|---|
| 1 | 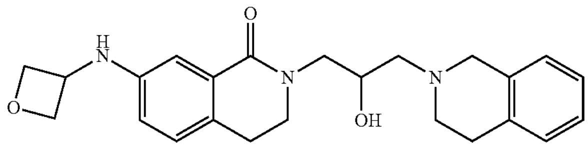 [SMILES: O=C1c2cc(NC3COC3)ccc2CCN1CC(O)CN1CCc2ccccc2C1] |
| 2a | 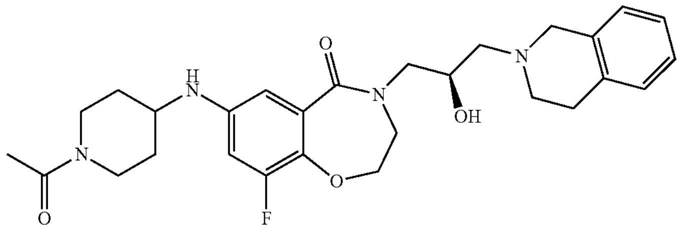 [SMILES: CC(=O)N1CCC(Nc2cc(F)c3c(c2)C(=O)N(C[C@H](O)CN2CCc4ccccc4C2)CCO3)CC1] |
| 2b | 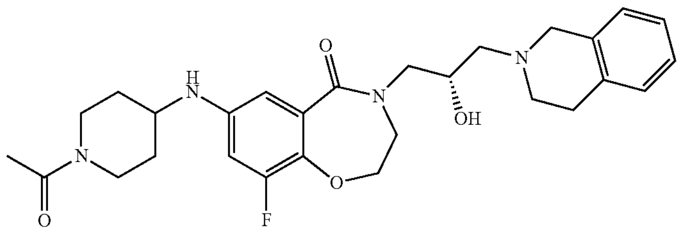 [SMILES: CC(=O)N1CCC(Nc2cc(F)c3c(c2)C(=O)N(C[C@@H](O)CN2CCc4ccccc4C2)CCO3)CC1] |
| 3 | 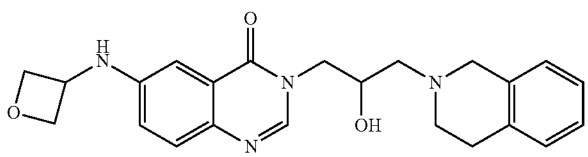 [SMILES: O=c1c2cc(NC3COC3)ccc2ncn1CC(O)CN1CCc2ccccc2C1] |
| 4 | 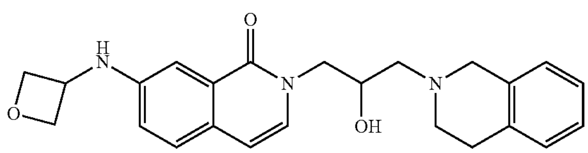 [SMILES: O=c1c2cc(NC3COC3)ccc2ccn1CC(O)CN1CCc2ccccc2C1] |
| 5 | 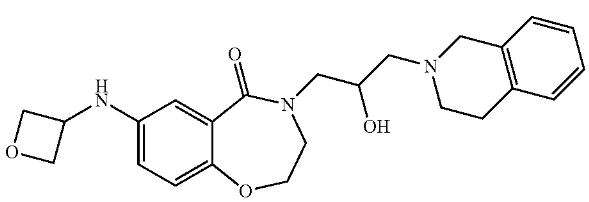 [SMILES: O=C1c2cc(NC3COC3)ccc2OCCN1CC(O)CN1CCc2ccccc2C1] |
| 6 | 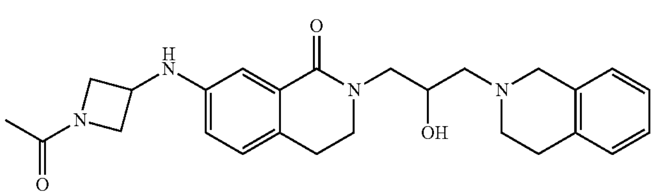 [SMILES: CC(=O)N1CC(Nc2ccc3c(c2)C(=O)N(CC(O)CN2CCc4ccccc4C2)CC3)C1] |
| 7 | 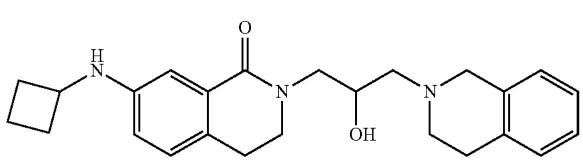 [SMILES: O=C1c2cc(NC3CCC3)ccc2CCN1CC(O)CN1CCc2ccccc2C1] |

TABLE 1A-continued

| # | Structure |
|---|---|
| 8 | 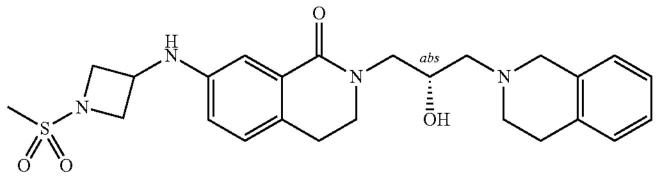 [SMILES: CS(=O)(=O)N1CC(Nc2ccc3c(c2)C(=O)N(C[C@@H](O)CN2CCc4ccccc4C2)CC3)C1] |
| 9 | 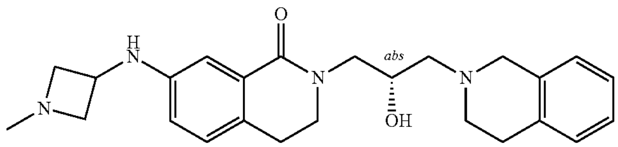 [SMILES: CN1CC(Nc2ccc3c(c2)C(=O)N(C[C@@H](O)CN2CCc4ccccc4C2)CC3)C1] |
| 10 | 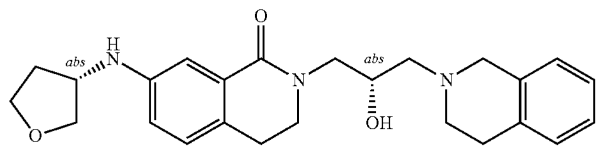 [SMILES: O=C1c2cc(N[C@H]3CCOC3)ccc2CCN1C[C@@H](O)CN1CCc2ccccc2C1] |
| 11 | 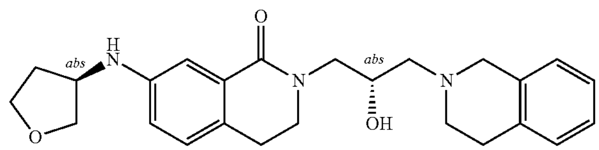 [SMILES: O=C1c2cc(N[C@@H]3CCOC3)ccc2CCN1C[C@@H](O)CN1CCc2ccccc2C1] |
| 12 | 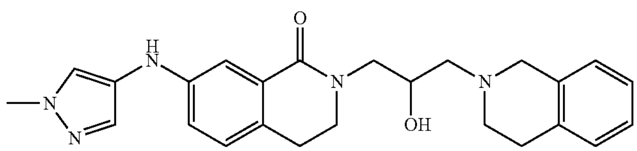 [SMILES: Cn1cc(Nc2ccc3c(c2)C(=O)N(CC(O)CN2CCc4ccccc4C2)CC3)cn1] |
| 12a | 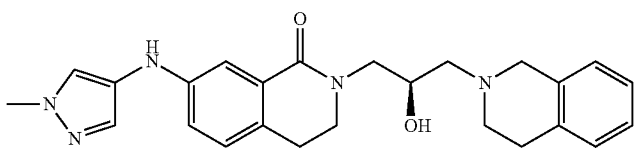 [SMILES: Cn1cc(Nc2ccc3c(c2)C(=O)N(C[C@H](O)CN2CCc4ccccc4C2)CC3)cn1] |
| 12b | 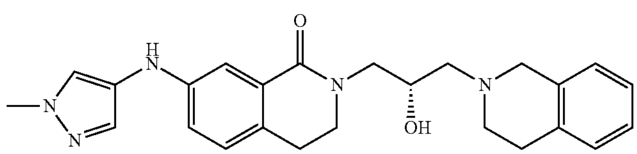 [SMILES: Cn1cc(Nc2ccc3c(c2)C(=O)N(C[C@@H](O)CN2CCc4ccccc4C2)CC3)cn1] |
| 13 | 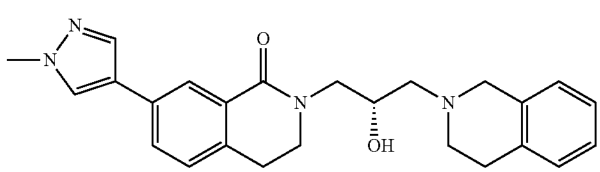 [SMILES: Cn1cc(-c2ccc3c(c2)C(=O)N(C[C@@H](O)CN2CCc4ccccc4C2)CC3)cn1] |
| 14 | 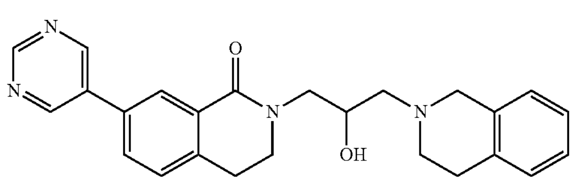 [SMILES: O=C1c2cc(-c3cncnc3)ccc2CCN1CC(O)CN1CCc2ccccc2C1] |

TABLE 1A-continued

| # | Structure |
|---|---|
| 15 | 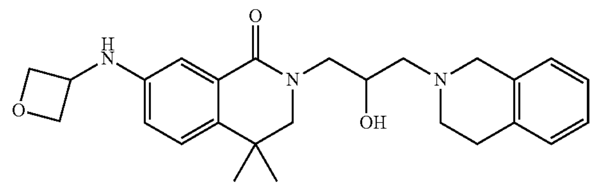 [SMILES: CC1(C)CN(CC(O)CN2CCc3ccccc3C2)C(=O)c2cc(NC3COC3)ccc21] |
| 16 | 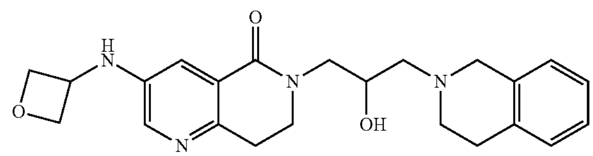 [SMILES: O=C1c2cc(NC3COC3)cnc2CCN1CC(O)CN1CCc2ccccc2C1] |
| 17a | 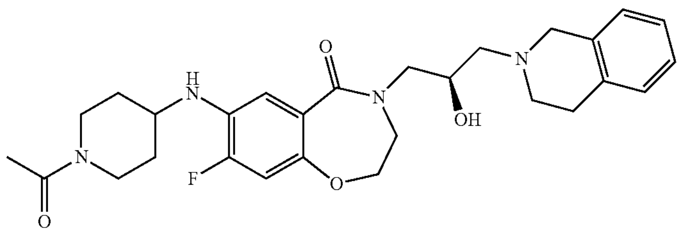 [SMILES: CC(=O)N1CCC(Nc2cc3c(cc2F)OCCN(C[C@H](O)CN2CCc4ccccc4C2)C3=O)CC1] |
| 17b | 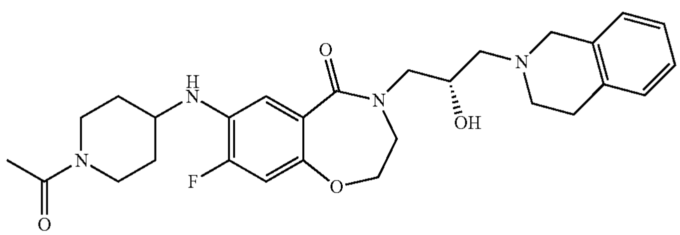 [SMILES: CC(=O)N1CCC(Nc2cc3c(cc2F)OCCN(C[C@@H](O)CN2CCc4ccccc4C2)C3=O)CC1] |
| 18 | 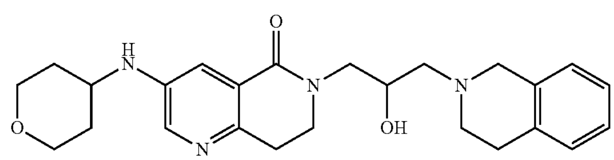 [SMILES: O=C1c2cc(NC3CCOCC3)cnc2CCN1CC(O)CN1CCc2ccccc2C1] |
| 19 | 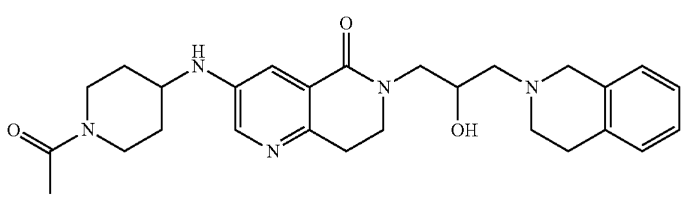 [SMILES: CC(=O)N1CCC(Nc2cnc3c(c2)C(=O)N(CC(O)CN2CCc4ccccc4C2)CC3)CC1] |
| 20 | 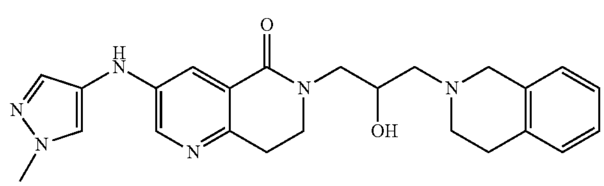 [SMILES: Cn1cc(Nc2cnc3c(c2)C(=O)N(CC(O)CN2CCc4ccccc4C2)CC3)cn1] |
| 21 | 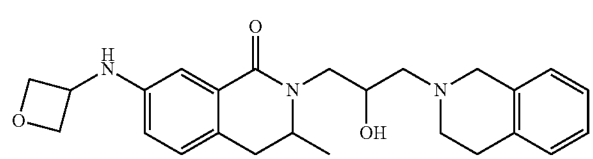 [SMILES: CC1Cc2ccc(NC3COC3)cc2C(=O)N1CC(O)CN1CCc2ccccc2C1] |

TABLE 1A-continued

| # | Structure |
|---|---|
| 22 | (chemical structure) |
| 23 | (chemical structure) |
| 24 | (chemical structure) |
| 24a | (chemical structure) |
| 24b | (chemical structure) |
| 25 | (chemical structure) |
| 26 | (chemical structure) |

TABLE 1A-continued
| # | Structure |
|---|---|
| 27 | 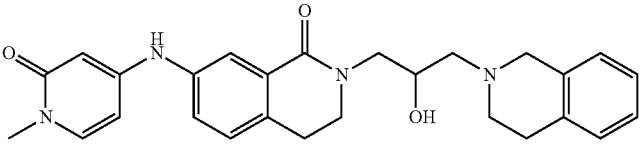 [SMILES: Cn1ccc(Nc2ccc3c(c2)C(=O)N(CC(O)CN2CCc4ccccc4C2)CC3)cc1=O] |
| 28 | 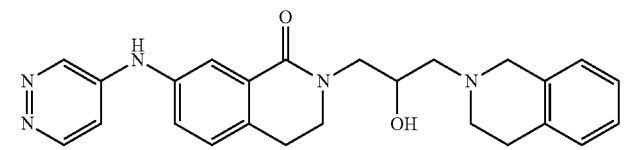 [SMILES: O=C1c2cc(Nc3ccnnc3)ccc2CCN1CC(O)CN1CCc2ccccc2C1] |
| 28a | 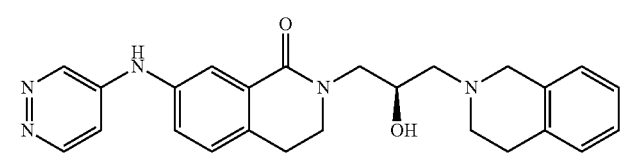 [SMILES: O=C1c2cc(Nc3ccnnc3)ccc2CCN1C[C@H](O)CN1CCc2ccccc2C1] |
| 28b | 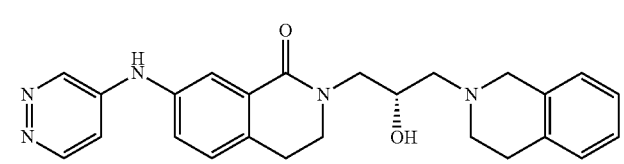 [SMILES: O=C1c2cc(Nc3ccnnc3)ccc2CCN1C[C@@H](O)CN1CCc2ccccc2C1] |
| 29 | 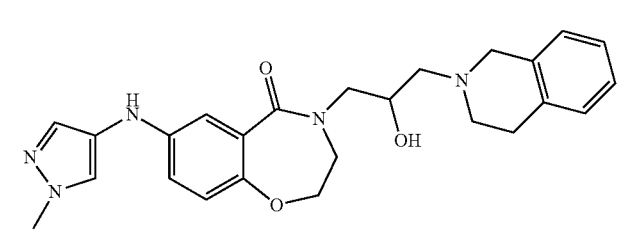 [SMILES: Cn1cc(Nc2ccc3c(c2)C(=O)N(CC(O)CN2CCc4ccccc4C2)CCO3)cn1] |
| 29a | 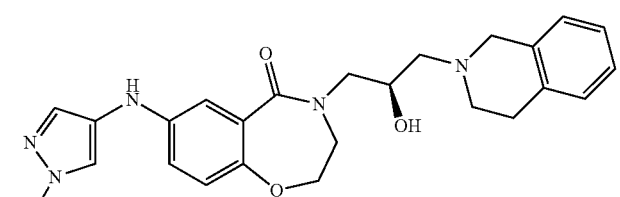 |
| 29b | 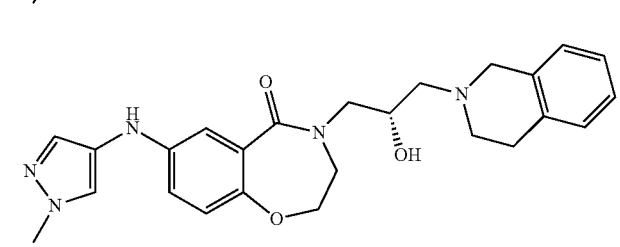 |
| 30 | 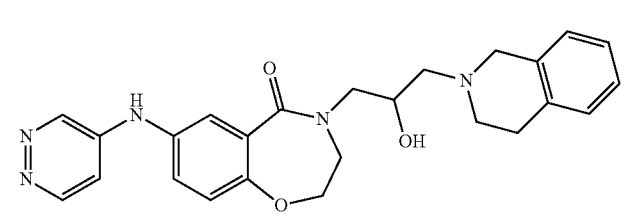 [SMILES: O=C1c2cc(Nc3ccnnc3)ccc2OCCN1CC(O)CN1CCc2ccccc2C1] |

TABLE 1A-continued
| # | Structure |
|---|---|
| 30a | 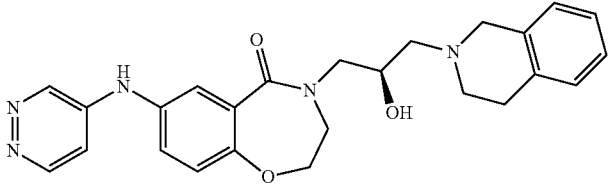 [SMILES: O=C1c2cc(Nc3ccnnc3)ccc2OCCN1C[C@H](O)CN1CCc2ccccc2C1] |
| 30b | 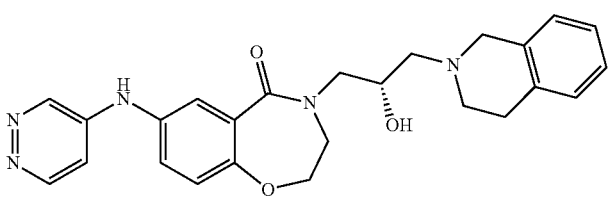 [SMILES: O=C1c2cc(Nc3ccnnc3)ccc2OCCN1C[C@@H](O)CN1CCc2ccccc2C1] |
| 31 | 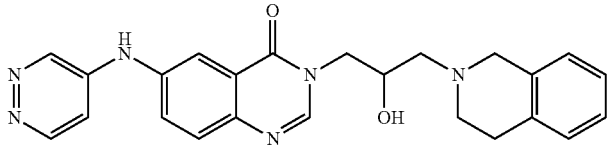 [SMILES: O=c1c2cc(Nc3ccnnc3)ccc2ncn1CC(O)CN1CCc2ccccc2C1] |
| 32 | 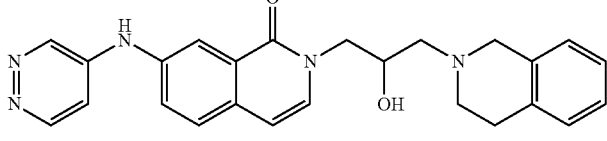 |
| 33 | 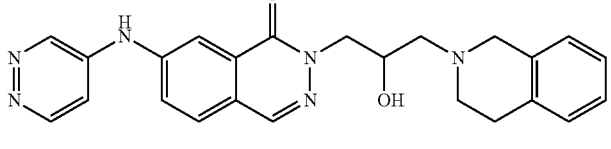 |
| 34 | 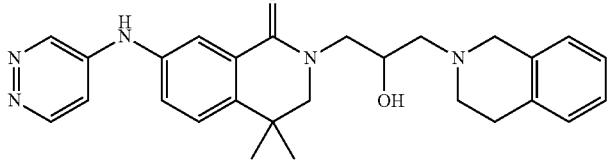 |
| 35 | 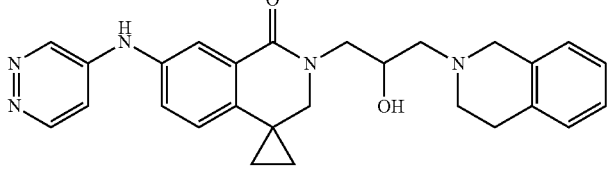 |
| 36 | 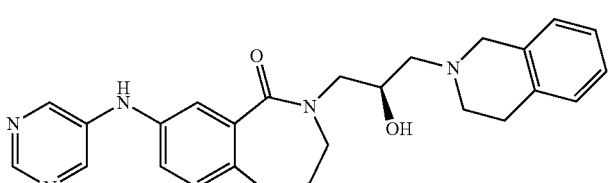 |

TABLE 1A-continued
| # | Structure |
|---|---|
| 37 | 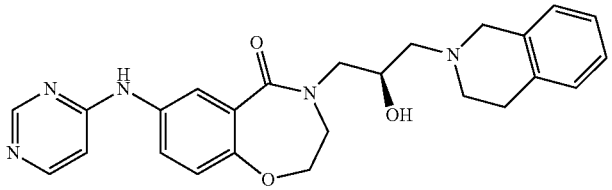 [SMILES: O=C1c2cc(Nc3ccncn3)ccc2OCCN1C[C@H](O)CN1CCc2ccccc2C1] |
| 38 | 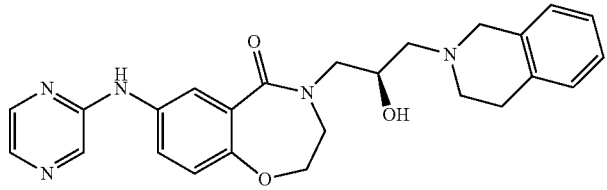 [SMILES: O=C1c2cc(Nc3cnccn3)ccc2OCCN1C[C@H](O)CN1CCc2ccccc2C1] |
| 39 | 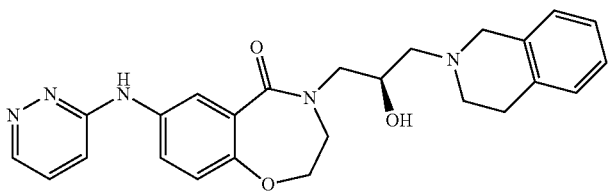 [SMILES: O=C1c2cc(Nc3cccnn3)ccc2OCCN1C[C@H](O)CN1CCc2ccccc2C1] |
| 40 | 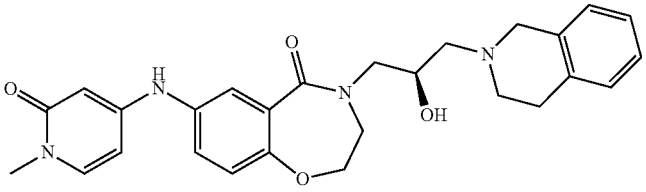 [SMILES: Cn1ccc(Nc2ccc3c(c2)C(=O)N(C[C@H](O)CN2CCc4ccccc4C2)CCO3)cc1=O] |
| 41 | 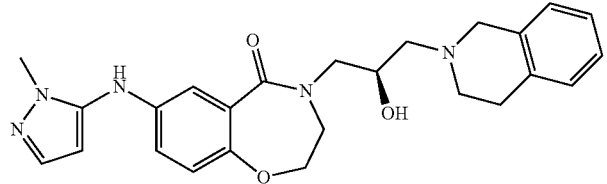 [SMILES: Cn1nccc1Nc1ccc2c(c1)C(=O)N(C[C@H](O)CN1CCc3ccccc3C1)CCO2] |
| 42 | 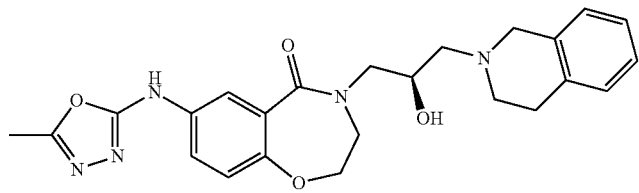 [SMILES: Cc1nnc(Nc2ccc3c(c2)C(=O)N(C[C@H](O)CN2CCc4ccccc4C2)CCO3)o1] |
| 43 | 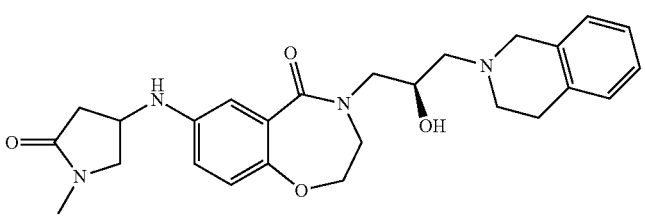 [SMILES: CN1CC(Nc2ccc3c(c2)C(=O)N(C[C@H](O)CN2CCc4ccccc4C2)CCO3)CC1=O] |

TABLE 1A-continued

| # | Structure |
|---|---|
| 44 | 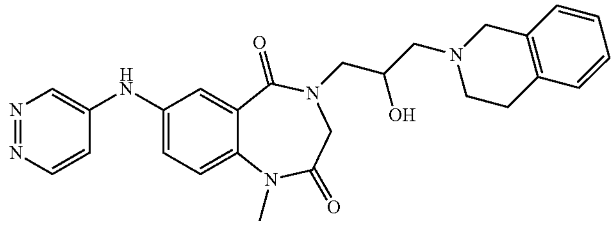 [SMILES: CN1C(=O)CN(CC(O)CN2CCc3ccccc3C2)C(=O)c2cc(Nc3ccnnc3)ccc21] |
| 45 | 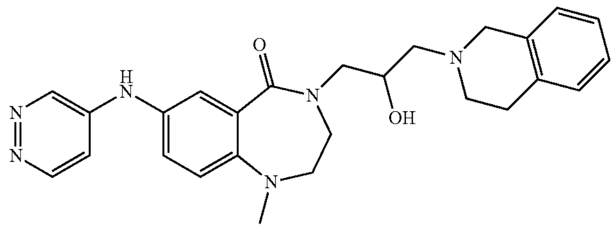 [SMILES: CN1CCN(CC(O)CN2CCc3ccccc3C2)C(=O)c2cc(Nc3ccnnc3)ccc21] |
| 46 | 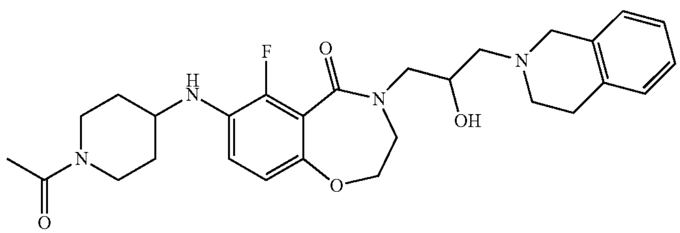 [SMILES: CC(=O)N1CCC(Nc2ccc3c(c2F)C(=O)N(CC(O)CN2CCc4ccccc4C2)CCO3)CC1] |
| 46a | 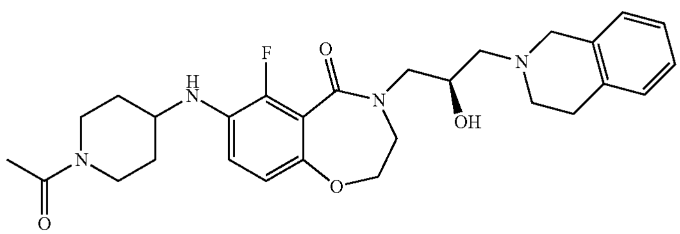 [SMILES: CC(=O)N1CCC(Nc2ccc3c(c2F)C(=O)N(C[C@H](O)CN2CCc4ccccc4C2)CCO3)CC1] |
| 46b | 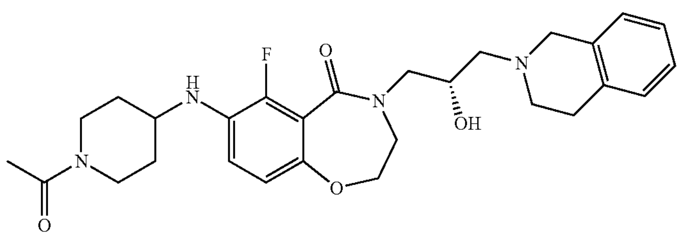 [SMILES: CC(=O)N1CCC(Nc2ccc3c(c2F)C(=O)N(C[C@@H](O)CN2CCc4ccccc4C2)CCO3)CC1] |
| 47 | 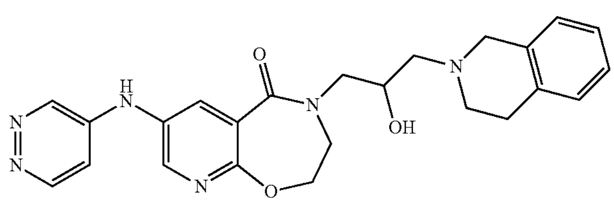 [SMILES: O=C1c2cc(Nc3ccnnc3)cnc2OCCN1CC(O)CN1CCc2ccccc2C1] |
| 48 | 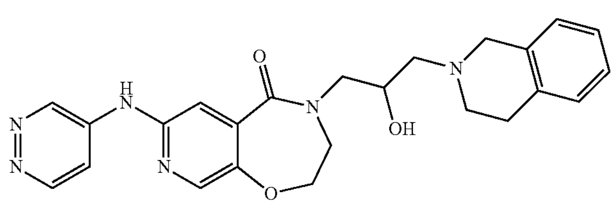 |

TABLE 1A-continued

| # | Structure |
|---|-----------|
| 49 | 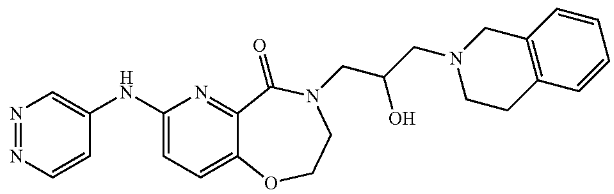 [SMILES: O=C1c2nc(Nc3ccnnc3)ccc2OCCN1CC(O)CN1CCc2ccccc2C1] |
| 50 | 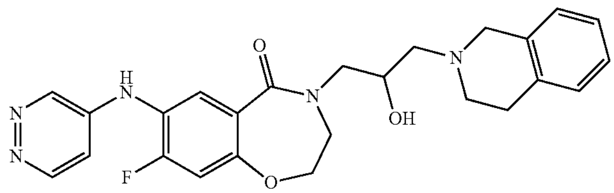 [SMILES: O=C1c2cc(Nc3ccnnc3)c(F)cc2OCCN1CC(O)CN1CCc2ccccc2C1] |
| 51 | 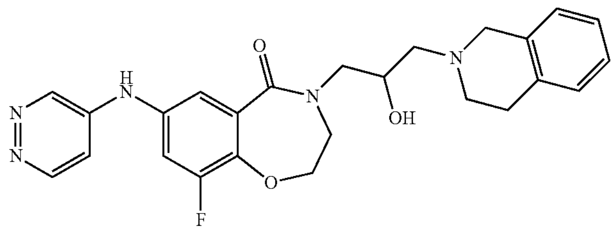 [SMILES: O=C1c2cc(Nc3ccnnc3)cc(F)c2OCCN1CC(O)CN1CCc2ccccc2C1] |
| 52 | 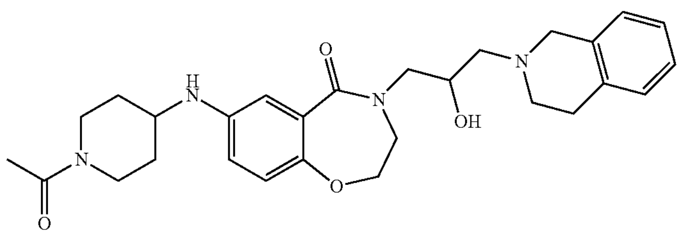 [SMILES: CC(=O)N1CCC(Nc2ccc3c(c2)C(=O)N(CC(O)CN2CCc4ccccc4C2)CCO3)CC1] |
| 52a | 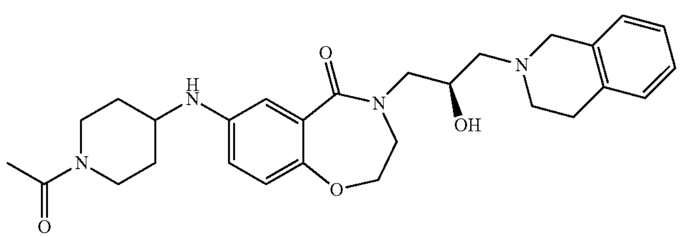 [SMILES: CC(=O)N1CCC(Nc2ccc3c(c2)C(=O)N(C[C@H](O)CN2CCc4ccccc4C2)CCO3)CC1] |
| 52b | 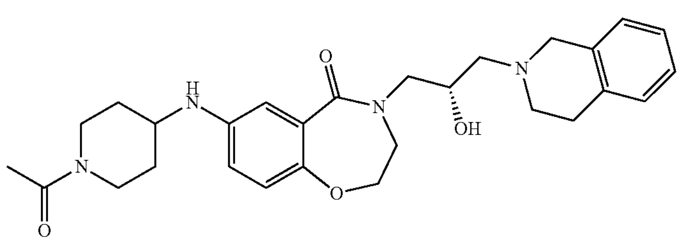 [SMILES: CC(=O)N1CCC(Nc2ccc3c(c2)C(=O)N(C[C@@H](O)CN2CCc4ccccc4C2)CCO3)CC1] |
| 53 | 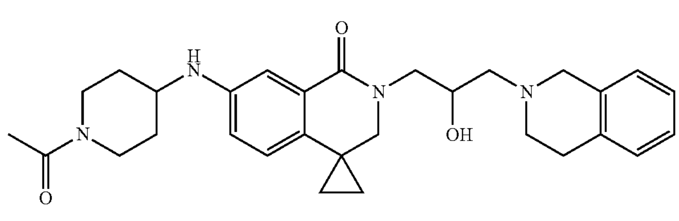 [SMILES: CC(=O)N1CCC(Nc2ccc3c(c2)C(=O)N(CC(O)CN2CCc4ccccc4C2)CC32CC2)CC1] |

TABLE 1A-continued

| # | Structure |
|---|---|
| 53a | 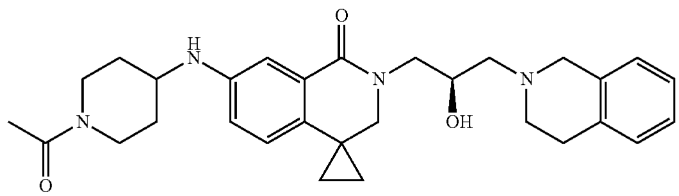 [SMILES: CC(=O)N1CCC(Nc2ccc3c(c2)C(=O)N(C[C@H](O)CN2CCc4ccccc4C2)CC32CC2)CC1] |
| 53b | 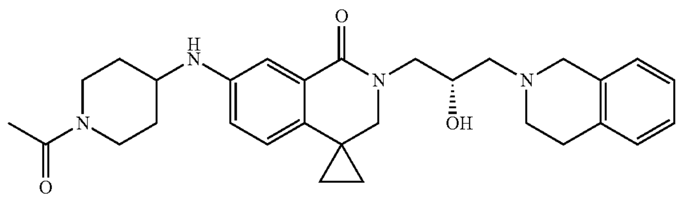 [SMILES: CC(=O)N1CCC(Nc2ccc3c(c2)C(=O)N(C[C@@H](O)CN2CCc4ccccc4C2)CC32CC2)CC1] |
| 54 | 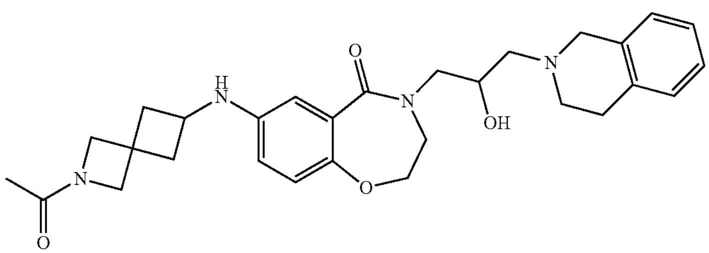 [SMILES: CC(=O)N1CC2(CC(Nc3ccc4c(c3)C(=O)N(CC(O)CN3CCc5ccccc5C3)CCO4)C2)C1] |
| 55 | 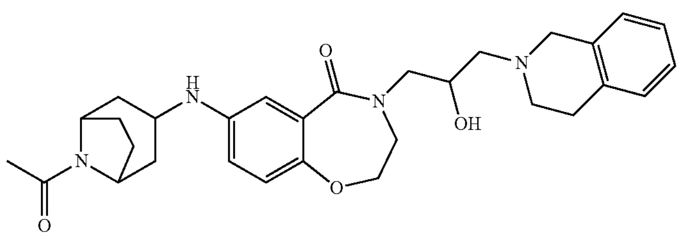 [SMILES: CC(=O)N1C2CCC1CC(Nc1ccc3c(c1)C(=O)N(CC(O)CN1CCc4ccccc4C1)CCO3)C2] |
| 56 | 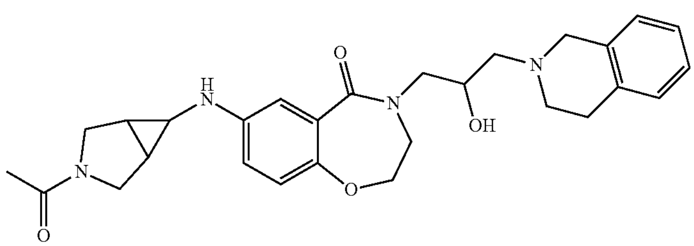 [SMILES: CC(=O)N1CC2C(C1)C2Nc1ccc2c(c1)C(=O)N(CC(O)CN1CCc3ccccc3C1)CCO2] |
| 57a | 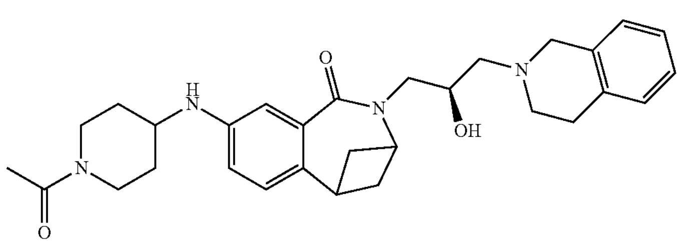 [SMILES: CC(=O)N1CCC(Nc2ccc3c(c2)C(=O)N(C[C@H](O)CN2CCc4ccccc4C2)C2CC3C2)CC1] |

TABLE 1A-continued

| # | Structure |
|---|---|
| 57b | 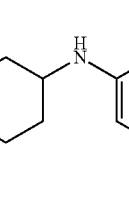 |

In preferred embodiments of the invention, $R_1$ in Formula (I) is 1-acetylpiperidin-4-yl, 1-methyl-1H-pyrazol-4-yl, or pyridazin-4-yl; W is —NH—; T, U, and V are all carbon atoms; $R_2$ is H or F; m is 1; X is a carbon atom or an oxygen atom; Y is a carbon atom; Z is a direct bond or a carbon atom; $R_3$ is H; and ===== stands for a single bond. Table 1B lists some compounds that are effective against cell lines of Z-138, U-251, and MIA PaCa2, as will be described in more details in the EXAMPLE section.

TABLE 1B

| # | Structure |
|---|---|
| 2a | 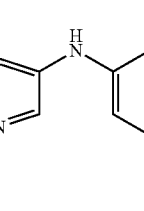 |
| 12a | 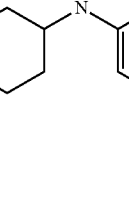 |
| 24a | 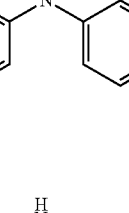 |
| 28a | 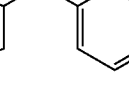 |
| 29a | 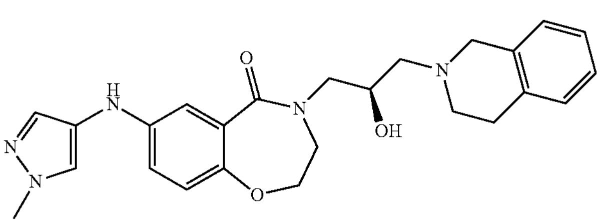 [SMILES: Cn1cc(Nc2ccc3c(c2)C(=O)N(C[C@H](O)CN2CCc4ccccc4C2)CCO3)cn1] |

TABLE 1B-continued

| # | Structure |
|---|---|
| 30a | 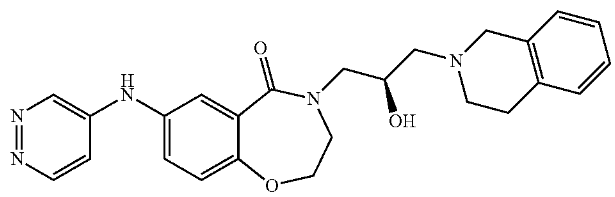 [SMILES: O=C1c2cc(Nc3ccnnc3)ccc2OCCN1C[C@H](O)CN1CCc2ccccc2C1] |
| 52a | 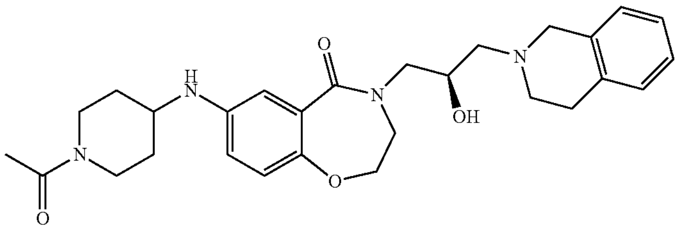 [SMILES: CC(=O)N1CCC(Nc2ccc3c(c2)C(=O)N(C[C@H](O)CN2CCc4ccccc4C2)CCO3)CC1] |
| 52b | 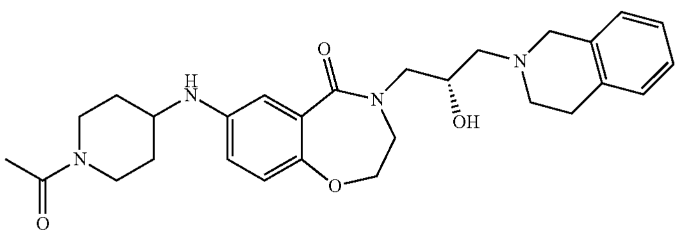 [SMILES: CC(=O)N1CCC(Nc2ccc3c(c2)C(=O)N(C[C@@H](O)CN2CCc4ccccc4C2)CCO3)CC1] |

In more preferred embodiments of the invention, compounds of Formula (I) include (R)-7-((1-acetylpiperidin-4-yl)amino)-2-(3-(3,4-dihydroisoquinolin-2(1H)-yl)-2-hydroxypropyl)-3,4-dihydroisoquinolin-1(2H)-one (24a), and (R)-7-((1-acetylpiperidin-4-yl)amino)-4-(3-(3,4-dihydroisoquinolin-2(1H)-yl)-2-hydroxypropyl)-3,4-dihydrobenzo[f][1,4]oxazepin-5(2H)-one (52a). These compounds are effective for three cancer cell panels' proliferation inhibition screening; and show promising pharmacokinetic result in mouse, rat and dog, as will be described in more details in the EXAMPLE section. Particularly, (R)-7-((1-acetylpiperidin-4-yl)amino)-4-(3-(3,4-dihydroisoquinolin-2(1H)-yl)-2-hydroxypropyl)-3,4-dihydrobenzo[f][1,4]oxazepin-5(2H)-one (52a) further demonstrates a promising result in mantle cell lymphoma (MCL) Z-138 xenograft efficacy studies, as will be described in more details in the EXAMPLE section.

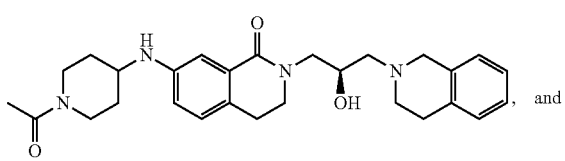

(24a) and

-continued

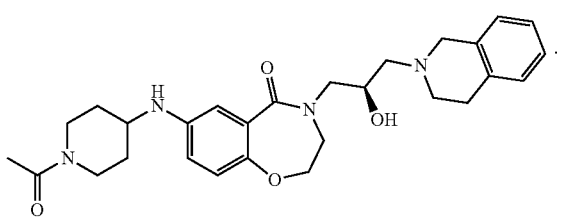

(52a)

The present invention may include all pharmaceutically acceptable isotopically labelled compounds of Formula (I) or salts thereof, wherein one or more atoms are replaced by atoms having the same atomic number, but an atomic mass or mass number different from the atomic mass or mass number which predominates in nature. Examples of isotopes suitable for inclusion in the compounds of the invention include isotopes of hydrogen, such as $^2$H and $^3$H, carbon, such as $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically labelled compounds of Formula (I), for example, those incorporating a radioactive isotope, are useful in drug and/or substrate tissue distribution studies. The radioactive isotopes tritium, i.e., $^3$H, and carbon-14, i.e., 14C, are particularly useful for this purpose in view of their ease of incorporation and detection. Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. Substitution with positron-emitting isotopes, such as $^{11}C$, $^{18}F$, $^{15}O$ and $^{13}N$, can be useful in Positron Emission Topography (PET) studies for examining substrate receptor occupancy. Isotopically labeled compounds of Formula (I) can generally be prepared by conventional techniques known to those skilled in the art using an appropriate isotopically labeled reagent in place of the non-labeled reagent previously employed.

Regarding isomers, some compounds of Formula (I) may include stereoisomers and tautomers, all of which are included within the scope of the invention. Stereoisomers of Formula (I) include cis and trans isomers, optical isomers such as R and S enantiomers, diastereomers, geometric isomers, rotational isomers, atropisomers, and conformational isomers of the compounds of Formula (I), including compounds exhibiting more than one type of isomerism; and mixtures thereof (such as racemates and diastereomeric pairs).

The compounds of Formula (I) may exist in the form of pharmaceutically acceptable salts such as acid addition salts and/or base salts thereof. Suitable acid addition salts are formed from acids which form non-toxic salts e.g. hydrochloride/chloride. Suitable base salts are formed from bases which form non-toxic salts such as calcium and sodium salts. Hemisalts of acids and bases may also be formed, for example, hemisulfate and hemicalcium salts.

The compounds of Formula (I) or a pharmaceutically acceptable salt thereof include all forms of the compound of Formula (I) or pharmaceutically salt thereof, including hydrates, solvates, isomers (e.g. rotational stereoisomers), crystalline and non-crystalline forms, isomorphs, polymorphs, metabolites, and prodrugs thereof. Compounds of Formula (I) may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions.

The compounds of Formula (I) may exist in a continuum of solid states ranging from fully amorphous to fully crystalline. The term "amorphous" refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point"). The compounds of the invention may also exist in a mesomorphic state (mesophase or liquid crystal) when subjected to suitable conditions. The mesomorphic state is intermediate between the true crystalline state and the true liquid state (either melt or solution).

The invention also relates to prodrugs of the compounds of Formula (I). Some compounds of Formula (I) may have little or no pharmacological activity themselves, but they can, when administered into or onto the body, be converted into compounds of Formula (I) having the desired activity, for example, by hydrolytic cleavage. Such derivatives are referred to as "prodrugs". Prodrugs in accordance with the invention can, for example, be produced by replacing appropriate functionalities present in the compounds of Formula (I) with certain moieties known to those skilled in the art as "pro-moieties". In some embodiments, certain compounds of Formula (I) may themselves act as prodrugs of other compounds of Formula (I). Metabolites of compounds of Formula (I) formed in vivo upon administration of the drug are also included within the scope of the invention.

Compound Preparation

Starting materials and intermediates useful for making the compounds of the present invention can be obtained from chemical vendors or can be made according to methods described in the chemical art.

Compounds of the invention, including salts of the compounds, can be prepared using known organic synthesis techniques and can be synthesized according to any of numerous possible synthetic routes. The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention may involve the protection and deprotection of various chemical groups. The need for protection and deprotection, and the selection of appropriate protecting groups, can be readily determined by one skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion. For another example, an —S— can be oxidized to —S(═O)— and/or —S(═O)$_2$—. For yet another example, an unsaturated bond such as C—C double bond or C—C triple bond can be reduced to a saturated bond by hydrogenation.

Functional (reactive) groups can be protected/deprotected in the course of the synthetic scheme, if appropriate and/or desired. For example, an OH group can be protected by a benzyl, methyl, or acetyl group, which can be deprotected and converted back to the OH group in a later stage of the synthetic process. For another example, an NH$_2$ group can be protected by a benzyloxycarbonyl (Cbz) or BOC group; conversion back to the NH$_2$ group can be carried out at a later stage of the synthetic process via deprotection.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

In some embodiments, the compounds may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization, and one or both of the diastereoisomers converted to the corresponding pure enantiomer(s) by means well known to one skilled in the art. Chiral compounds (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. Suitable stereoselective techniques are well known to those of ordinary skill in the art. For a compound of Formula (I) that contains an alkenyl or alkenylene group, geometric cis/trans (or Z/E) isomers are possible. Cis/trans isomers may be separated by conventional techniques well known to those skilled in the art, for example, chromatography and fractional crystallization.

Pharmaceutical Composition and Administration

The present invention also provides a pharmaceutical composition comprising a therapeutically effective amount of the compound of Formula (I), or a pharmaceutically acceptable salt, ester, prodrug, complex, solvate, isomer, or hydrate thereof, in any crystalline form or in amorphous form, a pharmaceutically acceptable carrier or excipient, and optionally comprising at least one additional medicinal or pharmaceutical agent.

The pharmaceutically acceptable carrier or excipient may comprise any conventional pharmaceutical carrier or excipient. Suitable pharmaceutical carriers include inert diluents or fillers, water and various organic solvents such as hydrates and solvates. The pharmaceutical compositions may, if desired, contain additional ingredients such as flavorings, binders, excipients and the like.

The term "therapeutically effective amount" as used herein refers to that amount of the compound (including a pharmaceutically acceptable salt thereof) being administered which will relieve to some extent one or more of the symptoms of the disorder being treated. In reference to the treatment of a PRMT5-mediated disease or disorder, a therapeutically effective amount refers to that amount which has the effect of relieving to some extent or eliminating one or more symptoms associated with the PRMT5-mediated disease or disorder. The term "treating", as used herein, unless otherwise indicated, means reversing, alleviating, inhibiting the progress of, or preventing the disorder or condition to which such term applies, or one or more symptoms of such disorder or condition. The term "treating" also includes adjuvant and neo-adjuvant treatment of a subject.

Administration of the compounds of Formula (I) (including salts thereof) may be effected by any method that enables delivery of the compounds to the site of action. These methods include, for example, enteral routes (e.g., oral routes, buccal routes, sublabial routes, and sublingual routes), oral routes, intranasal routes, inhaled routes, intraduodenal routes, parenteral injection (including intravenous, subcutaneous, intramuscular, intravascular or infusion), intrathecal routes, epidural routes, intracerebral routes, intracerbroventricular routes, topical, and rectal administration. In one embodiment of the present invention, the compounds of Formula (I) may be administered/effected by parenteral injection routes (e.g., intravenous injection route). In one embodiment of the present invention, the compounds of Formula (I) may be administered or effected by oral routes.

Dosage of the compounds of Formula (I) may be adjusted to provide the desired response. It is to be noted that dosage values may vary with the type and severity of the condition to be alleviated, and may include single or multiple doses.

Kit or Packaged Pharmaceutical

The present invention provides a kit or packaged pharmaceutical comprising a compound of Formula (I), or a pharmaceutically acceptable salt, ester, prodrug, complex, solvate, isomer, or hydrate thereof, in any crystalline form or in amorphous form, and instructions for use thereof.

The kits (e.g., pharmaceutical packs) may include a provided pharmaceutical composition or compound and a container (e.g., a vial, ampule, bottle, syringe, and/or dispenser package, or other suitable container). In some embodiments, the kits may optionally further include a second container comprising a pharmaceutical excipient for dilution or suspension of the pharmaceutical composition or compound. In some embodiments, a pharmaceutical composition or compound is provided in two containers, and when it is needed, the contents in the two containers are combined to form one unit dosage form.

Applications

The present invention provides a method of inhibiting a protein arginine methyltransferase 5 (PRMT5) enzyme, comprising: contacting the PRMT5 enzyme with an effective amount of a compound of Formula (I), or a pharmaceutically acceptable salt, ester, prodrug, complex, solvate, isomer, or hydrate thereof, in any crystalline form or in amorphous form.

The step of inhibiting may be carried out in vitro or in vivo. "In vitro" refers to procedures performed in an artificial environment such as, e.g., without limitation, in a test tube or culture medium. "In vivo" refers to procedures performed within a living organism such as, without limitation, a human, a mouse, dog, rat or rabbit.

As used herein, the term "IC50" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the method of the invention utilizes the PRMT5 inhibitor of Formula (I) with an IC50 value of about or less than a predetermined value, as ascertained in an in vitro assay. In some embodiments, the PRMT5 inhibitor inhibits PRMT5 a with an IC50 value of about 10 nM or less, 20 nM or less, 30 nM or less, 40 nM or less, 50 nM or less, 60 nM or less, 70 nM or less, 80 nM or less, 90 nM or less, 100 nM or less, 150 nM or less, 200 nM or less, 300 nM or less, 400 nM or less, 500 nM or less, 600 nM or less, 700 nM or less, 800 nM or less, 900 nM or less, 1000 nM or less, 1500 nM or less, 2000 nM or less, or 2500 nM or less (or a number in the range defined by and including any two numbers above).

The present invention provides a method of altering gene expression or altering transcription comprising contacting a cell in vitro or in a subject with an effective amount of a compound of Formula (I), or a pharmaceutically acceptable salt, ester, prodrug, complex, solvate, isomer, or hydrate thereof, in any crystalline form or in amorphous form. In certain embodiments, the cell is in culture in vitro. In certain embodiments, the cell is in an animal, e.g., a human. In certain embodiments, the cell is in a subject in need of treatment.

In some embodiments, a compound of Formula (I) is useful in somatic cell reprogramming, such as reprogramming somatic cells into stem cells. In some embodiments, a compound of Formula (I) is useful in germ cell development, and are thus envisioned useful in the areas of reproductive technology and regenerative medicine.

The present invention provides a method of treating a disorder or disease mediated by PRMT5 or associated with aberrant PRMT5 activity, comprising administering to a subject in need thereof a therapeutically effective amount of a compound of Formula (I), or a pharmaceutically acceptable salt, ester, prodrug, complex, solvate, isomer, or hydrate thereof, in any crystalline form or in amorphous form; or a pharmaceutical composition thereof.

As used herein, the term "PRMT5-mediated disorder" means any disease, disorder, or other pathological condition in which PRMT5 is known to play a role. Accordingly, in some embodiments, the present invention relates to treating or lessening the severity of one or more diseases in which PRMT5 is known to play a role. The methods of the invention are useful for treating a disease condition associated with PRMT5. Any disease condition that results directly or indirectly from an abnormal activity or expression level of PRMT5 can be an intended disease condition. Different disease conditions associated with PRMT5 have been reported. PRMT5 has been implicated, for example, in a variety of human cancers as well as a number of hemoglobinopathies.

The disorder or disease includes a proliferative disorder such as cancer, a metabolic disorder such as diabetes or obesity, a blood disorder such as hemoglobinopathy, e.g. sickle cell anemia or beta-thalessemia, an autoimmune disease, or an inflammatory disease.

For example, while not being bound to any particular theory, a role for PRMT5 has been recognized in adipogenesis. Inhibition of PRMT5 expression in multiple cell culture models for adipogenesis prevented the activation of adipogenic genes, while over expression of PRMT5 enhanced adipogenic gene expression and differentiation. Additionally, it has been shown that adipogenesis plays a pivotal role in the etiology and progression of diabetes and obesity. Thus in some embodiments, the inhibition of PRMT5 by a compound of Formula (I) is useful in treating diabetes and/or obesity. In some embodiments, a compound of Formula (I) is useful to delay the onset of, slow the progression of, or ameliorate the symptoms of, diabetes. In some embodiments, the diabetes is Type 1 diabetes. In some embodiments, the diabetes is Type 2 diabetes. In some embodiments, a compound of Formula (I) is useful to delay the onset of, slow the progression of, or ameliorate the symptoms of, obesity. In some embodiments, a compound of Formula (I) is useful to help a subject lose weight. In some embodiments, a compound of Formula (I) could be used in combination with other compounds, drugs, or therapeutics, such as metformin and insulin, to treat diabetes and/or obesity.

In some embodiments, a compound of Formula (I) is useful in treating a blood disorder, e.g., a hemoglobinopathy, such as sickle cell disease or .beta.-thalassemia. For example, while not being bound to any particular theory, PRMT5 is a known repressor of gamma-globin gene expression, and increased fetal gamma-globin (HbF) levels in adulthood are associated with symptomatic amelioration in sickle cell disease and P3-thalassemia. Thus in some embodiments, the inhibition of PRMT5 by a compound Formula (I) is useful in treating a blood disorder, such as a hemoglobinopathy such as sickle cell disease or beta-thalassemia. In some embodiments, a compound of Formula (I) is useful to delay the onset of, slow the progression of, or ameliorate the symptoms of, sickle cell disease. In some embodiments, a compound of Formula (I) is useful to delay the onset of, slow the progression of, or ameliorate the symptoms of, beta-thalassemia. In some embodiments, a compound of Formula (I) could be used in combination with other compounds, drugs, or therapeutics, to treat a hemoglobinopathy such as sickle cell disease or beta-thalassemia.

In some embodiments, a compound of Formula (I) is useful in treating inflammatory and autoimmune disease. PRMT5 is reported to activate NFkB signaling pathway through the methylation of p65. PRMT5 is reported to interact with Death receptor 4 and Death receptor 5 contributing to TRAIL-induced activation of inhibitor or kB kinase (IKK) and nuclear factor-kB (NF-kB). The term "inflammatory disease" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

In preferred embodiments, a compound of Formula (I) is useful in treating a proliferative disorder, such as cancer or a benign neoplasm. For example, while not being bound to any particular theory, PRMT5 has been shown to be involved in cyclin D1 dysregulated cancers. Increased PRMT5 activity mediates key events associated with cyclin D1-dependent neoplastic growth including CUL4 repression, CDT1 overexpression, and DNA re-replication. Further, human cancers harboring mutations in Fbx4, the cyclin D1 E3 ligase, exhibit nuclear cyclin D1 accumulation and increased PRMT5 activity. Additionally, PRMT5 has also been implicated in accelerating cell cycle progression through G1 phase and modulating regulators of G1; for example, PRMT5 may upregulate cyclin-dependent kinase (CDK) 4, CDK6, and cyclins D1, D2 and E1. Moreover, PRMT5 may activate phosphoinositide 3-kinase (PI3K)/AKT signaling.

The disorder or disease includes breast cancer, lung cancer, pancreatic cancer, prostate cancer, colon cancer, ovarian cancer, skin cancer, testicular cancer, uterine cancer, cervical cancer, esophageal cancer, bladder cancer, gastric cancer, liver cancer, epidermoid cancer, brain cancer, hematopoietic cancer, leukemia such as acute myeloid leukemia (AML), acute lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), hemoglobinopathies such as beta-thalassemia and sickle cell disease (SCD), lymphoma, medulloblastoma, rectum adenocarcinoma, colon adenocarcinoma, adenoid cystic carcinoma, lung adenocarcinoma, head and neck squamous cell carcinoma, hepatocellular carcinoma, renal cell carcinoma, oligodendroglioma, ovarian clear cell carcinoma, ovarian serous cystadenocarcinoma, melanoma, or any combination thereof.

The disorder or disease comprises lymphoma representable by cell lines such as Raji, SU-DHL4, and Z138; or glioma representable by cell lines such as U87MG, U251 and T98G.

The disorder or disease is pancreas cancer representable by cell lines such as IMIMPC2, MIA PaCa2, Aspc1, A6L, SKPC1 and Panc-1.

The disorder or disease includes breast cancer representable by cell lines such as 600MPE, AU565, BT-20, BT-474, BT-483, BT-549, Evsa-T, Hs578T, MCF-7, MDA-MB-231, MDA-MB-453, MDA-MB-468, SkBr3, and T-47D; liver cancer representable by cell lines such as Hep G2, Huh1, Huh7, SNU398, SNU475, and MHCC-97H; or lung cancer representable by cell lines such as A-549, EBC-1, and HCC827.

Compounds of Formula (I), as well as pharmaceutical compositions comprising them, can be administered to treat any of the described diseases, alone or in combination with a medical therapy. Medical therapies include, for example, surgery and radiotherapy (e.g. gamma-radiation, neutron beam radiotherapy, electron beam radiotherapy, proton therapy, brachytherapy, systemic radioactive isotopes).

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art.

EXAMPLES

The following illustrate the synthesis of various compounds of the present invention. Additional compounds within the scope of this invention may be prepared using the methods illustrated in these Examples, either alone or in combination with techniques generally known in the art.

Example 1: 2-(3-(3,4-dihydroisoquinolin-2(1H)-yl)-2-hydroxypropyl)-7-(oxetan-3-ylamino)-3,4-dihydroisoquinolin-1(2H)-one (1)

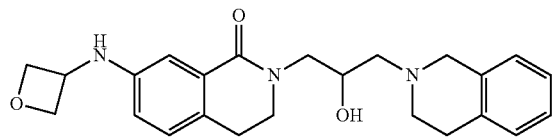

(1)

Step 1: 1-chloro-3-(3,4-dihydroisoquinolin-2(1H)-yl)propan-2-ol

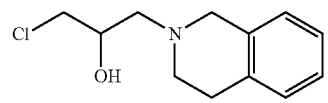 [SMILES: OC(CCl)CN1CCc2ccccc2C1]

A mixture of 1,2,3,4-tetrahydroisoquinoline (10.00 g, 75.1 mmol, 1.0 eq.) and 2-(chloromethyl)-oxirane (6.98 g, 75.5 mmol, 1.0 eq.) in isopropanol (100 mL) was stirred at ambient temperature overnight. The reaction mixture was concentrated to dryness, and the obtained residue was purified by a column chromatography (200-300 mesh silica gel, petroleum ether/ethyl acetate (PE/EA=1/1) to afford 1-chloro-3-(3,4-dihydroisoquinolin-2(1H)-yl) propan-2-ol (10.00 g, 59% yield) as a yellow oil. $^1$HNMR (400 MHz, Deuterochloroform (CDCl$_3$)) δ (ppm) 7.13-7.20 (m, 3H), 7.03-7.05 (m, 1H), 4.03-4.09 (m, 1H), 4.85 (d, J=14.8 Hz, 1H), 3.61-3.69 (m, 3H), 2.93-2.99 (m, 3H), 2.67-2.84 (m, 3H).

Step 2: 7-bromo-2-(3-(3,4-dihydroisoquinolin-2 (1H)-yl)-2-hydroxypropyl)-3,4-dihydroisoquinolin-1 (2H)-one (I-1)

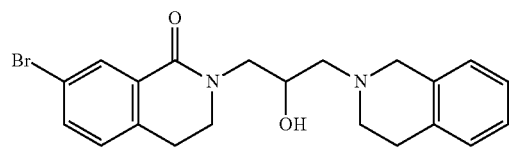

(I-1)

To a stirred suspension of Sodium Hydride (NaH) (60% in oil, 115 mg, 2.83 mmol, 1.2 eq.) in Dimethylformamide (DMF, 5 mL) was added a solution of 7-bromo-3,4-dihydro isoquinolin-1(2H)-one (500 mg, 2.36 mmol, 1.0 eq.) in DMF (5 mL), and the resultant mixture was stirred at ambient temperature for 1 hour. A solution of 1-chloro-3-(3,4-dihydroisoquinolin-2(1H)-yl)propan-2-ol (650 mg, 2.83 mmol, 1.2 eq.) in DMF (5 mL) was added, and the resultant mixture was heated to 70° C. for additional 3 hours. The reaction mixture was treated with water and EA, and organic phase was separated. Organic phase was washed with water, dried over Na$_2$SO$_4$, and was concentrated to dryness. The crude material was purified by a column chromatography (200-300 mesh silica gel, PE/EA=2/1) to afford 7-bromo-2-(3-(3,4-dihydro isoquinolin-2(1H)-yl)-2-hydroxypropyl)-3,4-dihydroisoquinolin-1(2H)-one (270 mg, 28% yield) as a yellowish oil.

Step 3: 2-(3-(3,4-dihydroisoquinolin-2(1H)-yl)-2-hydroxypropyl)-7-(oxetan-3-ylamino)-3,4-dihydroisoquinolin-1(2H)-one (1)

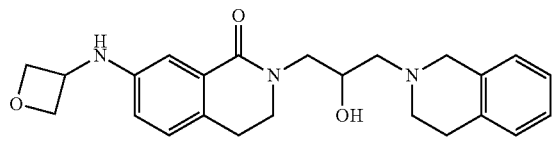 [SMILES: O=C1c2cc(NC3COC3)ccc2CCN1CC(O)CN1CCc2ccccc2C1]

To a stirred solution of 7-bromo-2-(3-(3,4-dihydroisoquinolin-2(1H)-yl)-2-hydroxypropyl)-3,4-dihydroisoquinolin-1(2H)-one (I-1) (270 mg, 0.65 mmol, 1.0 eq.) and oxetan-3-amine (95 mg, 1.30 mmol, 2.0 eq.) in 1,4-dioxane (50 mL) was added solid $Cs_2CO_3$ (423 mg, 1.30 mmol, 2.0 eq.), catalytic amount of 4,5-bis(diphenylphosphino)-9,9-dimethylxanthene (XantPhos) and tris(dibenzylideneacetone)dipalladium(0) ($Pd_2(dba)_3$). The resultant mixture was heated to reflux under nitrogen atmosphere for 6 hours. The reaction mixture was treated with water and EA, and organic phase was separated. Organic phase was washed with water, dried over $Na_2SO_4$, and was concentrated to dryness. The crude material was purified by a column chromatography (200-300 mesh silica gel, Dichloromethane/Methanol (DCM/MeOH=40/1) to afford 2-(3-(3,4-dihydroisoquinolin-2(1H)-yl)-2-hydroxypropyl)-7-(oxetan-3-ylamino)-3,4-dihydroisoquinolin-1(2H)-one (1) (150 mg, 57% yield) as a light yellow solid. $^1$H NMR (400 MHz, DMSO-$d_6$) δ (ppm) 6.98-7.09 (m, 6H), 6.58 (dd, J=2.1 Hz, 8.0 Hz, 1H), 6.41 (d, J=6.4 Hz, 1H), 4.81-4.85 (m, 3H), 4.49-4.53 (m, 1H), 4.38 (t, J=5.9 Hz, 2H), 4.01 (brs, 1H), 3.76 (dd, J=3.8 Hz, 13.5 Hz, 1H), 3.50-3.62 (m, 4H), 3.20 (dd, J=7.6 Hz, 13.5 Hz, 1H), 2.71-2.79 (m, 6H), 2.47-2.50 (m, 2H); LC-MS (m/z): 408 [M+H]$^+$.

Example 2: 2-(3-(3,4-dihydroisoquinolin-2(1H)-yl)-2-hydroxypropyl)-7-(pyrimidin-5-yl)-3,4-dihydroisoquinolin-1(2H)-one (14)

(14)

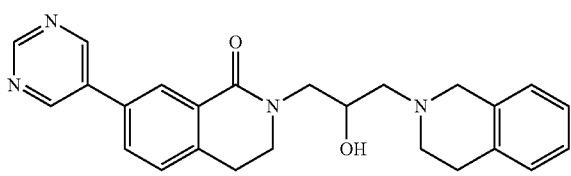

To a stirred solution of 7-bromo-2-(3-(3,4-dihydroisoquinolin-2(1H)-yl)-2-hydroxypropyl)-3,4-dihydroisoquinolin-1(2H)-one (I-1) (160 mg, 0.38 mmol, 1.0 eq.) in ethanol (15 ml) was added pyrimidin-5-ylboronic acid (57 mg, 0.46 mmol, 1.2 eq.), catalytic amount of Dichlorobis(triphenylphosphine) palladium(II) ($Pd(PPh_3)_2Cl_2$), and a solution of $K_2CO_3$ (105 mg, 0.76 mmol, 2.0 eq.) in $H_2O$ (5 ml), and the resultant mixture was heated to reflux under nitrogen gas atmosphere for 6 hours. The reaction mixture was treated with water, and was extracted with EA. Organic phase was washed with brine, dried over $Na_2SO_4$, and was concentrated to dryness. The crude material was purified by a column chromatography (200-300 mesh silica gel, DCM/MeOH=30/1) to afford 2-(3-(3,4-dihydroisoquinolin-2(1H)-yl)-2-hydroxypropyl)-7-(pyrimidin-5-yl)-3,4-dihydroisoquinolin-1(2H)-one (14) (30 mg, 20% yield) as a yellow oil. $^1$HNMR (400 MHz, DMSO-$d_6$) δ (ppm) 9.20 (s, 1H), 9.13 (s, 2H), 8.20 (s, 1H), 7.88 (d, J=7.6 Hz, 1H), 7.45 (d, J=7.7 Hz, 1H), 7.03-7.07 (m, 4H), 4.88 (brs, 1H), 4.09 (brs, 1H), 3.63-3.87 (m, 5H), 3.25-3.31 (m, 1H), 3.02-3.03 (m, 2H), 2.67-2.79 (m, 6H); LC-MS (m/z): 415 [M+H]$^+$.

Example 3: 2-(3-(3,4-dihydroisoquinolin-2(1H)-yl)-2-hydroxypropyl)-4,4-dimethyl-7-(oxetan-3-ylamino)-3,4-dihydroisoquinolin-1(2H)-one (15)

(15)

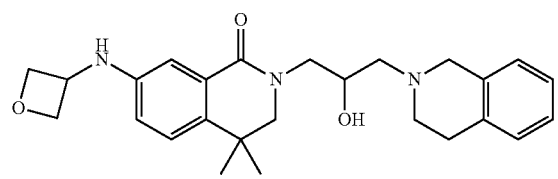

Step 1: 2-(4-bromophenyl)-2-methylpropanenitrile

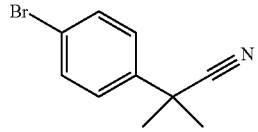

To a stirred suspension of NaH (60% in oil, 8.98 g, 224.4 mmol, 2.2 eq.) in tetrahydrofuran (THF, 300 ml) was added a solution of 2-(4-bromophenyl)acetonitrile (20.00 g, 102.0 mmol, 1.0 eq.) in THF (100 ml), and the resultant mixture was stirred at ambient temperature for additional 1 hour. $CH_3I$ (31.85 g, 224.4 mmol, 2.2 eq.) was added dropwise, and the obtained mixture was stirred at ambient temperature overnight. The reaction mixture was quenched with cold water, and was extracted with EA. Organic phase was washed with brine, dried over $Na_2SO_4$, and was concentrated to dryness. The crude material was purified by a column chromatography (200-300 mesh silica gel, PE) to afford 2-(4-bromophenyl)-2-methylpropanenitrile (20.88 g, 91% yield) as a yellow liquid. $^1$HNMR (400 MHz, $CDCl_3$) δ (ppm) 1.73 (s, 6H), 7.35-7.27 (m, 2H), 7.52-7.54 (m, 2H).

Step 2: 2-(4-bromophenyl)-2-methylpropan-1-amine

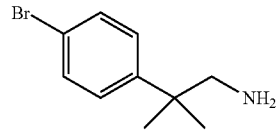

To a stirred solution of 2-(4-bromophenyl)-2-methylpropanenitrile (11.88 g, 53.0 mmol, 1.0 eq.) in THF (150 ml)

was added dropwise a solution of BH$_3$ in THF (1.0N, 159 ml, 159.0 mmol, 3.0 eq.) at an ice-water bath temperature, and the resultant mixture was heated to reflux for 4 hours. The reaction mixture was cooled to ambient temperature, and was concentrated to dryness. The obtained residue was dissolved in methanol, and was heated to reflux for additional 1 hour. The reaction mixture was concentrated to dryness again, and was treated with water. The aqueous phase was extracted with EA, washed with brine, dried over Na$_2$SO$_4$, and was concentrated to dryness. The crude material 2-(4-bromophenyl)-2-methylpropan-1-amine was used directly in next step without further purification.

Step 3: methyl (2-(4-bromophenyl)-2-methylpropyl)carbamate

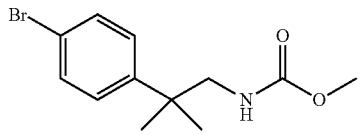 [SMILES: COC(=O)NCC(C)(C)c1ccc(Br)cc1]

To a stirred solution of crude 2-(4-bromophenyl)-2-methylpropan-1-amine in DMF (60 ml) was added triethylamine (6.44 g, 63.6 mmol, 1.2 eq.), followed by dropwise addition of methyl carbonochloridate (6.01 g, 63.6 mmol, 1.2 eq.), and the resultant mixture was stirred at ambient temperature overnight. The reaction mixture was quenched with water, and was filtered to collect precipitate. The obtained solid was further purified by a column chromatography (200-300 mesh silica gel, PE/EA=1/1) to afford methyl (2-(4-bromophenyl)-2-methylpropyl) carbamate (3.03 g, 19% yield over two steps) as a white solid.

Step 4: 7-bromo-4,4-dimethyl-3,4-dihydroisoquinolin-1(2H)-one

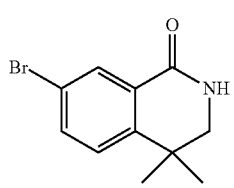

A solution of methyl (2-(4-bromophenyl)-2-methylpropyl)carbamate (3.03 g, 10.6 mmol, 1.0 eq.) in Trifluoromethanesulfonic acid (TfOH, 30 ml) was heated to 100° C. for 10 hours. The reaction mixture was cooled to ambient temperature, and was poured into cold water. The obtained aqueous phase was extracted with EA, washed with brine, dried over Na$_2$SO$_4$, and was concentrated to dryness. The crude material was purified by a column chromatography (200-300 mesh silica gel, PE/EA=2/1-1/1) to afford 7-bromo-4,4-dimethyl-3,4-dihydroisoquinolin-1(2H)-one (0.25 g, 10% yield) as a white solid.

Step 5: 7-bromo-4,4-dimethyl-2-(oxiran-2-ylmethyl)-3,4-dihydroisoquinolin-1(2H)-one

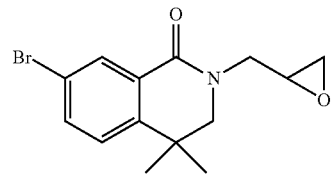 [SMILES: CC1(C)CN(CC2CO2)C(=O)c2cc(Br)ccc21]

To a stirred solution of 7-bromo-4,4-dimethyl-3,4-dihydroisoquinolin-1(2H)-one (150 mg, 0.59 mmol, 1.0 eq.) and 2-(chloromethyl)-oxirane (82 mg, 0.88 mmol, 1.5 eq) in DMF (5 ml) was added solid Cs$_2$CO$_3$ (577 mg, 1.77 mmol, 3.0 eq.), and the resultant mixture was heated to 90° C. for 3 hours. The reaction mixture was cooled to ambient temperature, and was quenched with water. The obtained aqueous phase was extracted with EA, washed with brine, dried over Na$_2$SO$_4$, and was concentrated to dryness. The crude material was used directly in next step without further purification.

Step 6: 7-bromo-2-(3-(3,4-dihydroisoquinolin-2(1H)-yl)-2-hydroxypropyl)-4,4-dimethyl-3,4-dihydroisoquinolin-1(2H)-one

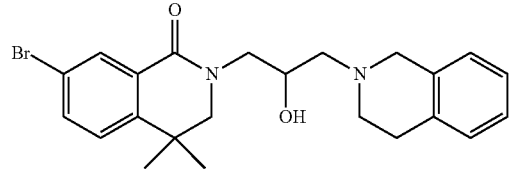 [SMILES: CC1(C)CN(CC(O)CN2CCc3ccccc3C2)C(=O)c2cc(Br)ccc21]

To a stirred solution of 7-bromo-4,4-dimethyl-2-(oxiran-2-ylmethyl)-3,4-dihydro isoquinolin-1(2H)-one in ethanol (10 ml) was added 1,2,3,4-tetrahydroisoquinoline (236 mg, 1.77 mmol, 3.0 eq.), and the resultant mixture was heated to reflux for 2 hours. The reaction mixture was concentrated to dryness, and the crude material was purified by a column chromatography (200-300 mesh silica gel, DCM) to afford 7-bromo-2-(3-(3,4-dihydro isoquinolin-2(1H)-yl)-2-hydroxypropyl)-4,4-dimethyl-3,4-dihydroisoquinolin-1(2H)-one (262 mg, >100% yield) as a yellow oil.

Step 7: 2-(3-(3,4-dihydroisoquinolin-2(1H)-yl)-2-hydroxypropyl)-4,4-dimethyl-7-(oxetan-3-ylamino)-3,4-dihydroisoquinolin-1(2H)-one (15)

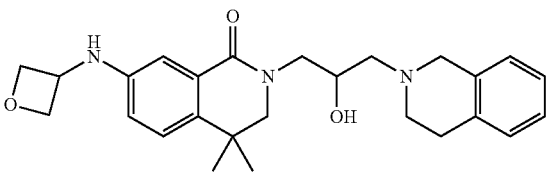 [SMILES: CC1(C)CN(CC(O)CN2CCc3ccccc3C2)C(=O)c2cc(NC3COC3)ccc21]

To a stirred solution of 7-bromo-2-(3-(3,4-dihydroisoquinolin-2(1H)-yl)-2-hydroxypropyl)-4,4-dimethyl-3,4-dihydro isoquinolin-1(2H)-one (262 mg, 0.59 mmol, 1.0 eq.)

and oxetan-3-amine (216 mg, 2.93 mmol, 5.0 eq.) in 1,4-dioxane (10 mL) was added solid Cs$_2$CO$_3$ (577 mg, 1.77 mmol, 3.0 eq.), catalytic amount of XantPhos and Pd$_2$(dba)$_3$. The resultant mixture was heated to reflux under nitrogen atmosphere for 6 hours. The reaction mixture was treated with water and EA, and organic phase was separated. Organic phase was washed with water, dried over Na$_2$SO$_4$, and was concentrated to dryness. The crude material was purified by a column chromatography (200-300 mesh silica gel, DCM/MeOH=40/1) to afford 2-(3-(3,4-dihydroisoquinolin-2(1H)-yl)-2-hydroxypropyl)-4,4-dimethyl-7-(oxetan-3-ylamino)-3,4-dihydroisoquinolin-1(2H)-one (15) (60 mg, 20% yield) as a yellow solid. $^1$HNMR (400 MHz, DMSO-d$_6$) δ (ppm) 6.99-7.11 (m, 6H), 6.64-6.66 (m, 1H), 6.42-6.44 (m, 1H), 4.81-4.84 (m, 2H), 4.71-4.72 (m, 1H), 4.45-4.52 (m, 1H), 4.37-4.40 (m, 2H), 4.02 (brs, 1H), 3.73-3.80 (m, 1H), 3.61 (s, 2H), 3.32-3.41 (m, 2H), 3.15-3.21 (m, 1H), 2.71-2.80 (m, 4H), 2.49-2.51 (m, 2H), 1.20 (s, 6H); LC-MS (m/z): 436 [M+H]$^+$.

Example 4: 6-(3-(3,4-dihydroisoquinolin-2(1H)-yl)-2-hydroxypropyl)-3-(oxetan-3-ylamino)-7,8-dihydro-1,6-naphthyridin-5(6H)-one (16)

(16)

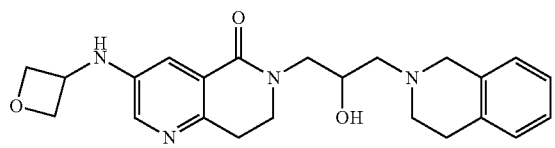

Step 1: tert-butyl 3-bromo-7,8-dihydro-1,6-naphthyridine-6(5H)-carboxylate

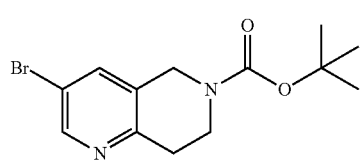 [SMILES: CC(C)(C)OC(=O)N1CCc2ncc(Br)cc2C1]

To a stirred solution of 3-bromo-5,6,7,8-tetrahydro-1,6-naphthyridine (5.00 g, 23.4 mmol, 1.0 eq.) and Di-tert-butyl pyrocarbonate (Boc$_2$O, 6.14 g, 28.1 mmol, 1.2 eq.) in dichloromethane (50 ml) was added triethylamine (2.30 g, 23.4 mmol, 1.0 eq.), and the resultant mixture was stirred at ambient temperature overnight. The reaction mixture was concentrated to dryness, and the crude material was purified by a column chromatography (200-300 mesh silica gel, PE/EA=5/1) to afford tert-butyl3-bromo-7,8-dihydro-1,6-naphthyridine-6(5H)-carboxylate (5.50 g, 75% yield) as a colorless oil. 1HNMR (400 MHz, CDCl$_3$) δ (ppm) 8.48 (d, 1H), 7.57 (d, 1H), 4.59 (s, 2H), 3.75 (t, 2H), 2.96 (t, 2H), 1.50 (s, 9H).

Step 2: tert-butyl 3-bromo-5-oxo-7,8-dihydro-1,6-naphthyridine-6(5H)-carboxylate

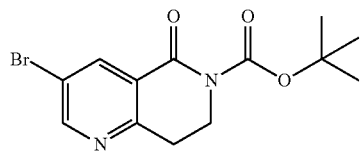 [SMILES: CC(C)(C)OC(=O)N1CCc2ncc(Br)cc2C1=O]

To a stirred mixture of RuCl$_3$ (0.40 g, 1.91 mmol, 0.15 eq.) and NaIO$_4$ (12.84 g, 60.0 mmol, 4.7 eq.) in H$_2$O/EA (80 ml/80 ml) was added a solution of tert-butyl 3-bromo-7,8-dihydro-1,6-naphthyridine-6(5H)-carboxylate (4.00 g, 12.8 mmol, 1.0 eq.) in EA (40 ml), and the resultant mixture was stirred at ambient temperature overnight. Organic phase was separated, washed with brine, dried over Na$_2$SO$_4$, and was concentrated to dryness. The crude material was purified by a column chromatography (200-300 mesh silica gel, PE/EA=5/1) to afford tert-butyl 3-bromo-5-oxo-7,8-dihydro-1,6-naphthyridine-6(5H)-carboxylate (3.70 g, 84% yield) as a white solid. $^1$HNMR (400 MHz, CDCl$_3$) δ (ppm) 8.71 (d, 1H), 8.54 (d, 1H), 4.07 (t, 2H), 3.17 (t, 2H), 1.59 (s, 9H).

Step 3: 3-bromo-7,8-dihydro-1,6-naphthyridin-5(6H)-one

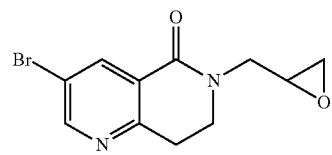 [SMILES: O=C1c2cc(Br)cnc2CCN1CC1CO1]

To a solution of tert-butyl 3-bromo-5-oxo-7,8-dihydro-1,6-naphthyridine-6(5H)-carboxylate (4.40 g, 13.4 mmol, 1.0 eq.) in dichloromethane (60 ml) was added Trifluoroacetic acid (TFA, 20 ml), and the resultant mixture was stirred at ambient temperature for 3 hours. The reaction mixture was concentrated to dryness, and was treated with water. The resultant aqueous solution was treated with 15% NaOH until pH=9-10 was achieved, and was filtered to collect precipitate. The obtained solid was dried to afford 3-bromo-7,8-dihydro-1,6-naphthyridin-5(6H)-one (2.60 g, 86% yield) as a light yellow solid.

Step 4: 3-bromo-6-(oxiran-2-ylmethyl)-7,8-dihydro-1,6-naphthyridin-5(6H)-one

To a stirred solution of 3-bromo-7,8-dihydro-1,6-naphthyridin-5(6H)-one (1.12 g, 4.93 mmol, 1.0 eq.) in DMF (20 ml) was added NaH (60% in oil, 0.24 g, 5.92 mmol, 1.5 eq.), and the resultant mixture was stirred at ambient temperature for 30 min. 2-(chloromethyl)-oxirane (0.68 g, 7.40 mmol, 1.5 eq.) was added, and the resultant mixture was heated to 80° C. for additional 3 hours. The reaction was quenched with water, and was extracted with EA. Organic phase was washed with water twice, followed by brine, dried over Na$_2$SO$_4$, and was concentrated to dryness. The obtained crude 3-bromo-6-(oxiran-2-ylmethyl)-7,8-dihydro-1,6-naphthyridin-5(6H)-one was used directly in next step without further purification.

Step 5: 3-bromo-6-(3-(3,4-dihydroisoquinolin-2 (1H)-yl)-2-hydroxypropyl)-7,8-dihydro-1,6-naphthyridin-5(6H)-one (I-2)

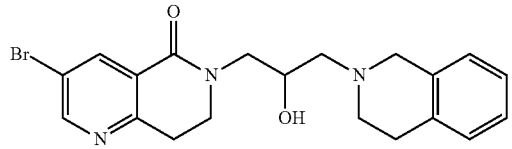

(I-2)

To a solution of crude 3-bromo-6-(oxiran-2-ylmethyl)-7,8-dihydro-1,6-naphthyridin-5(6H)-one in ethanol (25 ml) was added 1,2,3,4-tetrahydroisoquinoline (1.97 g, 14.79 mmol, 3.0 eq.), and the resultant mixture was heated to reflux for 5 hours. The reaction mixture was concentrated to dryness, and the crude material was purified by a column chromatography (200-300 mesh silica gel, DCM/MeOH=50/1) to afford 3-bromo-6-(3-(3,4-dihydroisoquinolin-2(1H)-yl)-2-hydroxy propyl)-7,8-dihydro-1,6-naphthyridin-5(6H)-one (1.00 g, 50% yield over two steps) as a light yellow oil.

Step 6: 6-(3-(3,4-dihydroisoquinolin-2(1H)-yl)-2-hydroxypropyl)-3-(oxetan-3-ylamino)-7,8-dihydro-1,6-naphthyridin-5(6H)-one (16)

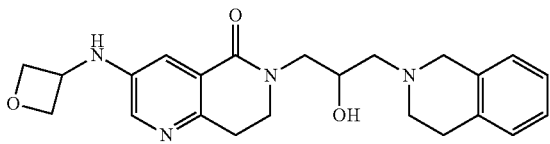 [SMILES: O=C1c2cc(NC3COC3)cnc2CCN1CC(O)CN1CCc2ccccc2C1]

A mixture of 3-bromo-6-(3-(3,4-dihydroisoquinolin-2 (1H)-yl)-2-hydroxypropyl)-7,8-dihydro-1,6-naphthyridin-5 (6H)-one (I-2) (200 mg, 0.48 mmol, 1.0 eq.), oxetan-3-amine (175 mg, 2.40 mmol, 5.0 eq.), Cs$_2$CO$_3$ (469 mg, 1.44 mmol, 3.0 eq.), catalytic amount of XantPhos and catalytic amount of Pd$_2$(dba)$_3$ in 1,4-dioxane (20 mL) was heated to reflux under nitrogen gas atmosphere for 5 hours. The reaction mixture was treated with water and EA, and organic phase was separated. Organic phase was washed with water, dried over Na$_2$SO$_4$, and was concentrated to dryness. The crude material was purified by a column chromatography (200-300 mesh silica gel, DCM/MeOH=20/1) to afford 6-(3-(3,4-dihydroisoquinolin-2(1H)-yl)-2-hydroxypropyl)-3-(oxetan-3-ylamino)-7,8-dihydro-1,6-naphthyridin-5(6H)-one (16) (50 mg, 25% yield) as a yellow powder. $^1$HNMR (400 MHz, DMSO-d$_6$) δ (ppm) 7.91 (d, J=2.8 Hz, 1H), 7.21 (d, J=2.8 Hz, 1H), 7.03-7.10 (m, 4H), 6.69 (d, J=6.6 Hz, 1H), 4.83-4.87 (m, 3H), 4.55-4.60 (m, 1H), 4.39 (t, J=6.0 Hz, 1H), 4.03 (brs, 1H), 3.60-3.77 (m, 5H), 3.22-3.27 (m, 1H), 2.80-2.92 (m, 6H), 2.49-2.50 (m, 2H); LC-MS (m/z): 409 [M+H]$^+$.

Example 5: 2-(3-(3,4-dihydroisoquinolin-2(1H)-yl)-2-hydroxypropyl)-3-methyl-7-(oxetan-3-ylamino)-3,4-dihydroisoquinolin-1(2H)-one (21)

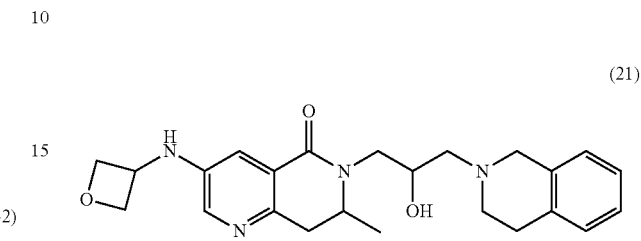

(21)

Step 1: 1-bromo-4-(2-nitroprop-1-en-1-yl)benzene

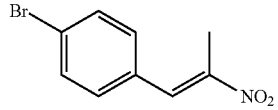

To a stirred mixture of 4-bromobenzaldehyde (41.00 g, 222 mmol, 1.0 eq.), nitromethane (66.54 g, 886 mmol, 4.0 eq.) and formic acid (44.96 g, 977 mmol, 4.4 eq.) was added 2-aminoethan-1-ol (42.04 g, 688 mmol, 3.1 eq.) at an ice-water bath temperature, and the resultant mixture was heated to 60° C. for 4 hours. The reaction mixture was pooled into cold water (500 ml), and the obtained mixture was stirred for additional 10 min. Solid was collected by filtration, washed with water, and was dried to afford 1-bromo-4-(2-nitroprop-1-en-1-yl)benzene (40.82 g, 76% yield) as a yellow solid. $^1$HNMR (400 MHz, CDCl$_3$) δ (ppm) 8.02 (s, 1H), 7.60 (d, J=8.3 Hz, 2H), 7.31 (d, J=8.3 Hz, 2H), 2.44 (s, 3H).

Step 2: 1-(4-bromophenyl)propan-2-amine

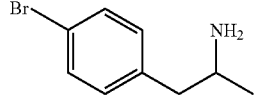

To a stirred suspension of NaBH$_4$ (10.78 g, 285 mmol, 4.6 eq.) in THF (100 ml) was added dropwise a solution of BH$_3$/THF (1.0N, 345 ml, 345 mmol, 5.5 eq.) at an ice-water bath temperature, followed by drowise addition of a solution of 1-bromo-4-(2-nitroprop-1-en-1-yl) benzene (15.00 g, 62.0 mmol, 1.0 eq.) in THF (100 ml), and the resultant mixture was heated to 65° C. for 6 hours. The reaction mixture was slowly added to cold water, and was extracted with DCM. Organic phase was dried over Na$_2$SO$_4$, and was concentrated to dryness. The resultant residue was dissolved in methanol with conc. HCl (aq), and the mixture was heated to reflux for additional 2 hours. The reaction mixture was concentrated to dryness, and was treated with water. The mixture was treated with 1 N NaOH until pH=9-10 was achieved, and was extracted with DCM. Organic phase was dried over Na$_2$SO$_4$, and was concentrated to dryness. The resultant residue was used directly in next step without further purification.

Step 3: methyl (1-(4-bromophenyl)propan-2-yl)carbamate

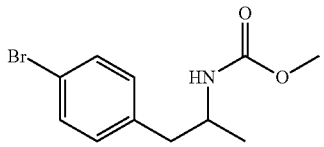

To a stirred solution of crude 1-(4-bromophenyl)propan-2-amine (5.60 g, 26.0 mmol, 1.0 eq.) and triethylamine (3.95 g, 39.0 mmol, 1.5 eq.) in DMF (50 ml) was added methyl carbonochloridate (3.70 g, 39.0 mmol, 1.5 eq.) at an ice-water bath temperature, and the resultant mixture was stirred at ambient temperature for 4 hours. The reaction mixture was pooled into cold water, and was extracted with DCM. Organic phase was dried over Na$_2$SO$_4$, and was concentrated to dryness. The residue was purified by a column chromatography to afford methyl (1-(4-bromophenyl) propan-2-yl)carbamate (3.00 g, 18% yield) as a light yellow solid. $^1$H NMR (400 MHz, CDCl$_3$) δ (ppm) 7.42 (d, J=8.0 Hz, 2H), 7.06 (d, J=8.0 Hz, 2H), 4.51 (brs, 1H), 3.94 (brs, 1H), 3.65 (s, 3H), 2.63-2.81 (m, 2H), 1.11 (d, J=6.6 Hz, 3H).

Step 4: 7-bromo-3-methyl-3,4-dihydroisoquinolin-1(2H)-one

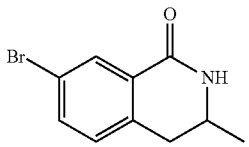

A mixture of methyl (1-(4-bromophenyl) propan-2-yl) carbamate (3.00 g, 11.0 mmol, 1.0 eq.) in TfOH (30 ml) was heated to 100° C. for 10 hours. The reaction mixture was cooled to ambient temperature, and was poured into cold water. Solid was collected by filtration, washed with tert-Butyl methyl ether (TBME), dried to afford 7-bromo-3-methyl-3,4-dihydroisoquinolin-1(2H)-one (1.00 g, 38 yield) as a light yellow solid. $^1$HNMR (400 MHz, DMSO-d$_6$) δ (ppm) 8.08 (s, 1H), 7.90 (s, 1H), 7.66 (d, J=8.1 Hz, 1H), 7.27 (d, J=8.1 Hz, 1H), 3.66-3.71 (m, 1H), 2.93 (dd, J=4.3, 15.8 Hz, 1H), 2.62 (dd, J=10.1, 15.8 Hz, 1H), 1.17 (d, J=6.6 Hz, 3H).

Step 5: 2-(3-(3,4-dihydroisoquinolin-2(1H)-yl)-2-hydroxypropyl)-3-methyl-7-(oxetan-3-ylamino)-3,4-dihydroisoquinolin-1(2H)-one (21)

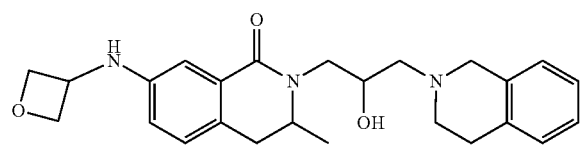 [SMILES: CC1Cc2ccc(NC3COC3)cc2C(=O)N1CC(O)CN1CCc2ccccc2C1]

Using a synthetic method similar to that for compound 15 in Example 3, 2-(3-(3,4-dihydroisoquinolin-2(1H)-yl)-2-hydroxypropyl)-3-methyl-7-(oxetan-3-ylamino)-3,4-dihydroisoquinolin-1(2H)-one (21) was obtained as a yellowish solid. $^1$HNMR (400 MHz, DMSO-d$_6$) δ (ppm) 6.97-7.08 (m, 6H), 6.58 (d, J=7.8 Hz, 1H), 6.41 (d, J=7.8 Hz, 1H), 4.81-4.84 (m, 3H), 4.50-4.51 (m, 1H), 4.38-4.41 (m, 2H), 3.84-4.13 (m, 3H), 3.56-3.67 (m, 2H), 3.07-3.21 (m, 2H), 2.72-2.79 (m, 5H), 2.47-2.50 (m, 2H), 0.99 (t, J=6.8 Hz, 3H); LC-MS (m/z): 422 [M+H]$^+$.

Example 6: (R)-7-((1-acetylpiperidin-4-yl)amino)-2-(3-(3,4-dihydroisoquinolin-2(1H)-yl)-2-hydroxypropyl)-3,4-dihydroisoquinolin-1(2H)-one (24a) and (S)-7-((1-acetyl piperidin-4-yl)amino)-2-(3-(3,4-dihydroisoquinolin-2(1H)-yl)-2-hydroxypropyl)-3,4-dihydroisoquinolin-1(2H)-one (24b)

(24a)

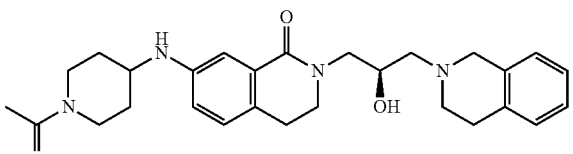

(24b)

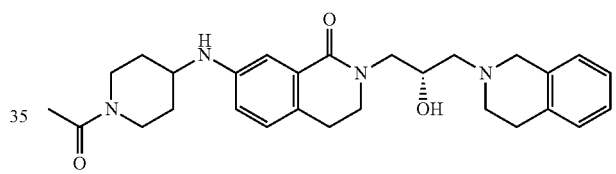

Step 1: 7-bromo-2-(2-((tert-butyldimethylsilyl)oxy)-3-(3,4-dihydroisoquinolin-2(1H)-yl)propyl)-3,4-dihydroisoquinolin-1(2H)-one

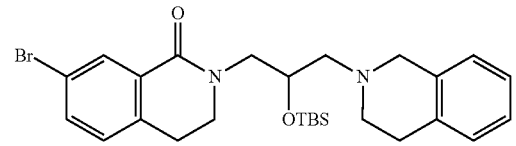 [SMILES: CC(C)(C)[Si](C)(C)OC(CN1CCc2ccccc2C1)CN1CCc2ccc(Br)cc2C1=O]

To a stirred solution of 7-bromo-2-(3-(3,4-dihydroisoquinolin-2(1H)-yl)-2-hydroxypropyl)-3,4-dihydroisoquinolin-1(2H)-one (I-1) (12.00 g, 29.0 mmol, 1.0 eq) and imidazole (5.92 g, 35.0 mmol, 3.0 eq) in DMF (120 ml) was added solid tert-Butyl(chloro) dimethylsilane (TBSCl, 5.23 g, 35.0 mmol, 1.2 eq) in portions, and the resultant mixture was stirred at ambient temperature overnight. The reaction mixture was diluted with cold water, and was extracted with EA. Organic phase was washed with water twice followed by brine, dried over MgSO$_4$, and was concentrated to dryness. The residue was purified by column chromatography to afford 7-bromo-2-(2-((tert-butyldimethylsilyl)oxy)-3-(3,4-dihydro isoquinolin-2(1H)-yl)propyl)-3,4-dihydroisoquinolin-1(2H)-one (10.00 g, 67% yield) as a light yellow oil.

Step 2: 7-((1-acetylpiperidin-4-yl)amino)-2-(2-((tert-butyldimethylsilyl)oxy)-3-(3,4-dihydro isoquinolin-2(1H)-yl)propyl)-3,4-dihydroisoquinolin-1(2H)-one

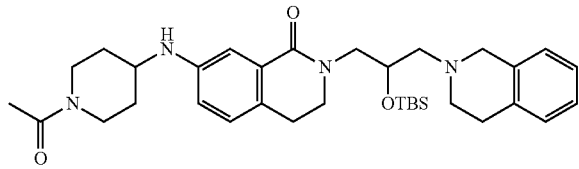 [SMILES: CC(=O)N1CCC(Nc2ccc3c(c2)C(=O)N(CC(CN2CCc4ccccc4C2)O[Si](C)(C)C(C)(C)C)CC3)CC1]

To a stirred solution of 7-bromo-2-(2-((tert-butyldimethylsilyl)oxy)-3-(3,4-dihydro isoquinolin-2(1H)-yl)propyl)-3,4-dihydroisoquinolin-1(2H)-one (1.00 g, 1.89 mmol, 1.0 eq) in 1,4-dioxane (20 ml) was added 1-(4-aminopiperidin-1-yl)ethan-1-one (1.10 g, 7.74 mmol, 4.1 eq), solid $Cs_2CO_3$ (1.83 g, 5.67 mmol, 3.0 eq), catalytic $Pd_2(dba)_3$ and Xant-Phos, and the resultant mixture was heated to reflux under nitrogen gas atmosphere for 3 hours. The reaction mixture was concentrated to dryness, and the residue was treated with water/EA. Organic phase was dried over $MgSO_4$, and was concentrated to dryness. The residue was purified by column chromatography (DCM/MeOH=20/1-10/1) to afford 7-((1-acetylpiperidin-4-yl)amino)-2-(2-((tert-butyldimethylsilyl)oxy)-3-(3,4-dihydroisoquinolin-2(1H)-yl)propyl)-3,4-dihydroisoquinolin-1(2H)-one (0.51 g, 46% yield) as a yellow solid.

Step 3: (R)-7-((1-acetylpiperidin-4-yl)amino)-2-(3-(3,4-dihydroisoquinolin-2(1H)-yl)-2-hydroxy propyl)-3,4-dihydroisoquinolin-1(2H)-one (24a) and (S)-7-((1-acetyl piperidin-4-yl)amino)-2-(3-(3,4-dihydroisoquinolin-2(1H)-yl)-2-hydroxypropyl)-3,4-dihydroisoquinolin-1(2H)-one (24b)

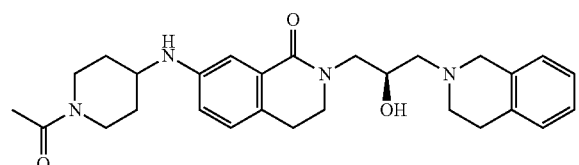

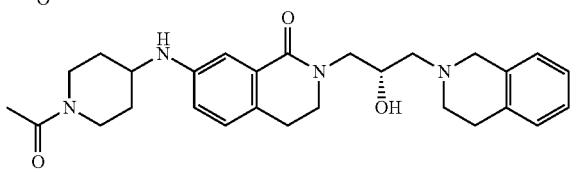

To a stirred solution of 7-((1-acetylpiperidin-4-yl)amino)-2-(2-((tert-butyldimethyl silyl)oxy)-3-(3,4-dihydroisoquinolin-2(1H)-yl)propyl)-3,4-dihydroisoquinolin-1(2H)-one (0.51 g, 0.86 mmol, 1.0 eq) in MeOH (10 ml) was added Tetrabutylammonium fluoride hydrate (TBAF, 0.54 g, 1.73 mmol, 2.0 eq), and the resultant mixture was stirred at ambient temperature overnight. The reaction mixture was concentrated to dryness, and the obtained residue was purified by column chromatography to afford 7-((1-acetylpiperidin-4-yl)amino)-2-(3-(3,4-dihydroisoquinolin-2(1H)-yl)-2-hydroxypropyl)-3,4-dihydroisoquinolin-1(2H)-one. The racemate was subjected to chiral SFC to separated two enantiomers 24a and 24b. $^1$H NMR (400 MHz, DMSO-$d_6$) δ (ppm) 6.96-7.12 (m, 6H), 6.70 (d, J=6.5 Hz, 1H), 5.57 (d, J=8.1 Hz, 1H), 4.79 (brs, 1H), 4.18-4.21 (m, 1H), 4.01 (brs, 1H), 3.75-3.78 (m, 2H), 3.46-3.62 (m, 5H), 3.15-3.23 (m, 2H), 2.72-2.80 (m, 7H), 2.50 (m, 2H), 1.99 (s, 3H), 1.84-1.93 (m, 2H), 1.29-1.33 (m, 2H); LC-MS (m/z): 477 [M+H]$^+$.

Preparative separation method: Instrument: waters SFC200; Column: DAICEL ChiralPak OD, 250×30 mm I.D., 5 μm; Mobile phase: A for CO2 and B for methanol (0.1% NH3H2O); Gradient: B 30%; Flow rate: 80 mL/min; Back pressure: 100 bar; Column temperature: 38° C.; Wavelength: 220 nm; Cycle time: 20 min.

Example 7: (R)-4-(3-(3,4-dihydroisoquinolin-2(1H)-yl)-2-hydroxypropyl)-7-(pyridazin-4-ylamino)-3,4-dihydrobenzo[f][1,4]oxazepin-5 (2H)-one (30a) and (S)-4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (30b)

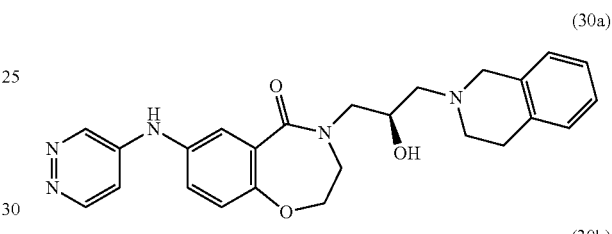

(30a)

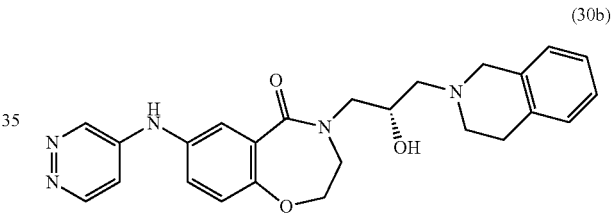

(30b)

Step 1: 7-bromo-4-(3-(3,4-dihydroisoquinolin-2(1H)-yl)-2-hydroxypropyl)-3,4-dihydrobenzo[f][1,4]oxazepin-5(2H)-one

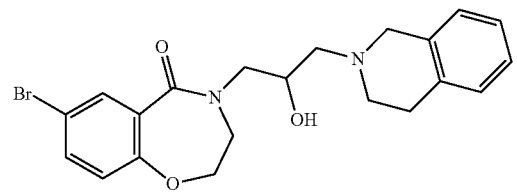 [SMILES: O=C1c2cc(Br)ccc2OCCN1CC(O)CN1CCc2ccccc2C1]

To a stirred suspension of NaH (60%, 1.20 g, 29.9 mmol, 1.2 eq) in DMF (50 ml) was added 7-bromo-3,4-dihydrobenzo[f][1,4]oxazepin-5(2H)-one (6.00 g, 25.0 mmol, 1.0 eq) at an ice-water bath temperature, and the reaction mixture was stirred at same temperature for 1 hour. 2-(chloromethyl)-oxirane (3.47 g, 37.0 mmol, 1.5 eq) was added, and the obtained mixture was heated to 90° C. for additional 3 hours. The reaction mixture was poured into cold water, and extracted with EA. Organic phase was washed with water twice followed by brine, dried over $MgSO_4$, and concentrated to dryness. The residue was dissolved in ethanol (100 ml), and 1,2,3,4-tetrahydroisoquinoline (5.27 g, 46.6 mmol, 2.0 eq) was added. The resultant mixture was heated to reflux for 1 hour. The reaction was concentrated to dryness, and was purified by column chromatography to afford 7-bromo-4-(3-(3,4-dihydroisoquinolin-2(1H)-yl)-2-hydroxy propyl)-3,4-dihydrobenzo[f][1,4]oxazepin-5(2H)-one (4.30 g, 43% yield) as a yellow oil. ¹HNMR (400 MHz, DMSO-d₆) δ (ppm) 7.74 (d, J=2.4 Hz, 1H), 7.60 (dd, J=2.4 Hz, 8.6 Hz, 1H), 6.96-7.09 (m, 5H), 4.87 (br, 1H), 4.40 (t, J=4.5 Hz, 2H), 4.02 (q, J=6.9 Hz, 1H), 3.87 (dd, J=3.3 Hz, 13.5 Hz, 1H), 3.62 (m, 4H), 3.25-3.33 (m, 3H), 2.71-2.80 (m, 4H), 2.47-2.49 (m, 2H).

Step 2: (R)-4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (30a) and (S)-4-(3-(3,4-dihydro isoquinolin-2(1H)-yl)-2-hydroxypropyl)-7-(pyridazin-4-ylamino)-3,4-dihydrobenzo[f][1,4]oxazepin-5(2H)-one (30b)

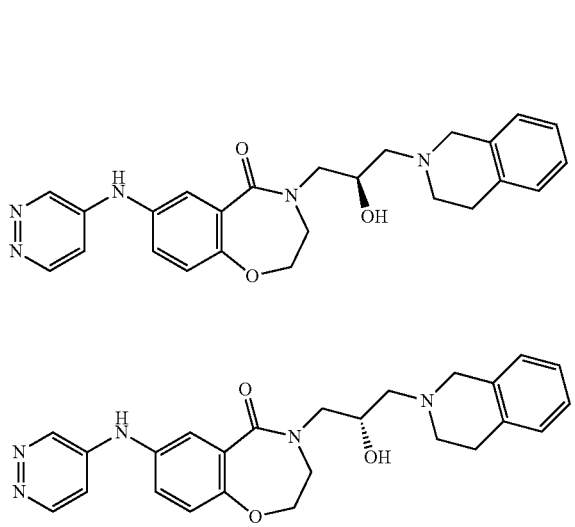

To a stirred solution of 7-bromo-4-(3-(3,4-dihydroisoquinolin-2(1H)-yl)-2-hydroxypropyl)-3,4-dihydrobenzo[f][1,4]oxazepin-5(2H)-one (1.51 g, 3.5 mmol, 1.0 eq) in 1,4-dioxane (20 ml) was added pyridazin-4-amine (1.00 g, 10.5 mmol, 3.0 eq), solid Cs₂CO₃ (3.42 g, 10.5 mmol, 3.0 eq), catalytic Pd₂(dba)₃ and XantPhos, and the resultant mixture was heated to reflux under nitrogen gas atmosphere for 5 hours. The reaction mixture was concentrated to dryness, and the residue was treated with water/EA. Organic phase was dried over MgSO₄, and was concentrated to dryness. The residue was purified by column chromatography (DCM/MeOH=50/1-20/1) to afford 4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (300 mg, 20% yield) as a light yellow powder. The racemate was subjected to chiral SFC to separated two enantiomers 30a and 30b. ¹HNMR (400 MHz, DMSO-d₆) δ (ppm) 9.11 (s, 1H), 8.79 (d, J=2.4 Hz, 1H), 8.64 (d, J=6.1 Hz, 1H), 7.45 (d, J=2.8 Hz, 1H), 7.34 (dd, J=2.8 Hz, 8.6, 1H), 7.03-7.11 (m, 5H), 6.97 (dd, J=3.0 Hz, 6.1, 1H), 4.87 (d, J=4.9 Hz, 1H), 4.38 (t, J=4.9 Hz, 1H), 4.01-4.06 (m, 1H), 3.89 (dd, J=3.6 Hz, 13.6, 1H), 3.64 (m, 3H), 3.34 (m, 2H), 2.71-2.83 (m, 4H), 2.50 (m, 2H); LC-MS (m/z): 446 [M+H]⁺.

Preparative separation method: Instrument: waters SFC200; Column: DAICEL ChiralPak OD, 250×50 mm I.D., 10 μm; Mobile phase: A for CO₂ and B for ethanol (0.1% NH₃H₂O); Gradient: B 40%; Flow rate: 60 ml/min; Back pressure: 100 bar; Column temperature: 38° C.; Wavelength: 210 nm; Cycle time: 50 min.

Example 8: 3-(3-(3,4-dihydroisoquinolin-2(1H)-yl)-2-hydroxypropyl)-6-(oxetan-3-ylamino)quinazolin-4(3H)-one (3)

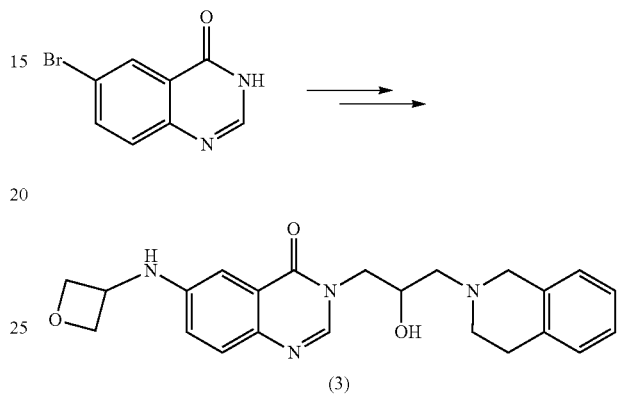

Compound (3) was synthesized in a method similar to that for compound 1 in Example 1, using 6-bromo-3,4-dihydroquinazolin-4-one as starting material. ¹HNMR (400 MHz, DMSO-d₆) δ (ppm) 7.98 (s, 1H), 7.45 (d, J=8.8 Hz, 1H), 7.04-7.12 (m, 5H), 6.92-6.95 (m, 2H), 5.06 (d, J=5.5 Hz, 1H), 4.88-4.91 (m, 2H), 4.59-4.62 (m, 1H), 4.35-4.45 (m, 3H), 4.04-4.06 (m, 1H), 3.55-3.69 (m, 3H), 2.68-2.82 (m, 4H), 2.53-2.55 (m, 2H); LC-MS (m/z): 407 [M+H]⁺.

Example 9: 2-(3-(3,4-dihydroisoquinolin-2(1H)-yl)-2-hydroxypropyl)-7-(oxetan-3-ylamino)isoquinolin-1(2H)-one (4)

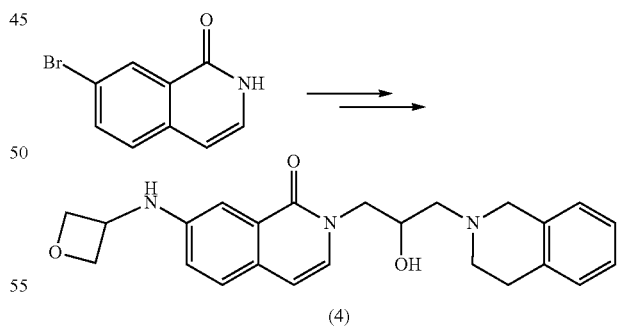

Compound 4 was synthesized in a method similar to that for compound 1 in Example 1, using 7-bromo-1,2-dihydroisoquinolin-1-one as starting material. ¹HNMR (400 MHz, DMSO-d₆) δ (ppm) 7.41 (d, J=8.6 Hz, 1H), 7.00-7.12 (m, 7H), 6.79 (d, J=6.2 Hz, 1H), 6.41 (d, J=7.3 Hz, 1H), 4.88-4.91 (m, 3H), 4.59-4.63 (m, 1H), 4.44 (t, J=6.0 Hz, 1H), 4.36 (dd, J=3.2 Hz, 13.2 Hz, 1H), 4.10 (brs, 1H), 3.53-3.69 (m, 3H), 2.69-2.83 (m, 4H), 2.50-2.52 (m, 2H); LC-MS (m/z): 406 [M+H]⁺.

Example 10: 6-chloro-2-(3-(3,4-dihydroisoquinolin-2(1H)-yl)-2-hydroxypropyl)-7-((1-methyl-1H-pyrazol-4-yl)amino)-3,4-dihydroisoquinolin-1(2H)-one (26)

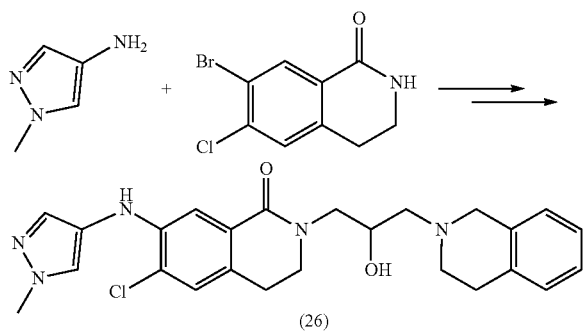

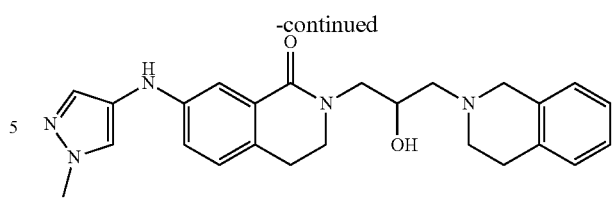

Compound 26 was synthesized in a method similar to that for compound 1 in Example 1, using 7-bromo-6-chloro-1,2,3,4-tetrahydroisoquinolin-1-one and 1-methyl-1H-pyrazol-4-amine as starting material. ¹HNMR (400 MHz, DMSO-d₆) δ (ppm) 7.66 (s, 1H), 7.35 (s, 1H), 7.25 (s, 2H), 7.02-7.09 (m, 5H), 4.79 (brs, 1H), 4.00-4.03 (m, 1H), 3.84 (s, 3H), 3.72-3.76 (m, 1H), 3.54-3.64 (m, 4H), 3.13-3.18 (m, 1H), 2.71-2.82 (m, 6H), 2.45-2.49 (m, 2H); LC-MS (m/z): 466 [M+H]⁺.

Example 11: (R)-2-(3-(3,4-dihydroisoquinolin-2(1H)-yl)-2-hydroxypropyl)-7-((1-methyl-1H-pyrazol-4-yl)amino)-3,4-dihydroisoquinolin-1(2H)-one (12a) and (S)-2-(3-(3,4-dihydro isoquinolin-2(1H)-yl)-2-hydroxypropyl)-7-((1-methyl-1H-pyrazol-4-yl)amino)-3,4-dihydroisoquinolin-1(2H)-one (12b)

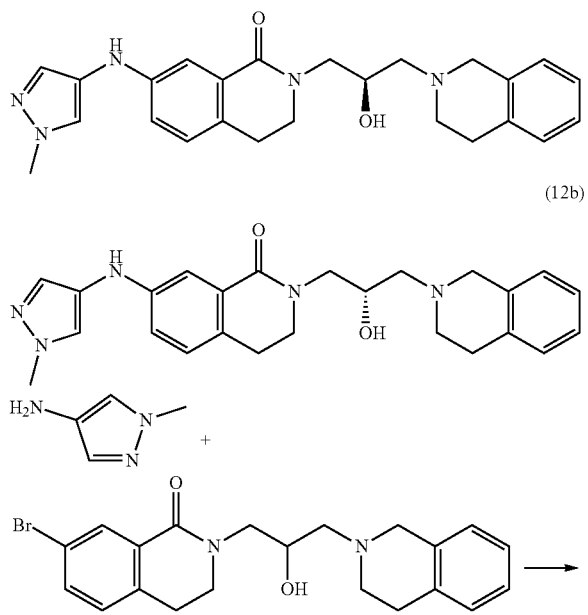

Compound 12a and 12b was synthesized in a method similar to that for compound 30a and 30b in Example 7, using 7-bromo-2-(3-(3,4-dihydroisoquinolin-2(1H)-yl)-2-hydroxypropyl)-3,4-dihydroisoquinolin-1(2H)-one (I-1) and 1-methyl-1H-pyrazol-4-amine as starting material. ¹HNMR (400 MHz, DMSO-d₆) δ (ppm) 7.60 (s, 1H), 7.53 (s, 1H), 7.26-7.28 (m, 2H), 7.01-7.10 (m, 5H), 6.83-6.86 (m, 1H), 4.81 (brs, 1H), 4.02 (brs, 1H), 3.78 (s, 3H), 3.74-3.77 (m, 1H), 3.52-3.65 (m, 5H), 3.18-3.24 (m, 2H), 2.67-2.81 (m, 6H), 2.50-2.51 (m, 2H); LC-MS (m/z): 432 [M+H]⁺.

Example 12: (R)-2-(3-(3,4-dihydroisoquinolin-2(1H)-yl)-2-hydroxypropyl)-7-(pyridazin-4-ylamino)-3,4-dihydroisoquinolin-1(2H)-one (28a) and (S)-2-(3-(3,4-dihydro isoquinolin-2(1H)-yl)-2-hydroxypropyl)-7-(pyridazin-4-ylamino)-3,4-dihydroisoquinolin-1(2H)-one (28b)

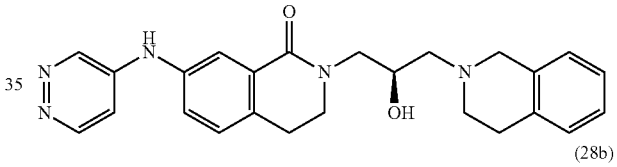

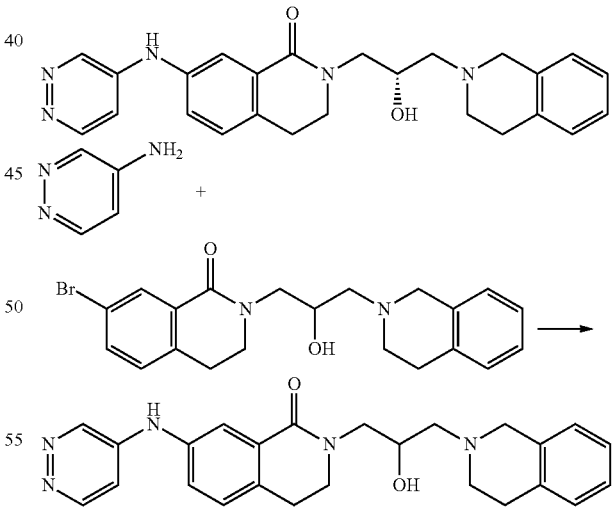

Compound 28a and 28b was synthesized in a method similar to that for compound 30a and 30b in Example 7, using 7-bromo-2-(3-(3,4-dihydroisoquinolin-2(1H)-yl)-2-hydroxypropyl)-3,4-dihydroisoquinolin-1(2H)-one (I-1) and pyridazin-4-amine as starting material. ¹HNMR (400 MHz, DMSO-d₆) δ (ppm) 9.22 (s, 1H), 8.81 (d, J=2.9 Hz, 1H), 8.68 (d, J=6.1 Hz, 1H), 7.70 (d, J=2.2 Hz, 1H), 7.29-7.37 (m, 2H), 7.02-7.10 (m, 5H), 4.83 (d, J=5.0 Hz, 1H), 4.05 (m, 1H), 3.77-3.82 (m, 1H), 3.61-3.72 (m, 4H), 3.24-3.29 (m, 2H), 2.92-2.99 (m, 2H), 2.69-2.80 (m, 5H); LC-MS (m/z): 430 [M+H]+.

Example 13: (R)-4-(3-(3,4-dihydroisoquinolin-2(1H)-yl)-2-hydroxypropyl)-7-((1-methyl-1H-pyrazol-4-yl)amino)-3,4-dihydrobenzo[f][1,4]oxazepin-5(2H)-one (29a) and (S)-4-(3-(3,4-dihydroisoquinolin-2(1H)-yl)-2-hydroxypropyl)-7-((1-methyl-1H-pyrazol-4-yl)amino)-3,4-dihydrobenzo[f][1,4]oxazepin-5(2H)-one (29b)

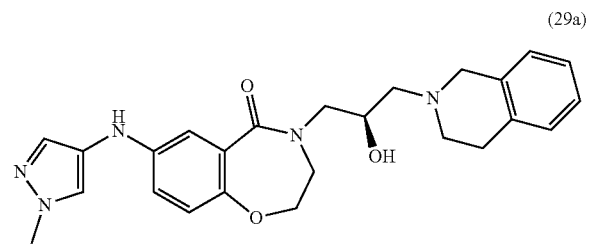

(29a)

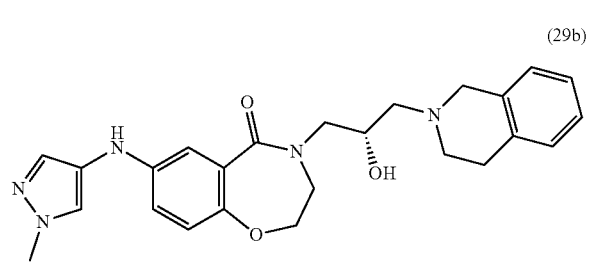

(29b)

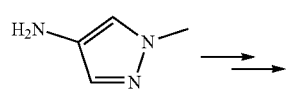

Compound 29a and 29b was synthesized in a method similar to that for compound 30a and 30b in Example 7, using 1-methyl-1H-pyrazol-4-amine as starting material. 1H NMR (400 MHz, DMSO-d6) δ (ppm) 7.59 (s, 1H), 7.44 (s, 1H), 7.27 (s, 1H), 7.02-7.09 (m, 4H), 6.81-6.90 (m, 3H), 4.84 (s, 1H), 4.20-4.22 (m, 2H), 3.99-4.03 (m, 1H), 3.79-2.87 (m, 4H), 3.62 (s, 2H), 3.51-3.52 (m, 1H), 3.21-3.27 (m, 2H), 2.72-2.80 (m, 4H), 2.55 (m, 2H); LC-MS (m/z): 448 [M+H]+.

Example 14: (R)-7-bromo-4-(3-(3,4-dihydroisoquinolin-2(1H)-yl)-2-hydroxypropyl)-3,4-dihydrobenzo[f][1,4]oxazepin-5(2H)-one and (S)-7-bromo-4-(3-(3,4-dihydroisoquinolin-2(1H)-yl)-2-hydroxypropyl)-3,4-dihydrobenzo[f][1,4]oxazepin-5(2H)-one

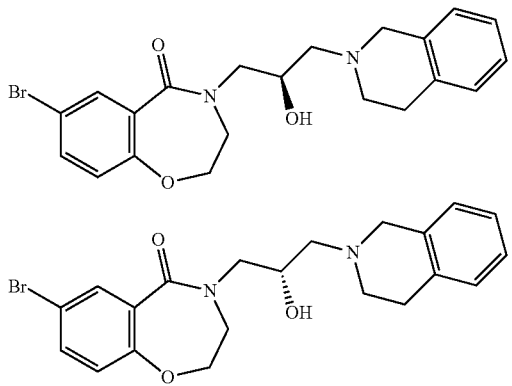

Two enantiomers were separated by chiral SFC in following method, and absolute configuration of each enantiomer was confirmed by Mosher's method.

Analytical separation method: Instrument: waters UPLC; Column: Daicel Chiralcel IC, 2.1×150 mm I.D., 3 μm; Mobile phase: A for CO2 and B for ethanol (0.1% DEA); Gradient: B 30%; Flow rate: 1 mL/min; Back pressure: 1500 psi; Column temperature: 40° C.; Wavelength: 220 nm.

Preparative separation method: Instrument: waters SFC200; Column: Daicel Chiralcel IC, 250×30 mm I.D., 5 μm; Mobile phase: A for CO2 and B for ethanol (0.1% NH3H2O); Gradient: B 35%; Flow rate: 70 mL/min; Back pressure: 100 bar; Column temperature: 38° C.; Wavelength: 210 nm; Cycle time: 14 min.

Example 15: 7-((1-acetylazetidin-3-yl)amino)-2-(3-(3,4-dihydroisoquinolin-2(1H)-yl)-2-hydroxypropyl)-3,4-dihydroisoquinolin-1(2H)-one (6)

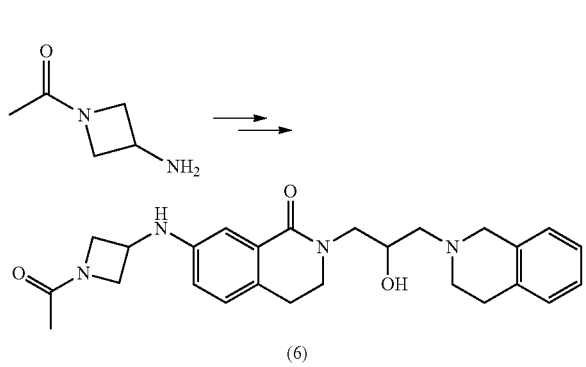

(6)

Compound 6 was synthesized in a method similar to that for compound 1 in Example 1, using 1-(3-aminoazetidin-1-yl)ethan-1-one as starting material. LC-MS (m/z): 449 [M+H]+.

Example 16: 7-(cyclobutylamino)-2-(3-(3,4-dihydroisoquinolin-2(1H)-yl)-2-hydroxypropyl)-3,4-dihydroisoquinolin-1(2H)-one (7)

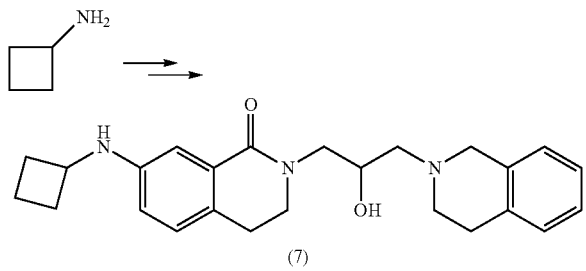

Compound 7 was synthesized in a method similar to that for compound 1 in Example 1, using cyclobutanamine as starting material. LC-MS (m/z): 407 [M+H]$^+$.

Example 17: (S)-2-(3-(3,4-dihydroisoquinolin-2(1H)-yl)-2-hydroxypropyl)-7-((1-(methylsulfonyl)azetidin-3-yl)amino)-3,4-dihydroisoquinolin-1(2H)-one (8)

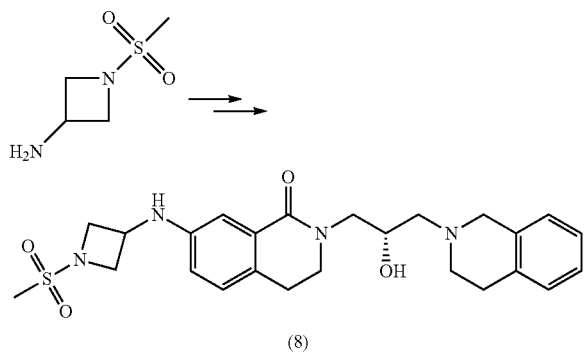

Compound 8 was synthesized in a method similar to that for compound 1 in Example 1, using 1-methanesulfonylazetidin-3-amine and (S)-7-bromo-2-(3-(3,4-dihydroisoquinolin-2(1H)-yl)-2-hydroxypropyl)-3,4-dihydroisoquinolin-1(2H)-one as starting material. $^1$HNMR (400 MHz, DMSO-d$_6$) δ (ppm) 7.02-7.09 (m, 6H), 6.65 (d, J=6.2 Hz, 1H), 6.37 (d, J=6.8 Hz, 1H), 4.82 (brs, 1H), 4.16-4.26 (m, 3H), 4.03 (brs, 1H), 3.53-3.79 (m, 7H), 3.19-3.25 (m, 1H), 3.03 (s, 3H), 2.72-2.97 (m, 6H), 2.48-2.49 (m, 2H); LC-MS (m/z): 485 [M+H]$^+$.

Example 18: (S)-2-(3-(3,4-dihydroisoquinolin-2(1H)-yl)-2-hydroxypropyl)-7-((1-methylazetidin-3-yl)amino)-3,4-dihydroisoquinolin-1(2H)-one (9)

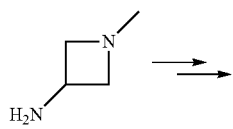

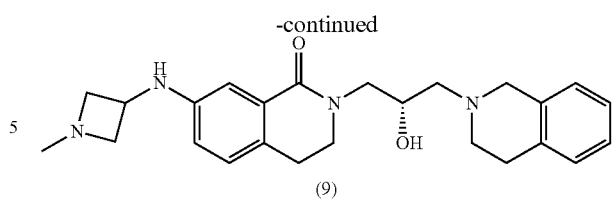

Compound 9 was synthesized in a method similar to that for compound 1 in Example 1, using 1-methylazetidin-3-amine and (S)-7-bromo-2-(3-(3,4-dihydroisoquinolin-2(1H)-yl)-2-hydroxypropyl)-3,4-dihydroisoquinolin-1(2H)-one as starting material. LC-MS (m/z): 421 [M+H]$^+$.

Example 19: 2-((S)-3-(3,4-dihydroisoquinolin-2(1H)-yl)-2-hydroxypropyl)-7-(((S)-tetrahydrofuran-3-yl)amino)-3,4-dihydroisoquinolin-1(2H)-one (10)

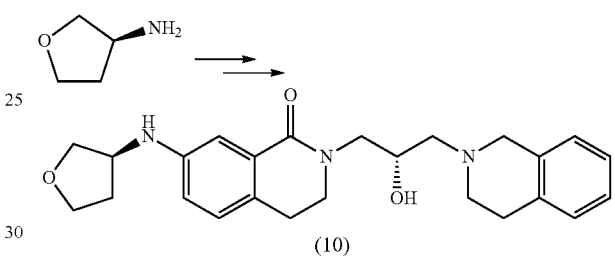

Compound 10 was synthesized in a method similar to that for compound 1 in Example 1, using (3S)-oxolan-3-amine and (S)-7-bromo-2-(3-(3,4-dihydroisoquinolin-2(1H)-yl)-2-hydroxypropyl)-3,4-dihydroisoquinolin-1(2H)-one as starting material. $^1$HNMR (400 MHz, DMSO-d$_6$) δ (ppm) 6.98-7.10 (m, 6H), 6.68 (dd, J=2.4 Hz, 8.1 Hz, 1H), 5.89 (d, J=6.3 Hz, 1H), 4.83 (brs, 1H), 3.96-4.02 (m, 2H), 3.57-3.89 (m, 9H), 3.21-3.24 (m, 1H), 2.73-2.80 (m, 6H), 2.48-2.50 (m, 2H), 2.13-2.18 (m, 1H), 1.65-1.74 (m, 1H); LC-MS (m/z): 422 [M+H]$^+$.

Example 20: 2-((S)-3-(3,4-dihydroisoquinolin-2(1H)-yl)-2-hydroxypropyl)-7-(((R)-tetrahydrofuran-3-yl)amino)-3,4-dihydroisoquinolin-1(2H)-one (11)

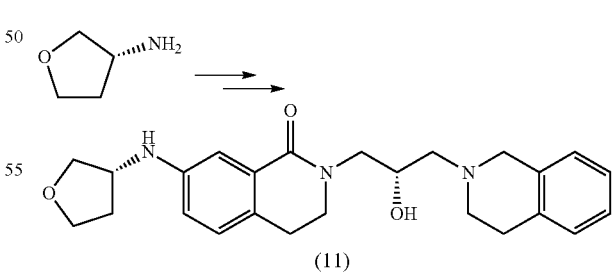

Compound 11 was synthesized in a method similar to that for compound 1 in Example 1, using (3R)-oxolan-3-amine and (S)-7-bromo-2-(3-(3,4-dihydroisoquinolin-2(1H)-yl)-2-hydroxypropyl)-3,4-dihydroisoquinolin-1(2H)-one as starting material. $^1$H NMR (400 MHz, DMSO-d$_6$) δ (ppm) 6.98-7.10 (m, 6H), 6.68 (dd, J=2.4 Hz, 8.2 Hz, 1H), 5.89 (d, J=6.4 Hz, 1H), 4.82 (brs, 1H), 3.96-4.02 (m, 2H), 3.49-3.89

(m, 9H), 3.21-3.24 (m, 1H), 2.73-2.80 (m, 6H), 2.48-2.50 (m, 2H), 2.13-2.18 (m, 1H), 1.73-1.74 (m, 1H); LC-MS (m/z): 422 [M+H]⁺.

Example 21: 2-(3-(3,4-dihydroisoquinolin-2(1H)-yl)-2-hydroxypropyl)-7-((1-(oxetan-3-yl)-1H-pyrazol-4-yl)amino)-3,4-dihydroisoquinolin-1(2H)-one (22)

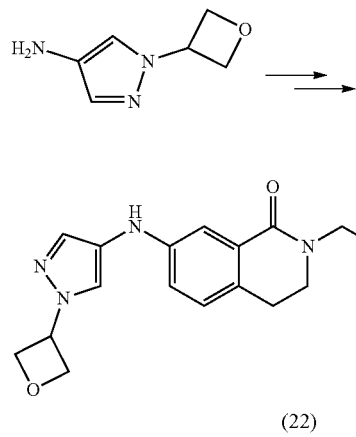

(22)

Compound 22 was synthesized in a method similar to that for compound 1 in Example 1, using 1-(oxetan-3-yl)-1H-pyrazol-4-amine as starting material. ¹HNMR (400 MHz, DMSO-d₆) δ (ppm) 7.80 (s, 1H), 7.65 (s, 1H), 7.47 (s, 1H), 7.31 (s, 1H), 7.04-7.09 (m, 5H), 6.90 (s, 1H), 5.54 (brs, 1H), 4.80-4.91 (m, 5H), 4.03 (brs, 1H), 3.62-3.75 (m, 5H), 3.24-3.33 (m, 2H), 2.72-2.80 (m, 5H), 2.50 (brs, 2H); LC-MS (m/z): 474 [M+H]⁺.

Example 22: 2-(3-(3,4-dihydroisoquinolin-2(1H)-yl)-2-hydroxypropyl)-7-((1-methyl-1H-pyrazol-3-yl)amino)-3,4-dihydroisoquinolin-1(2H)-one (23)

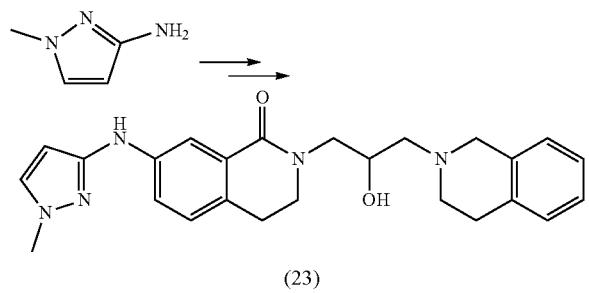

(23)

Compound 23 was synthesized in a method similar to that for compound 1 in Example 1, using 1-methyl-1H-pyrazol-3-amine as starting material. ¹HNMR (400 MHz, DMSO-d₆) δ (ppm) 8.45 (s, 1H), 7.79 (s, 1H), 7.59 (m, 2H), 7.10 (m, 5H), 5.75 (s, 1H), 4.85 (brs, 1H), 4.05 (brs, 1H), 3.65-3.74 (m, 8H), 3.34 (m, 1H), 2.82 (m, 6H), 2.51 (m, 2H); LC-MS (m/z): 432 [M+H]⁺.

Example 23: 2-(3-(3,4-dihydroisoquinolin-2(1H)-yl)-2-hydroxypropyl)-7-((1-(tetrahydro-2H-pyran-4-yl)-1H-pyrazol-4-yl)amino)-3,4-dihydroisoquinolin-1(2H)-one (25)

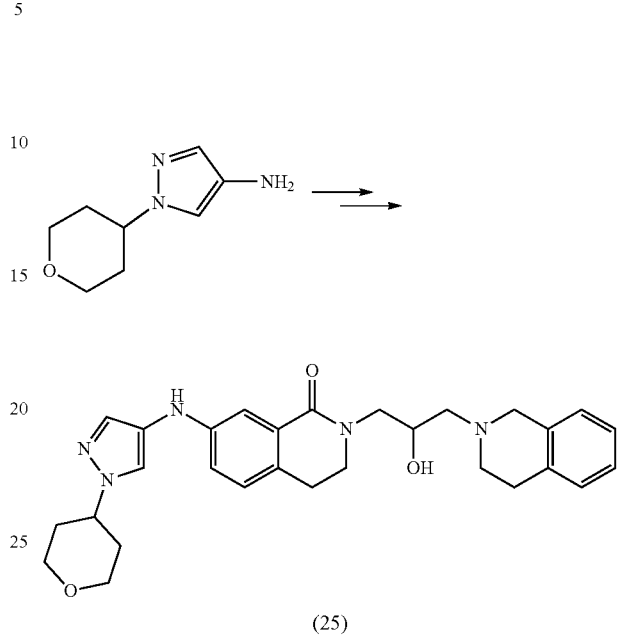

(25)

Compound 25 was synthesized in a method similar to that for compound 1 in Example 1, using 1-(oxan-4-yl)-1H-pyrazol-4-amine as starting material. ¹HNMR (400 MHz, DMSO-d₆) δ (ppm) 7.69 (s, 1H), 7.54 (s, 1H), 7.33 (s, 1H), 7.28 (s, 1H), 7.02-7.08 (m, 5H), 6.85-6.86 (m, 1H), 4.81 (brs, 1H), 4.34 (brs, 1H), 3.94-4.01 (m, 3H), 3.73-3.76 (m, 1H), 3.45-3.63 (m, 6H), 3.22-3.23 (m, 1H), 2.72-2.79 (m, 6H), 2.49 (m, 2H), 1.95 (brs, 4H); LC-MS (m/z): 502 [M+H]⁺.

Example 24: 2-(3-(3,4-dihydroisoquinolin-2(1H)-yl)-2-hydroxypropyl)-7-((1-methyl-2-oxo-1,2-dihydropyridin-4-yl)amino)-3,4-dihydroisoquinolin-1(2H)-one (27)

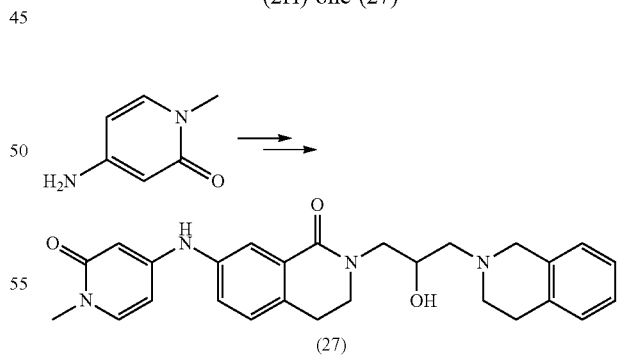

(27)

Compound 27 was synthesized in a method similar to that for compound 1 in Example 1, using 4-amino-1-methyl-1,2-dihydropyridin-2-one as starting material. ¹H NMR (400 MHz, DMSO-d₆) δ (ppm) 8.73 (s, 1H), 7.68 (s, 1H), 7.45 (d, J=7.4 Hz, 1H), 7.06-7.26 (m, 6H), 5.89-5.91 (m, 1H), 5.72 (s, 1H), 4.94 (brs, 1H), 4.09 (brs, 1H), 3.59-3.79 (m, 5H), 3.26-3.29 (m, 4H), 2.79-2.94 (m, 7H), 2.50-2.58 (m, 1H); LC-MS (m/z): 459 [M+H]⁺.

Example 25: 6-(3-(3,4-dihydroisoquinolin-2(1H)-yl)-2-hydroxypropyl)-3-((tetrahydro-2H-pyran-4-yl)amino)-7,8-dihydro-1,6-naphthyridin-5(6H)-one (18)

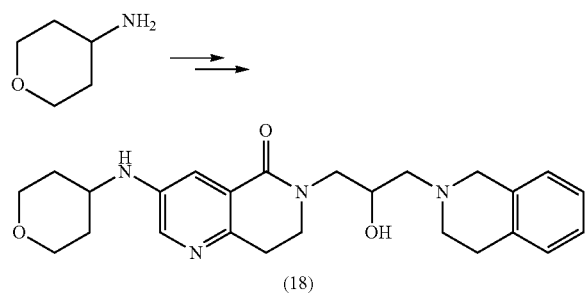

(18)

Compound 18 was synthesized in a method similar to that for compound 16 in Example 4, using oxan-4-amine as starting material. $^1$HNMR (400 MHz, DMSO-d$_6$) δ (ppm) 8.59 (s, 1H), 8.16 (s, 1H), 8.01 (s, 1H), 7.35 (m, 4H), 4.85 (brs, 1H), 4.04 (brs, 2H), 3.30-3.76 (m, 10H), 2.72-3.08 (m, 6H), 2.50 (brs, 2H), 1.85 (brm, 2H), 1.36 (brs, 2H); LC-MS (m/z): 437 [M+H]$^+$.

Example 26: 3-((1-acetylpiperidin-4-yl)amino)-6-(3-(3,4-dihydroisoquinolin-2(1H)-yl)-2-hydroxypropyl)-7,8-dihydro-1,6-naphthyridin-5(6H)-one (19)

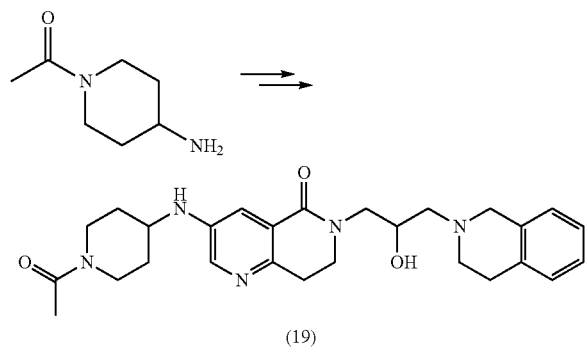

(19)

Compound 19 was synthesized in a method similar to that for compound 16 in Example 4, using 1-(4-aminopiperidin-1-yl)ethan-1-one as starting material. LC-MS (m/z): 478 [M+H]$^+$.

Example 27: 6-(3-(3,4-dihydroisoquinolin-2(1H)-yl)-2-hydroxypropyl)-3-((1-methyl-1H-pyrazol-4-yl)amino)-7,8-dihydro-1,6-naphthyridin-5(6H)-one (20)

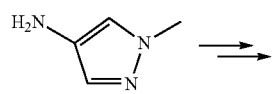

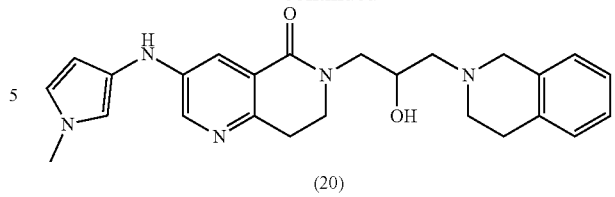

(20)

Compound 20 was synthesized in a method similar to that for compound 16 in Example 4, using 1-methyl-1H-pyrazol-4-amine as starting material. $^1$HNMR (400 MHz, DMSO-d$_6$) δ (ppm) 8.11 (d, J=2.9 Hz, 1H), 7.68 (s, 1H), 7.44 (d, J=2.8 Hz, 1H), 7.32 (s, 1H), 7.01-7.12 (m, 5H), 4.81 (d, J=4.9 Hz, 1H), 3.91-4.01 (m, 1H), 3.77 (s, 3H), 3.63-3.75 (m, 4H), 3.20-3.25 (m, 1H), 3.00-3.02 (m, 1H), 2.90-2.94 (m, 2H), 2.67-2.80 (m, 4H), 2.46-2.50 (m, 2H); LC-MS (m/z): 433 [M+H]$^+$.

Example 28: 4-(3-(3,4-dihydroisoquinolin-2(1H)-yl)-2-hydroxypropyl)-7-(oxetan-3-ylamino)-3,4-dihydrobenzo[f][1,4]oxazepin-5(2H)-one (5)

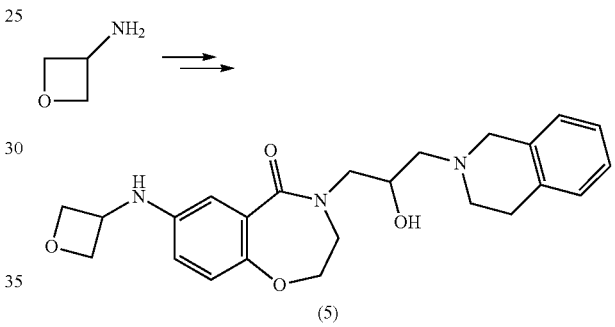

(5)

Compound 5 was synthesized in a method similar to that for compound 30a and 30b in Example 7, using oxetan-3-amine as starting material. $^1$HNMR (400 MHz, DMSO-d$_6$) δ (ppm) 7.03-7.12 (m, 4H), 6.80 (d, J=8.6 Hz, 1H), 6.64 (d, J=2.8 Hz, 1H), 6.56 (dd, J=2.8 Hz, 8.6 Hz, 1H), 6.33 (d, J=6.6 Hz, 1H), 4.81-4.84 (m, 3H), 4.46-4.51 (m, 1H), 4.37-4.40 (m, 2H), 4.19-4.22 (m, 2H), 4.00-4.04 (m, 1H), 3.86 (dd, J=3.5 Hz, 13.6 Hz, 1H), 3.51-3.57 (m, 2H), 3.50-3.51 (m, 1H), 3.22-3.28 (m, 1H), 2.73-2.81 (m, 4H), 2.50 (m, 2H); LC-MS (m/z): 424 [M+H]$^+$.

Example 29: (S)-2-(3-(3,4-dihydroisoquinolin-2(1H)-yl)-2-hydroxypropyl)-7-(1-methyl-1H-pyrazol-4-yl)-3,4-dihydroisoquinolin-1(2H)-one (13)

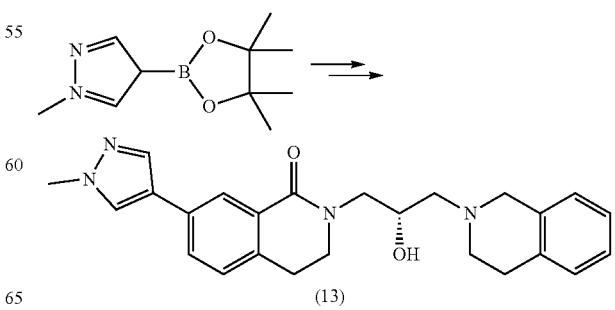

(13)

Compound 13 was synthesized in a method similar to that for compound 14 in Example 2, using 1-methyl-4-(4,4,5,5-tetramethyl-1,3,2-dioxaborolan-2-yl)-1H-pyrazole and (S)-7-bromo-2-(3-(3,4-dihydroisoquinolin-2(1H)-yl)-2-hydroxypropyl)-3,4-dihydroisoquinolin-1 (2H)-one as starting material. $^1$HNMR (400 MHz, DMSO-$d_6$) δ (ppm) 8.18 (s, 1H), 8.01 (s, 1H), 7.87 (s, 1H), 7.65 (dd, J=1.7 Hz, 7.8 Hz, 1H), 7.26 (d, J=7.9 Hz, 1H), 5.76 (brs, 1H), 4.86 (brs, 1H), 3.81-3.87 (m, 4H), 3.60-3.72 (m, 4H), 3.23-3.28 (m, 1H), 2.91-2.95 (m, 2H), 2.71-2.81 (m, 4H), 2.50-2.51 (m, 2H); LC-MS (m/z): 417 [M+H]$^+$.

Example 30: 3-(3-(3,4-dihydroisoquinolin-2(1H)-yl)-2-hydroxypropyl)-6-(pyridazin-4-ylamino)quinazolin-4(3H)-one (31)

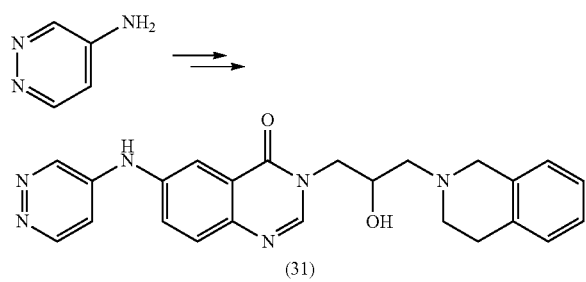

(31)

Compound 31 was synthesized in a method similar to that for compound 3 in Example 8, using pyridazin-4-amine as starting material. $^1$HNMR (400 MHz, DMSO-$d_6$) δ (ppm) 9.48 (s, 1H), 8.90 (d, J=2.4 Hz, 1H), 8.76 (d, J=6.1 Hz, 1H), 8.20 (s, 1H), 7.92 (s, 1H), 7.69 (s, 2H), 7.18 (dd, J=3.0 Hz, 6.1 Hz, 1H), 7.03-7.12 (m, 4H), 5.11 (d, J=5.5 Hz, 1H), 4.39 (dd, J=3.0 Hz, 13.4 Hz, 1H), 4.09-4.10 (m, 1H), 3.59-3.71 (m, 3H), 2.67-2.81 (m, 4H), 2.57-2.58 (m, 2H); LC-MS (m/z): 429 [M+H]$^+$.

Example 31: 2-(3-(3,4-dihydroisoquinolin-2(1H)-yl)-2-hydroxypropyl)-7-(pyridazin-4-ylamino)isoquinolin-1(2H)-one (32)

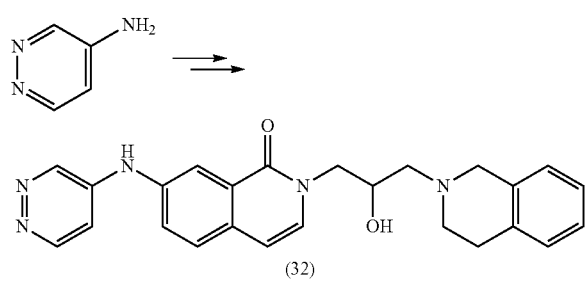

(32)

Compound 32 was synthesized in a method similar to that for compound 4 in Example 9, using pyridazin-4-amine as starting material. $^1$HNMR (400 MHz, DMSO-$d_6$) δ (ppm) 9.48 (s, 1H), 8.90 (d, J=2.4 Hz, 1H), 8.73 (d, J=6.1 Hz, 1H), 8.02 (d, J=2.3 Hz, 1H), 7.68 (d, J=8.6 Hz, 1H), 7.59 (dd, J=2.4 Hz, 8.5 Hz, 1H), 7.34 (d, J=7.4 Hz, 1H), 7.15 (dd, J=3.0 Hz, 6.1 Hz, 1H), 7.03-7.12 (m, 4H), 6.58 (d, J=7.4 Hz, 1H), 4.95 (d, J=5.5 Hz, 1H), 4.39 (dd, J=3.0 Hz, 13.4 Hz, 1H), 4.13 (m, 1H), 3.57-3.70 (m, 3H), 2.73-2.83 (m, 4H), 2.54-2.55 (m, 2H); LC-MS (m/z): 428 [M+H]$^+$.

Example 32: 2-(3-(3,4-dihydroisoquinolin-2(1H)-yl)-2-hydroxypropyl)-7-(pyridazin-4-ylamino)phthalazin-1(2H)-one (33)

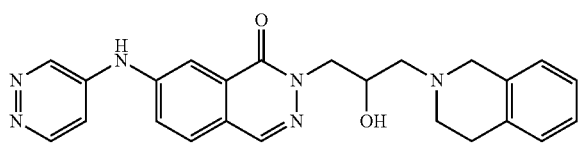

(33)

Step 1: 3,6-dibromoisobenzofuran-1(3H)-one

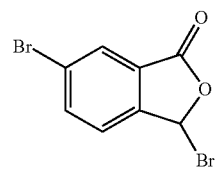 [SMILES: O=C1OC(Br)c2ccc(Br)cc21]

To a stirred solution of 6-bromoisobenzofuran-1(3H)-one (2.00 g, 9.40 mmol, 1.0 eq) in chloroform (20 ml) was added N-Bromosuccinimide (NBS, 1.92 g, 10.8 mmol, 1.15 eq) and 2,2'-Azobis(2-methylpropionitrile) (AIBN, 154 mg, 0.94 mmol, 0.1 eq), and the resultant mixture was heated to 60° C. for 2.5 hours. The reaction mixture was washed with saturated NaHCO$_3$ followed by brine, dried over MgSO$_4$, and was concentrated to dryness. The residue was purified by column chromatography (PE/EtOAc=10/1) to afford 3,6-dibromoisobenzofuran-1(3H)-one (2.00 g, 73% yield) as a white solid.

Step 2: 7-bromophthalazin-1(2H)-one

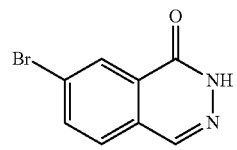

To a stirred solution of 3,6-dibromoisobenzofuran-1(3H)-one (2.00 g, 6.85 mmol, 1.0 eq) in ethanol (20 ml) was added hydrazine hydrate (85%, 1.71 g, 34.2 mmol, 5.0 eq) at ice-water bath temperature, and the resultant mixture was heated to reflux for 2 hours. The reaction mixture was cooled to ambient temperature, and was diluted with cold water. Precipitate was collected by filtration to afford 7-bromophthalazin-1(2H)-one (1.50 g, 97% yield) as white solid.

Step 3: 7-bromo-2-(oxiran-2-ylmethyl)phthalazin-1(2H)-one

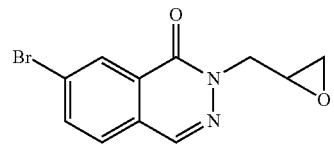 [SMILES: O=c1c2cc(Br)ccc2cnn1CC1CO1]

To a stirred solution of 7-bromophthalazin-1(2H)-one (1.00 g, 4.44 mmol, 1.0 eq) in DMF (10 ml) was added 2-(chloromethyl)-oxirane (1.24 g, 13.3 mmol, 3.0 eq) and Cs₂CO₃ (4.35 g, 13.3 mmol, 3.0 eq), and the resultant mixture was heated to 90° C. for 0.5 hour. The reaction mixture was diluted with cold water, and was extracted with EA. Organic phase was washed with water twice followed by brine, dried over MgSO₄, and was concentrated to dryness. The obtained residue was used directly in next step without further purification.

Step 4: 7-bromo-2-(3-(3,4-dihydroisoquinolin-2 (1H)-yl)-2-hydroxypropyl)phthalazin-1(2H)-one

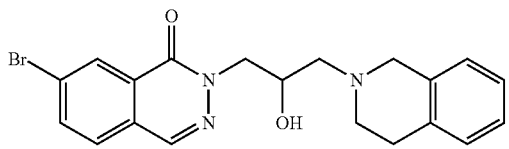 [SMILES: O=c1c2cc(Br)ccc2cnn1CC(O)CN1CCc2ccccc2C1]

To a stirred solution of 7-bromo-2-(oxiran-2-ylmethyl) phthalazin-1(2H)-one (1.25 g, 4.44 mmol, 1.0 eq) in ethanol (20 ml) was added 1,2,3,4-tetrahydroisoquinoline (0.89 g, 6.66 mmol, 1.5 eq), and the resultant mixture was heated to reflux for 4 hours. The reaction mixture was concentrated to dryness, and the residue was purified by column chromatography (DCM/MeOH=100/1-50/1) to afford 7-bromo-2-(3-(3,4-dihydroisoquinolin-2(1H)-yl)-2-hydroxy propyl) phthalazin-1(2H)-one (1.00 g, 56% yield) as light yellow oil.

Step 5: 2-(3-(3,4-dihydroisoquinolin-2(1H)-yl)-2-hydroxypropyl)-7-(pyridazin-4-ylamino)phthalazin-1 (2H)-one (33)

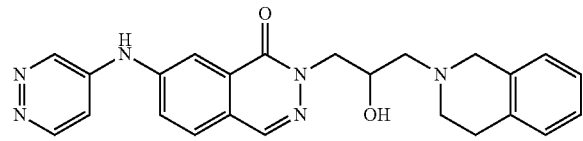 [SMILES: O=c1c2cc(Nc3ccnnc3)ccc2cnn1CC(O)CN1CCc2ccccc2C1]

Compound 33 was synthesized in a method similar to that for compound 1 in Example 1, using pyridazin-4-amine and 7-bromo-2-(3-(3,4-dihydroisoquinolin-2(1H)-yl)-2-hydroxypropyl) phthalazin-1(2H)-one as starting material. ¹H NMR (400 MHz, DMSO-d₆) δ (ppm) 9.74 (s, 1H), 8.98 (d, J=2.7 Hz, 1H), 8.85 (d, J=6.0 Hz, 1H), 8.34 (s, 1H), 7.95 (d, J=2.1 Hz, 1H), 7.90 (d, J=8.6 Hz, 1H), 7.74 (dd, J=2.3 Hz, 8.6 Hz, 1H), 7.33 (dd, J=3.0 Hz, 6.1 Hz, 1H), 7.00-7.08 (m, 4H), 4.84 (d, J=5.0 Hz, 1H), 4.12-4.28 (m, 3H), 3.60 (m, 2H), 2.57-2.74 (m, 6H); LC-MS (m/z): 429 [M+H]⁺.

Example 33: 2-(3-(3,4-dihydroisoquinolin-2(1H)-yl)-2-hydroxypropyl)-4,4-dimethyl-7-(pyridazin-4-ylamino)-3,4-dihydroisoquinolin-1(2H)-one (34)

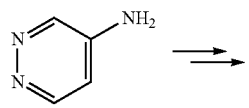

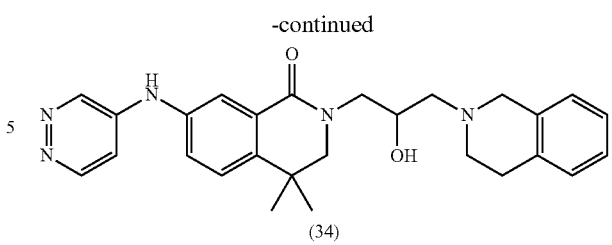

Compound 34 was synthesized in a method similar to that for compound 15 in Example 3, using pyridazin-4-amine as starting material. ¹HNMR (400 MHz, DMSO-d₆) δ (ppm) 9.24 (s, 1H), 8.82 (d, J=2.4 Hz, 1H), 8.68 (d, J=6.1 Hz, 1H), 7.73 (s, 1H), 7.41 (s, 2H), 7.02-7.11 (m, 5H), 4.76 (d, J=4.0 Hz, 1H), 4.04-4.06 (m, 1H), 3.82 (dd, J=4.2 Hz, 13.5 Hz, 1H), 3.64 (s, 2H), 3.53 (d, J=12.6 Hz, 1H), 3.42 (d, J=12.6 Hz, 1H), 3.24-3.29 (m, 1H), 2.73-2.81 (m, 4H), 2.55 (m, 2H), 1.28 (s, 6H); LC-MS (m/z): 458 [M+H]⁺.

Example 34: 2'-(3-(3,4-dihydroisoquinolin-2(1H)-yl)-2-hydroxypropyl)-7'-(pyridazin-4-ylamino)-2',3'-dihydro-1'H-spiro[cyclopropane-1,4'-isoquinolin]-1'-one (35)

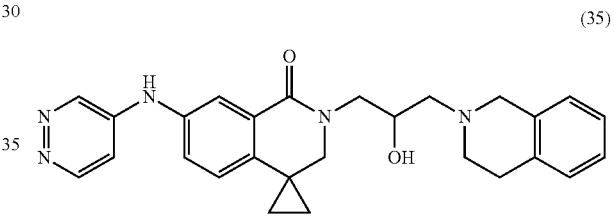

Step 1: (1-(4-bromophenyl)cyclopropyl)methanamine

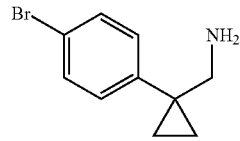 [SMILES: NCC1(c2ccc(Br)cc2)CC1]

To a stirred solution of 1-(4-bromophenyl)cyclopropane-1-carbonitrile (1.00 g, 4.50 mmol, 1.0 eq) in toluene (10 ml) was added solution of BH₃ in THF (1 N, 22.5 mmol, 5.0 eq) at ice-water bath temperature, and the resultant mixture was heated to reflux for 4 hours. The reaction mixture was concentrated to dryness, and was treated with methanol. The resultant mixture was heated to reflux for additional 0.5 hour. The reaction mixture was concentrated to dryness, and was treated with DCM and water. Organic phase was separated, washed with water, dried over MgSO₄, and was concentrated to dryness. The residue was purified by column chromatography (DCM/MeOH=20/1) to afford (1-(4-bromophenyl)cyclopropyl)methanamine (0.70 g, 69% yield) as a light yellow oil.

Step 2: methyl 2-((((1-(4-bromophenyl)cyclopropyl)methyl)carbamoyl)oxy)benzoate

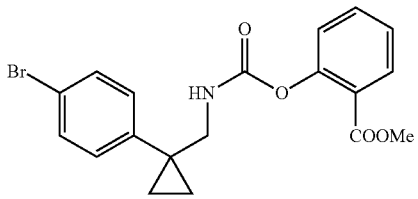 [SMILES: COC(=O)c1ccccc1OC(=O)NCC1(c2ccc(Br)cc2)CC1]

To a stirred solution of (1-(4-bromophenyl)cyclopropyl) methanamine (0.70 g, 3.10 mmol, 1.2 eq) in THF (10 ml) was added dimethyl 2,2'-(carbonylbis(oxy))dibenzoate (0.85 g, 2.58 mmol, 1.0 eq), and the resultant mixture was stirred at ambient temperature for 5 hours. The reaction mixture was concentrated to dryness, and the residue was purified by column chromatography (PE/EA=5/1-3/1) to afford methyl 2-((((1-(4-bromophenyl)cyclopropyl)methyl) carbamoyl) oxy)benzoate (1.00 g, 96% yield) as colorless oil.

Step 3: 7'-bromo-2',3'-dihydro-1'H-spiro[cyclopropane-1,4'-isoquinolin]-1'-one

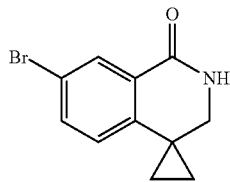 [SMILES: O=C1NCC2(CC2)c2ccc(Br)cc21]

To a stirred solution of 2-((((1-(4-bromophenyl)cyclopropyl)methyl)carbamoyl)oxy) benzoate (1.00 g, 2.47 mmol, 1.0 eq) in DCM (20 ml) was added TfOH (1.81 g, 12.4 mmol, 5.0 eq) at ice-water bath temperature, and the resultant mixture was stirred for additional 0.5 hour. The reaction mixture was diluted with water, and was treated with saturated Na$_2$CO$_3$ until pH=7-8 was achieved. The mixture was extracted with DCM, dried over MgSO$_4$, and was concentrated to dryness. The residue was purified by column chromatography (PE/EA=1/1) to afford 7'-bromo-2',3'-dihydro-1'H-spiro[cyclopropane-1,4'-isoquinolin]-1'-one (285 mg, 46% yield) as white solid.

Step 4: 2'-(3-(3,4-dihydroisoquinolin-2(1H)-yl)-2-hydroxypropyl)-7'-(pyridazin-4-ylamino)-2',3'-dihydro-1'H-spiro[cyclopropane-1,4'-isoquinolin]-1'-one (35)

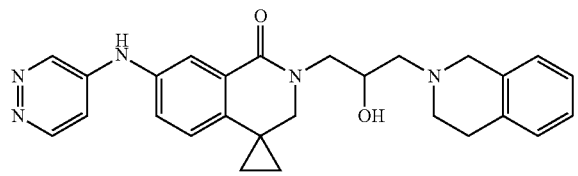

(35)

Compound 35 was synthesized in a method similar to that for compound 15 in Example 3, using pyridazin-4-amine as starting material. $^1$H NMR (400 MHz, DMSO-d$_6$) δ (ppm) 9.21 (s, 1H), 8.81 (d, J=2.6 Hz, 1H), 8.68 (d, J=6.1 Hz, 1H), 7.75 (d, J=2.4 Hz, 1H), 7.34 (dd, J=2.4 Hz, 8.3 Hz, 1H), 7.02-7.11 (m, 6H), 4.79 (d, J=4.5 Hz, 1H), 4.04-4.06 (m, 1H), 3.81 (dd, J=4.1 Hz, 13.6 Hz, 1H), 3.64 (s, 2H), 3.52 (dd, J=12.8 Hz, 38.4 Hz, 2H), 3.21-3.27 (m, 1H), 2.73-2.81 (m, 4H), 2.50 (m, 2H), 1.03 (d, J=4.7 Hz, 4H); LC-MS (m/z): 456 [M+H]$^+$.

Example 35: (R)-4-(3-(3,4-dihydroisoquinolin-2(1H)-yl)-2-hydroxypropyl)-7-(pyrimidin-5-ylamino)-3,4-dihydrobenzo[f][1,4]oxazepin-5(2H)-one (36)

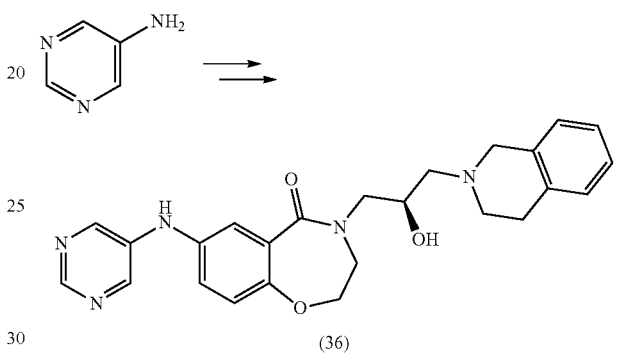

(36)

Compound 36 was synthesized in a method similar to that for compound 30a in Example 7, using pyrimidin-5-amine and (R)-7-bromo-4-(3-(3,4-dihydroisoquinolin-2(1H)-yl)-2-hydroxypropyl)-3,4-dihydrobenzo[f][1,4]oxazepin-5(2H)-one as starting material. $^1$H NMR (400 MHz, DMSO-d$_6$) δ (ppm) 8.63 (s, 1H), 8.52 (s, 1H), 8.49 (s, 2H), 7.35 (d, J=2.8 Hz, 1H), 7.26 (dd, J=2.9 Hz, 8.6 Hz, 1H), 7.03-7.10 (m, 4H), 6.99 (d, J=8.6 Hz, 1H), 4.86 (d, J=5.5 Hz, 1H), 4.34 (t, J=5.0 Hz, 2H), 4.02-4.04 (m, 1H), 3.88 (dd, J=3.5 Hz, 13.5 Hz, 1H), 3.61-3.63 (m, 4H), 2.67-2.81 (m, 4H), 2.54-2.55 (m, 2H); LC-MS (m/z): 446 [M+H]$^+$.

Example 36: (R)-4-(3-(3,4-dihydroisoquinolin-2(1H)-yl)-2-hydroxypropyl)-7-(pyrimidin-4-ylamino)-3,4-dihydrobenzo[f][1,4]oxazepin-5(2H)-one (37)

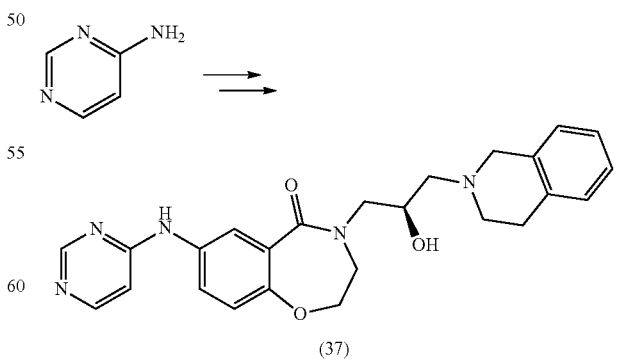

(37)

Compound 37 was synthesized in a method similar to that for compound 30a in Example 7, using pyrimidin-4-amine and (R)-7-bromo-4-(3-(3,4-dihydroisoquinolin-2(1H)-yl)-2- hydroxypropyl)-3,4-dihydrobenzo[f][1,4]oxazepin-5(2H)-one as starting material. $^1$H NMR (400 MHz, DMSO-d$_6$) δ (ppm) 9.62 (s, 1H), 8.60 (s, 1H), 8.25 (d, J=5.9 Hz, 1H), 7.91 (d, J=2.6 Hz, 1H), 7.75 (dd, J=2.7 Hz, 8.6 Hz, 1H), 7.04-7.10 (m, 4H), 7.00 (d, J=8.7 Hz, 1H), 6.74 (d, J=5.9 Hz, 1H), 4.88 (brs, 1H), 4.33-4.36 (m, 2H), 4.01-4.06 (m, 1H), 3.85-4.95 (m, 1H), 3.61-3.63 (m, 4H), 2.67-2.81 (m, 4H), 2.54-2.55 (m, 2H); LC-MS (m/z): 446 [M+H]$^+$.

Example 37: (R)-4-(3-(3,4-dihydroisoquinolin-2 (1H)-yl)-2-hydroxypropyl)-7-(pyrazin-2-ylamino)-3, 4-dihydrobenzo[f][1,4]oxazepin-5(2H)-one (38)

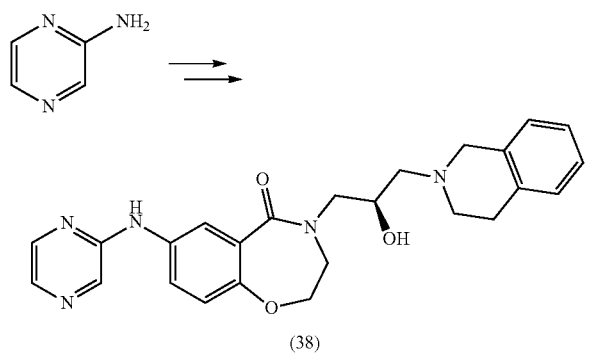

(38)

Compound 38 was synthesized in a method similar to that for compound 30a in Example 7, using pyrazin-2-amine and (R)-7-bromo-4-(3-(3,4-dihydroisoquinolin-2(1H)-yl)-2-hydroxypropyl)-3,4-dihydrobenzo[f][1,4]oxazepin-5(2H)-one as starting material. $^1$H NMR (400 MHz, DMSO-d$_6$) δ (ppm) 9.53 (s, 1H), 8.19 (dd, J=1.4 Hz, 1H), 8.10 (dd, J=1.4 Hz, 2.8 Hz, 1H), 7.96 (d, J=2.8 Hz, 1H), 7.90 (d, J=2.8 Hz, 1H), 7.75 (dd, J=2.8 Hz, 8.8 Hz, 1H), 7.04-7.11 (m, 4H), 6.99 (d, J=8.7 Hz, 1H), 4.87 (d, J=4.7 Hz, 1H), 4.32 (t, J=5.1 Hz, 2H), 4.01-4.06 (m, 1H), 3.85-4.95 (m, 1H), 3.61-3.63 (m, 4H), 2.67-2.81 (m, 4H), 2.55 (m, 2H); LC-MS (m/z): 446 [M+H]$^+$.

Example 38: (R)-4-(3-(3,4-dihydroisoquinolin-2 (1H)-yl)-2-hydroxypropyl)-7-(pyridazin-3-ylamino)-3,4-dihydrobenzo[f][1,4]oxazepin-5(2H)-one (39)

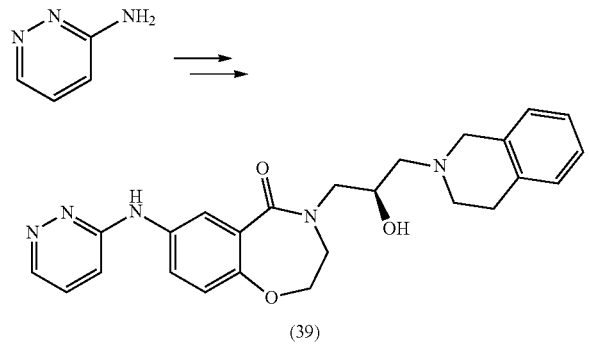

(39)

Compound 39 was synthesized in a method similar to that for compound 30a in Example 7, using pyridazin-3-amine and (R)-7-bromo-4-(3-(3,4-dihydroisoquinolin-2(1H)-yl)-2-hydroxypropyl)-3,4-dihydrobenzo[f][1,4]oxazepin-5(2H)- one as starting material. $^1$HNMR (400 MHz, DMSO-d$_6$) δ (ppm) 9.30 (s, 1H), 8.65 (dd, J=1.3 Hz, 4.4 Hz, 1H), 8.04 (d, J=2.8 Hz, 1H), 7.89 (dd, J=2.8 Hz, 8.8 Hz, 1H), 7.42 (dd, J=4.4 Hz, 9.0 Hz, 1H), 7.04-7.10 (m, 5H), 7.00 (d, J=8.7 Hz, 1H), 4.87 (d, J=4.6 Hz, 1H), 4.33 (t, J=5.6 Hz, 2H), 4.04-4.05 (m, 1H), 3.85-4.95 (m, 1H), 3.61-3.63 (m, 4H), 2.67-2.81 (m, 4H), 2.55 (m, 2H); LC-MS (m/z): 446 [M+H]$^+$.

Example 39: (R)-4-(3-(3,4-dihydroisoquinolin-2 (1H)-yl)-2-hydroxypropyl)-7-((1-methyl-2-oxo-1,2-dihydropyridin-4-yl)amino)-3,4-dihydrobenzo[f][1, 4]oxazepin-5(2H)-one (40)

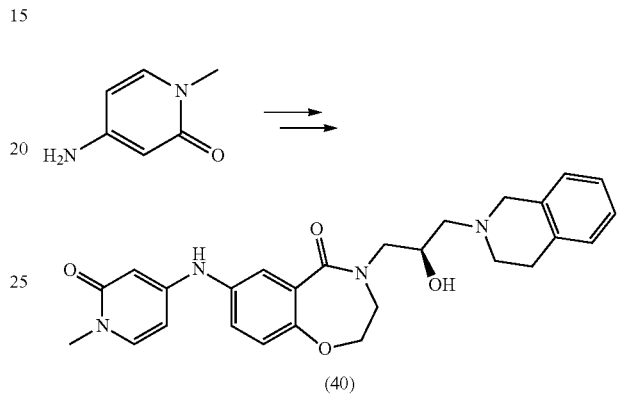

(40)

Compound 40 was synthesized in a method similar to that for compound 30a in Example 7, using 4-amino-1-methylpyridin-2(1H)-one and (R)-7-bromo-4-(3-(3,4-dihydroisoquinolin-2(1H)-yl)-2-hydroxypropyl)-3,4-dihydrobenzo[f][1,4]oxazepin-5(2H)-one as starting material. $^1$H NMR (400 MHz, DMSO-d$_6$) δ (ppm) 8.59 (s, 1H), 7.43 (d, J=7.5 Hz, 1H), 7.40 (d, J=2.8 Hz, 1H), 7.23 (dd, J=2.8 Hz, 8.6 Hz, 1H), 7.00-7.10 (m, 5H), 5.86 (dd, J=2.6 Hz, 7.5 Hz, 1H), 5.65 (d, J=2.4 Hz, 1H), 4.86 (d, J=4.6 Hz, 1H), 4.36 (t, J=4.9 Hz, 2H), 4.03-4.08 (m, 1H), 3.87-3.90 (m, 1H), 3.63 (m, 4H), 3.28 (s, 3H), 2.80-2.81 (m, 4H); LC-MS (m/z): 475 [M+H]$^+$.

Example 40: (R)-4-(3-(3,4-dihydroisoquinolin-2 (1H)-yl)-2-hydroxypropyl)-7-((1-methyl-1H-pyrazol-5-yl)amino)-3,4-dihydrobenzo[f][1,4]oxazepin-5 (2H)-one (41)

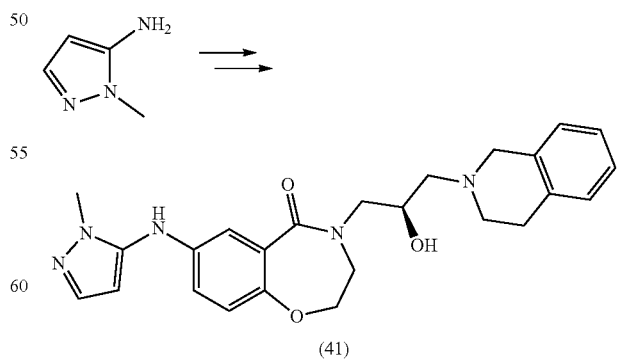

(41)

Compound 41 was synthesized in a method similar to that for compound 30a in Example 7, using 1-methyl-1H-pyrazol-5-amine and (R)-7-bromo-4-(3-(3,4-dihydroisoquinolin- 2(1H)-yl)-2-hydroxypropyl)-3,4-dihydrobenzo[f][1,4]oxazepin-5(2H)-one as starting material. ¹HNMR (400 MHz, DMSO-d₆) δ (ppm) 7.97 (s, 1H), 7.34 (s, 1H), 7.05-7.10 (m, 4H), 6.88-6.92 (m, 2H), 5.94 (s, 1H), 4.83 (s, 1H), 4.27 (m, 2H), 4.01-4.04 (m, 1H), 3.84-3.88 (m, 1H), 3.65 (s, 3H), 3.56 (m, 2H), 3.25 (m, 1H), 2.67-2.81 (m, 4H), 2.55 (m, 2H); LC-MS (m/z): 448 [M+H]⁺.

Example 41: (R)-4-(3-(3,4-dihydroisoquinolin-2(1H)-yl)-2-hydroxypropyl)-7-((5-methyl-1,3,4-oxadiazol-2-yl)amino)-3,4-dihydrobenzo[f][1,4]oxazepin-5(2H)-one (42)

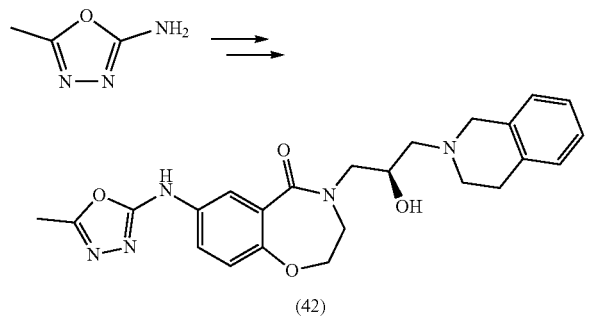

(42)

Compound 42 was synthesized in a method similar to that for compound 30a in Example 7, using 5-methyl-1,3,4-oxadiazol-2-amine and (R)-7-bromo-4-(3-(3,4-dihydro isoquinolin-2(1H)-yl)-2-hydroxypropyl)-3,4-dihydrobenzo[f][1,4]oxazepin-5(2H)-one as starting material. ¹HNMR (400 MHz, DMSO-d₆) δ (ppm) 10.33 (s, 1H), 7.80 (d, J=2.6 Hz, 1H), 7.61 (dd, J=2.7 Hz, 8.7 Hz, 1H), 7.00-7.10 (m, 5H), 4.88 (m, 1H), 4.32 (m, 2H), 4.02-4.04 (m, 1H), 3.87-3.91 (m, 1H), 3.58-3.65 (m, 4H), 2.74-2.82 (m, 4H), 2.40 (s, 3H); LC-MS (m/z): 450 [M+H]⁺.

Example 42: 4-((R)-3-(3,4-dihydroisoquinolin-2(1H)-yl)-2-hydroxypropyl)-7-((1-methyl-5-oxopyrrolidin-3-yl)amino)-3,4-dihydrobenzo[f][1,4]oxazepin-5(2H)-one (43)

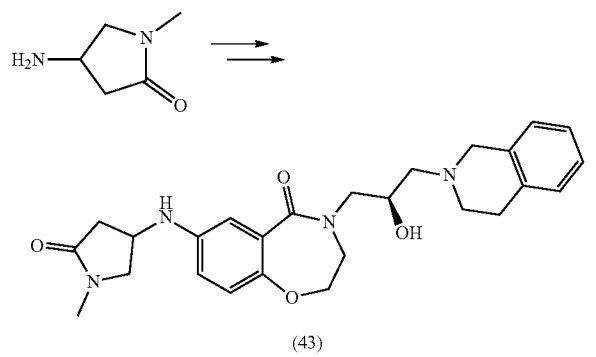

(43)

Compound 43 was synthesized in a method similar to that for compound 30a in Example 7, using 4-amino-1-methylpyrrolidin-2-one and (R)-7-bromo-4-(3-(3,4-dihydro isoquinolin-2(1H)-yl)-2-hydroxypropyl)-3,4-dihydrobenzo[f][1,4]oxazepin-5(2H)-one as starting material. ¹HNMR (400 MHz, DMSO-d₆) δ (ppm) 7.05-7.10 (m, 4H), 6.81 (d, J=8.0 Hz, 1H), 6.73 (s, 1H), 6.67 (d, J=8.0 Hz, 1H), 5.96 (brs, 1H), 4.87 (brs, 1H), 4.21 (m, 2H), 4.01 (m, 2H), 3.88 (m, 1H); LC-MS (m/z): 465 [M+H]⁺.

Example 43: 4-(3-(3,4-dihydroisoquinolin-2(1H)-yl)-2-hydroxypropyl)-1-methyl-7-(pyridazin-4-ylamino)-3,4-dihydro-1H-benzo[e][1,4]diazepine-2,5-dione (44)

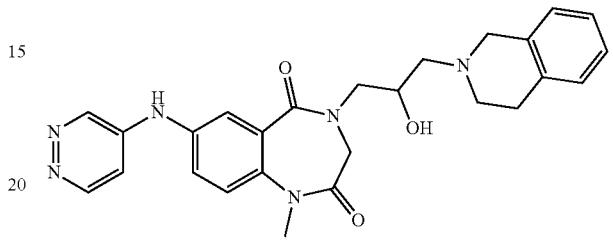

(44)

Step 1: 6-bromo-2H-benzo[d][1,3]oxazine-2,4(1H)-dione

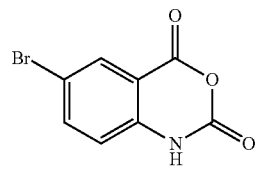 [SMILES: O=c1[nH]c2ccc(Br)cc2c(=O)o1]

To a stirred solution of 2-amino-5-bromobenzoic acid (2.16 g, 10.0 mmol, 3.0 eq) in THF (20 ml) was added a solution of triphosgene (1.04 g, 3.50 mmol, 1.05 eq) in THF (10 ml), and the resultant mixture was stirred at ambient temperature for 4 hours. The reaction mixture was diluted with cold water, and was filtered to collect precipitate. The obtained solid was washed with DCM, and was dried to afford 6-bromo-2H-benzo[d][1,3]oxazine-2,4(1H)-dione (1.63 g, 68% yield) as an off-white solid.

Step 2: 6-bromo-1-methyl-2H-benzo[d][1,3]oxazine-2,4(1H)-dione

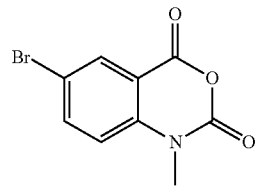

To a stirred solution of 6-bromo-2H-benzo[d][1,3]oxazine-2,4(1H)-dione (1.63 g, 6.73 mmol, 1.0 eq) in DMF (15 ml) was added NaH (60%, 0.82 g, 8.07 mmol, 1.2 eq) at ice-water bath temperature, and the resultant mixture was stirred for additional 15 min. MeI (0.5 ml, 7.41 mmol, 1.1 eq) was added, and the resultant mixture was stirred at ambient temperature for 2 hours. The reaction mixture was diluted with cold water, and precipitate was collected by filtration. The obtained solid was washed with water followed by mixed PE/EtOAc (10/1), and was dried to afford 6-bromo-1-methyl-2H-benzo[d][1,3]oxazine-2,4(1H)-dione (1.50 g, 84% yield) as an off-white solid.

Step 3: 7-bromo-1-methyl-3,4-dihydro-1H-benzo[e][1,4]diazepine-2,5-dione

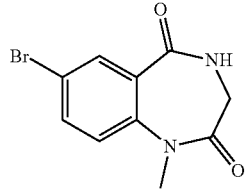

To a stirred solution of 6-bromo-1-methyl-2H-benzo[d][1,3]oxazine-2,4(1H)-dione (1.50 g, 5.86 mmol, 1.0 eq) and glycine (0.48 g, 6.45 mmol, 1.1 eq) in mixed solvents of DME (12 ml) and water (4 ml) was added TEA (2.4 ml, 17.6 mmol, 3.0 eq), and the resultant mixture was heated to 60° C. for 4 hours. The reaction mixture was concentrated to dryness, and was treated with AcOH (15 ml), and the resultant mixture was heated to reflux for additional 4 hours. The reaction mixture was concentrated to dryness, and the residue was treated with DCM and water. Organic phase was washed with brine, dried over MgSO$_4$, and was concentrated to dryness. The residue was purified by column chromatography (DCM/MeOH=20/1) to afford 7-bromo-1-methyl-3,4-dihydro-1H-benzo[e][1,4]diazepine-2,5-dione (0.64 g, 41% yield) as white solid.

Step 4: 4-(3-(3,4-dihydroisoquinolin-2(1H)-yl)-2-hydroxypropyl)-1-methyl-7-(pyridazin-4-ylamino)-3,4-dihydro-1H-benzo[e][1,4]diazepine-2,5-dione (44)

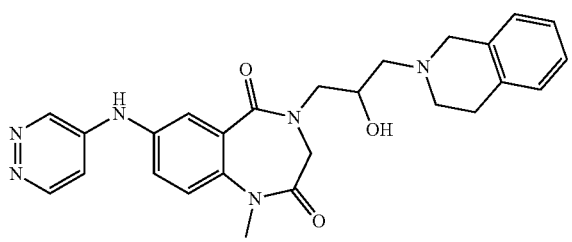 [SMILES: CN1C(=O)CN(CC(O)CN2CCc3ccccc3C2)C(=O)c2cc(Nc3ccnnc3)ccc21]

Compound 44 was synthesized in a method similar to that for compound 30a in Example 7, using pyridazin-4-amine and 7-bromo-1-methyl-3,4-dihydro-1H-benzo[e][1,4]diazepine-2,5-dione as starting material. $^1$HNMR (400 MHz, CDCl$_3$) δ (ppm) 8.94 (s, 1H), 8.77 (d, J=6.1 Hz, 1H), 7.74 (d, J=2.6 Hz, 1H), 7.42-7.46 (m, 2H), 7.24 (d, J=8.7 Hz, 1H), 7.01-7.15 (m, 5H), 4.07-4.22 (m, 3H), 3.82-3.85 (m, 2H), 3.63-3.67 (m, 1H), 3.38-3.41 (m, 4H), 2.91-2.96 (m, 3H), 2.75-2.77 (m, 1H), 2.52-2.64 (m, 2H); LC-MS (m/z): 473 [M+H]$^+$.

Example 44: 4-(3-(3,4-dihydroisoquinolin-2(1H)-yl)-2-hydroxypropyl)-1-methyl-7-(pyridazin-4-ylamino)-1,2,3,4-tetrahydro-5H-benzo[e][1,4]diazepin-5-one (45)

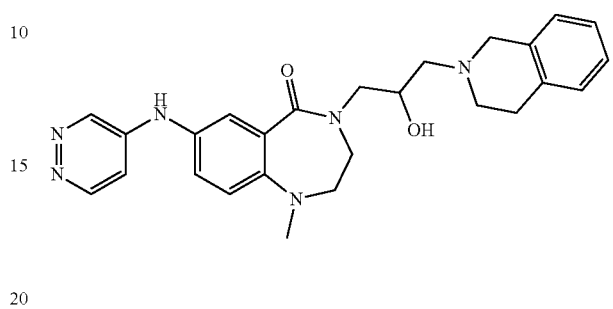

(45)

Step 1: tert-butyl (2-(5-bromo-2-fluorobenzamido)ethyl)(methyl)carbamate

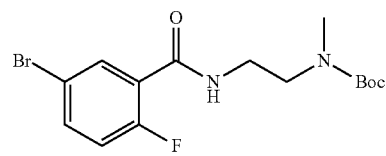 [SMILES: CN(CCNC(=O)c1cc(Br)ccc1F)C(=O)OC(C)(C)C]

To a stirred solution of 5-bromo-2-fluorobenzoic acid (6.37 g, 29.1 mmol, 1.0 eq) and tert-butyl (2-aminoethyl)(methyl)carbamate (7.60 g, 43.7 mmol, 1.5 eq) in DCM (100 ml) was added EDCI (11.12 g, 58.2 mmol, 2.0 eq) followed by DIPEA (11.27 g, 87.2 mmol, 3.0 eq), and the resultant mixture was stirred at ambient temperature for 3 hours. The reaction mixture was washed with water followed by 0.1 N HCl solution, washed with brine, dried over MgSO$_4$, and was concentrated to dryness. The residue was purified by column chromatography (PE/EtOAc=3/1) to afford tert-butyl (2-(5-bromo-2-fluorobenzamido)ethyl)(methyl)carbamate (4.20 g, 38% yield) as off-white solid.

Step 2: 5-bromo-2-fluoro-N-(2-(methylamino)ethyl)benzamide

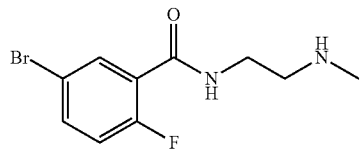

To a stirred solution of tert-butyl (2-(5-bromo-2-fluorobenzamido)ethyl) (methyl)carbamate (4.25 g, 11.3 mmol, 1.0 eq) in DCM (40 ml) was added TFA (10 ml) at ice-water bath temperature, and the resultant mixture was stirred at ambient temperature for 3 hours. The reaction mixture was concentrated to dryness, and was treated with DCM and water. The mixture was treated with 1 N NaOH solution until pH=7-8 was achieved. Organic phase was washed with brine, dried over MgSO$_4$, and was concentrated to dryness to afford 5-bromo-2-fluoro-N-(2-(methylamino)ethyl)benzamide (3.00 g, 97% yield) as light yellow oil.

Step 3: 7-bromo-1-methyl-1,2,3,4-tetrahydro-5H-benzo[e][1,4]diazepin-5-one

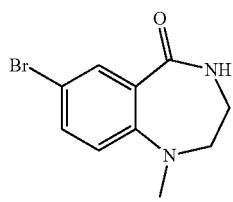

To a stirred solution of 5-bromo-2-fluoro-N-(2-(methylamino)ethyl)benzamide (1.40 g, 5.10 mmol, 1.0 eq) in DMSO (30 ml) was added solid $K_2CO_3$ (2.11 g, 15.3 mmol, 3.0 eq), and the resultant mixture was heated to 110° C. for 24 hours. The reaction was diluted with cold water, and was extracted with EtOAc. Organic phase was washed with water followed with brine, dried over $MgSO_4$, and was concentrated to dryness. The residue was purified by column chromatography (DCM/MeOH=100/1) to afford 7-bromo-1-methyl-1,2,3,4-tetrahydro-5H-benzo[e][1,4]diazepin-5-one (270 mg, 21% yield) as yellow oil.

Step 4: 4-(3-(3,4-dihydroisoquinolin-2(1H)-yl)-2-hydroxypropyl)-1-methyl-7-(pyridazin-4-ylamino)-1,2,3,4-tetrahydro-5H-benzo[e][1,4]diazepin-5-one (45)

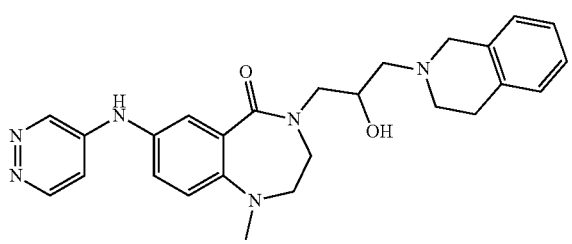 [SMILES: CN1CCN(CC(O)CN2CCc3ccccc3C2)C(=O)c2cc(Nc3ccnnc3)ccc21]

Compound 45 was synthesized in a method similar to that for compound 30a in Example 7, using pyridazin-4-amine and 7-bromo-1-methyl-1,2,3,4-tetrahydro-5H-benzo[e][1,4]diazepin-5-one as starting material. $^1$H NMR (400 MHz, DMSO-$d_6$) δ (ppm) 8.98 (s, 1H), 8.75 (d, J=2.5 Hz, 1H), 8.62 (d, J=6.1 Hz, 1H), 7.25-7.31 (m, 2H), 7.03-7.13 (m, 4H), 6.85-6.96 (m, 2H), 4.83 (d, J=4.4 Hz, 1H), 4.02-4.03 (m, 1H), 3.84 (dd, J=4.0 Hz, 13.4 Hz, 1H), 3.64 (s, 2H), 3.49-3.52 (m, 2H), 3.26-3.29 (m, 3H), 2.73-2.81 (m, 7H), 2.50 (m, 2H); LC-MS (m/z): 459 [M+H]$^+$.

Example 45: 4-(3-(3,4-dihydroisoquinolin-2(1H)-yl)-2-hydroxypropyl)-7-(pyridazin-4-ylamino)-3,4-dihydropyrido[3,2-f][1,4]oxazepin-5(2H)-one (47)

(47)

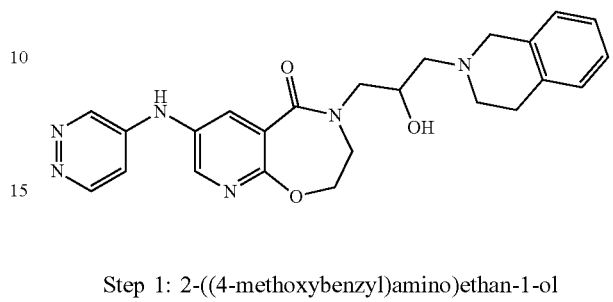

Step 1: 2-((4-methoxybenzyl)amino)ethan-1-ol

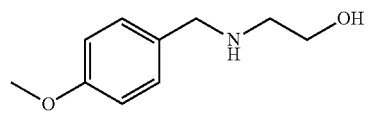

To a stirred solution of 4-methoxybenzaldehyde (93.00 g, 0.68 mol, 1.0 eq) in methanol (930 ml) was added 2-aminoethan-1-ol (45.69 g, 0.75 mol, 1.1 eq) and catalytic $MgSO_4$, and the resultant mixture was stirred at ambient temperature for 1 hour. Solid $NaBH_3CN$ (85.46 g, 1.36 mmol, 2.0 eq) was added in portions at ice-water bath temperature, and the resultant mixture was stirred at ambient temperature overnight. The reaction mixture was concentrated to dryness, and the residue was treated with water. The mixture was extracted with DCM three times, dried over $MgSO_4$, and was concentrated to dryness. The residue was purified by column chromatography (DCM/MeOH=5/1) to afford 2-((4-methoxybenzyl)amino)ethan-1-ol (32.00 g, 26% yield) as colorless oil.

Step 2: 5-bromo-2-fluoro-N-(2-hydroxyethyl)-N-(4-methoxybenzyl)nicotinamide

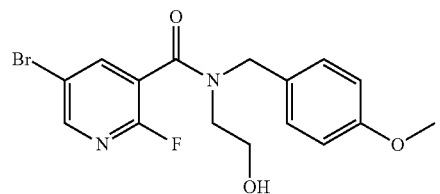 [SMILES: COc1ccc(CN(CCO)C(=O)c2cc(Br)cnc2F)cc1]

To a stirred solution of 5-bromo-2-fluoronicotinic acid (14.56 g, 66.2 mmol, 1.2 eq) and 2-((4-methoxybenzyl)amino)ethan-1-ol (10.00 g, 55.2 mmol, 1.0 eq) in DCM (200 ml) was added EDCI (12.66 g, 66.2 mmol, 1.2 eq), and the resultant mixture was stirred at ambient temperature for 5 hours. The reaction mixture was diluted with water, and was extracted with DCM. Organic phase was dried over $MgSO_4$, and was concentrated to dryness. The residue was purified by column chromatography (PE/EA=3/1) to afford 5-bromo-2-fluoro-N-(2-hydroxyethyl)-N-(4-methoxybenzyl)nicotinamide (7.00 g, 33% yield) as colorless oil.

Step 3: 7-bromo-4-(4-methoxybenzyl)-3,4-dihydropyrido[3,2-f][1,4]oxazepin-5(2H)-one

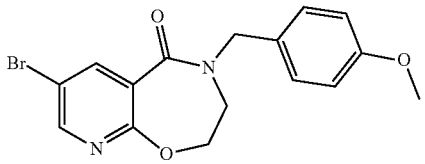 [SMILES: COc1ccc(CN2CCOc3ncc(Br)cc3C2=O)cc1]

To a stirred solution of 5-bromo-2-fluoro-N-(2-hydroxyethyl)-N-(4-methoxybenzyl) nicotinamide (7.00 g, 18.3 mmol, 1.0 eq) in DMF (40 ml) was added NaH (60%, 1.46 g, 36.5 mmol, 2.0 eq) at ice-water bath temperature, and the resultant mixture was stirred ambient temperature overnight. The reaction mixture was quenched by cold water, and was extracted with EA. Organic phase was washed with water, dried over MgSO$_4$, and was concentrated to dryness. The residue was purified by column chromatography (PE/EA=6/1) to afford 7-bromo-4-(4-methoxybenzyl)-3,4-dihydropyrido[3,2-f][1,4]oxazepin-5(2H)-one (2.00 g, 30% yield) as yellow oil.

Step 4: 7-bromo-3,4-dihydropyrido[3,2-f][1,4]oxazepin-5(2H)-one

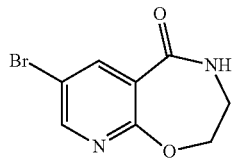 [SMILES: O=C1NCCOc2ncc(Br)cc21]

To a stirred solution of 7-bromo-4-(4-methoxybenzyl)-3,4-dihydropyrido[3,2-f][1,4]oxazepin-5(2H)-one (2.00 g, 5.49 mmol, 1.0 eq) in mixed solvents of MeCN (10 ml) and water (10 ml) was added solid CAN (9.03 g, 16.5 mmol, 3.0 eq) at ice-water bath temperature, and the resultant mixture was stirred for additional 1 hour. The reaction mixture was diluted with saturated NaCl, and was extracted with EA. Organic phase was washed with water, dried over MgSO$_4$, and was concentrated to dryness. The residue was purified by column chromatography (PE/EA=1/1) to afford 7-bromo-3,4-dihydropyrido[3,2-f][1,4]oxazepin-5(2H)-one (300 mg, 23% yield) as white solid.

Step 5: 4-(3-(3,4-dihydroisoquinolin-2(1H)-yl)-2-hydroxypropyl)-7-(pyridazin-4-ylamino)-3,4-dihydropyrido[3,2-f][1,4]oxazepin-5(2H)-one (47)

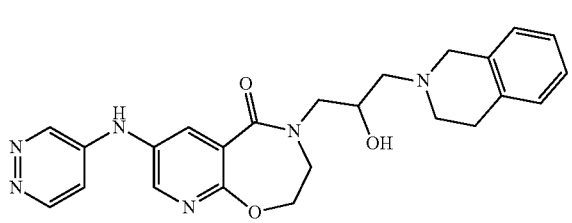 [SMILES: O=C1c2cc(Nc3ccnnc3)cnc2OCCN1CC(O)CN1CCc2ccccc2C1]

Compound 47 was synthesized in a method similar to that for compound 30a in Example 7, using pyridazin-4-amine and 7-bromo-3,4-dihydropyrido[3,2-f][1,4]oxazepin-5(2H)-one as starting material. $^1$HNMR (400 MHz, DMSO-d$_6$) δ (ppm) 9.29 (s, 1H), 8.83 (d, J=2.6 Hz, 1H), 8.68 (d, J=6.0 Hz, 1H), 8.33 (d, J=2.9 Hz, 1H), 8.03 (d, J=2.9 Hz, 1H), 6.98-7.11 (m, 5H), 4.92 (brs, 1H), 4.53 (t, J=4.5 Hz, 2H), 4.06 (m, 1H), 3.90 (dd, J=3.5 Hz, 13.6 Hz, 1H), 3.75-3.77 (m, 2H), 3.63-3.64 (m, 2H), 2.71-2.81 (m, 4H); LC-MS (m/z): 447 [M+H]$^+$.

Example 46: 4-(3-(3,4-dihydroisoquinolin-2(1H)-yl)-2-hydroxypropyl)-7-(pyridazin-4-ylamino)-3,4-dihydropyrido[4,3-f][1,4]oxazepin-5(2H)-one (48)

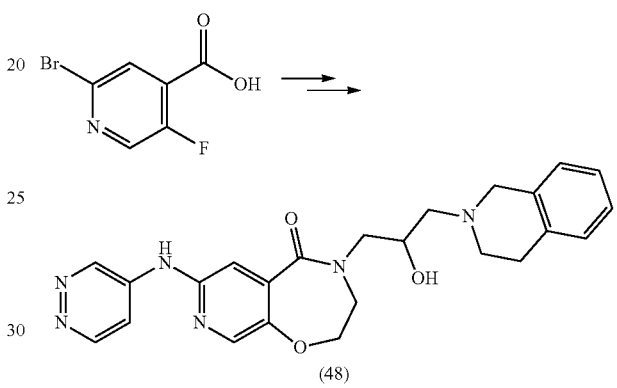

(48)

Compound 48 was synthesized in a method similar to that for compound 47 in Example 45, using 2-bromo-5-fluoroisonicotinic acid as starting material. $^1$HNMR (400 MHz, DMSO-d$_6$) δ (ppm) 9.91 (s, 1H), 9.19 (d, J=2.1 Hz, 1H), 8.82 (d, J=6.0 Hz, 1H), 8.13 (s, 1H), 8.02 (dd, J=2.9 Hz, 6.1 Hz, 1H), 7.24 (s, 1H), 7.03-7.12 (m, 4H), 4.91 (d, J=4.8 Hz, 1H), 4.40 (t, J=4.9 Hz, 2H), 4.04 (m, 1H), 3.88 (dd, J=3.4 Hz, 13.5 Hz, 1H), 3.64-3.68 (m, 4H), 3.40 (m, 1H), 2.73-2.82 (m, 4H), 2.50 (m, 2H); LC-MS (m/z): 447 [M+H]$^+$.

Example 47: 4-(3-(3,4-dihydroisoquinolin-2(1H)-yl)-2-hydroxypropyl)-7-(pyridazin-4-ylamino)-3,4-dihydropyrido[2,3-f][1,4]oxazepin-5(2H)-one (49)

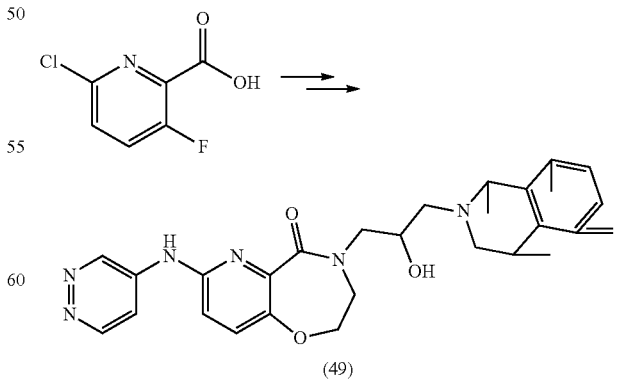

(49)

Compound 49 was synthesized in a method similar to that for compound 47 in Example 45, using 6-chloro-3-fluoropicolinic acid as starting material. ¹HNMR (400 MHz, DMSO-d₆) δ (ppm) 9.96 (s, 1H), 9.31 (d, J=2.4 Hz, 1H), 8.84 (d, J=6.0 Hz, 1H), 8.24 (dd, J=2.8 Hz, 6.0 Hz, 1H), 7.50 (d, J=8.8 Hz, 1H), 7.04-7.11 (m, 5H), 4.93 (d, J=3.6 Hz, 1H), 4.38 (t, J=4.9 Hz, 2H), 4.07 (brs, 1H), 3.94 (dd, J=3.3 Hz, 13.6 Hz, 1H), 3.63-3.66 (m, 4H), 3.30-3.35 (m, 1H), 2.75-2.83 (m, 4H), 2.50-2.54 (m, 2H); LC-MS (m/z): 447 [M+H]⁺.

Example 48: 4-(3-(3,4-dihydroisoquinolin-2(1H)-yl)-2-hydroxypropyl)-8-fluoro-7-(pyridazin-4-ylamino)-3,4-dihydrobenzo[f][1,4]oxazepin-5(2H)-one (50)

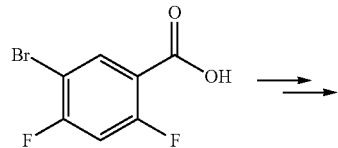

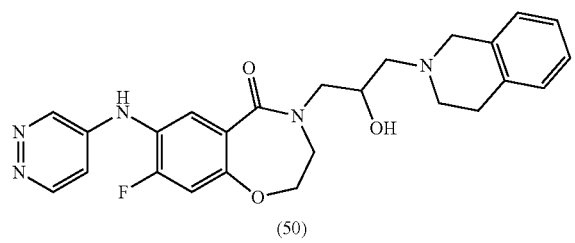

(50)

Compound 50 was synthesized in a method similar to that for compound 47 in Example 45, using 5-bromo-2,4-difluorobenzoic acid as starting material. ¹HNMR (400 MHz, DMSO-d₆) δ (ppm) 8.94 (s, 1H), 8.75 (d, J=2.8 Hz, 1H), 8.67 (d, J=6.0 Hz, 1H), 7.65 (d, J=9.4 Hz, 1H), 7.02-7.11 (m, 5H), 6.70-6.71 (m, 1H), 4.87 (d, J=4.8 Hz, 1H), 4.45 (t, J=4.7 Hz, 2H), 4.03 (m, 1H), 3.86-3.90 (m, 1H), 3.65-3.75 (m, 4H), 3.31 (m, 1H), 2.79-2.82 (m, 4H), 2.45-2.50 (m, 2H); LC-MS (m/z): 464 [M+H]⁺.

Example 49: 4-(3-(3,4-dihydroisoquinolin-2(1H)-yl)-2-hydroxypropyl)-9-fluoro-7-(pyridazin-4-ylamino)-3,4-dihydrobenzo[f][1,4]oxazepin-5(2H)-one (51)

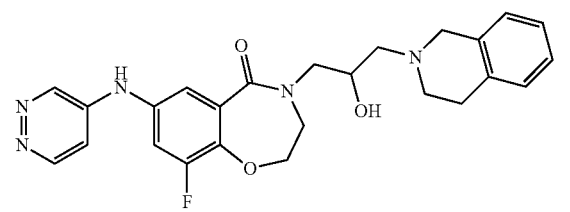

(51)

Step 1: 9-fluoro-3,4-dihydrobenzo[f][1,4]oxazepin-5(2H)-one

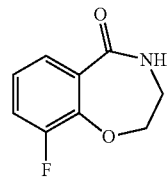 [SMILES: O=C1NCCOc2c(F)cccc21]

9-fluoro-3,4-dihydrobenzo[f][1,4]oxazepin-5(2H)-one was synthesized in similar method with 7-bromo-3,4-dihydropyrido[3,2-f][1,4]oxazepin-5(2H)-one in Example 45, using 2,3-difluorobenzoic acid as starting material.

Step 2: 7-bromo-9-fluoro-3,4-dihydrobenzo[f][1,4]oxazepin-5(2H)-one

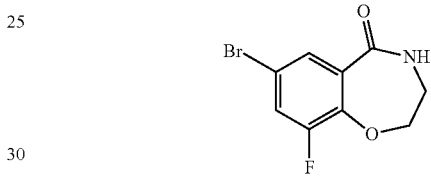

To a stirred mixture of 7-bromo-3,4-dihydropyrido[3,2-f][1,4]oxazepin-5(2H)-one (350 mg, 1.93 mmol, 1.0 eq) in conc. H2SO4 (5 ml) was added NBS (344 mg, 1.93 mmol, 1.0 eq) at ice-water bath temperature, and the resultant mixture was stirred for 3 hours. The reaction mixture was poured into cold water, and precipitate was collected by filtration. The solid was washed with sat'd NaHCO₃, and was dried to afford 7-bromo-9-fluoro-3,4-dihydrobenzo[f][1,4]oxazepin-5(2H)-one (400 mg, 80% yield) as an off-white solid.

Step 3: 4-(3-(3,4-dihydroisoquinolin-2(1H)-yl)-2-hydroxypropyl)-9-fluoro-7-(pyridazin-4-ylamino)-3,4-dihydrobenzo[f][1,4]oxazepin-5(2H)-one (51)

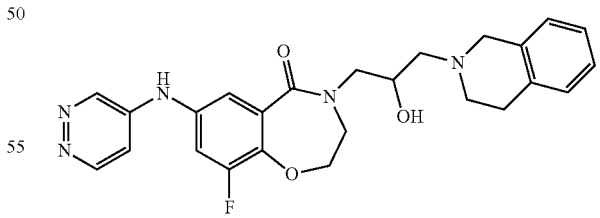

Compound 51 was synthesized in general procedure described above. ¹HNMR (400 MHz, DMSO-d₆) δ (ppm) 9.23 (s, 1H), 8.81 (d, J=2.6 Hz, 1H), 8.70 (d, J=6.0 Hz, 1H), 7.35 (dd, J=2.7 Hz, 11.6 Hz, 1H), 7.23 (s, 1H), 7.03-7.11 (m, 5H), 4.89 (d, J=4.4 Hz, 1H), 4.44 (t, J=4.9 Hz, 1H), 4.03 (brs, 1H), 3.89 (dd, J=3.5 Hz, 13.6 Hz, 1H), 3.64-3.68 (m, 4H), 3.31 (m, 1H), 2.73-2.81 (m, 4H), 2.50 (m, 2H); LC-MS (m/z): 464 [M+H]⁺.

Example 50: 7-((1-acetylpiperidin-4-yl)amino)-4-(3-(3,4-dihydroisoquinolin-2(1H)-yl)-2-hydroxy propyl)-3,4-dihydrobenzo[f][1,4]oxazepin-5(2H)-one (52)

Example 51: 7'-((1-acetylpiperidin-4-yl)amino)-2'-(3-(3,4-dihydroisoquinolin-2(1H)-yl)-2-hydroxypropyl)-2',3'-dihydro-1'H-spiro[cyclopropane-1,4'-isoquinolin]-1'-one (53)

(52)

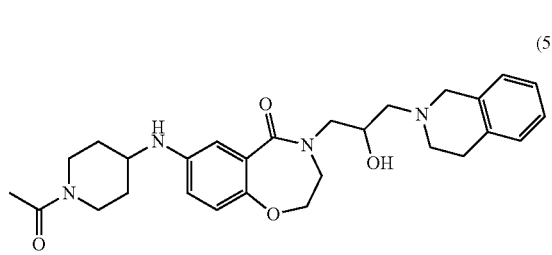

(53)

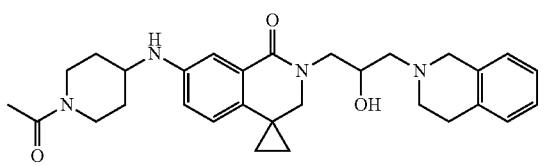

Compound 52 was synthesized in a method similar to that for compound 24a/24b in Example 6, using 7-bromo-4-(3-(3,4-dihydroisoquinolin-2(1H)-yl)-2-hydroxypropyl)-3,4-dihydrobenzo[f][1,4]oxazepin-5(2H)-one (example 7) as intermediate. $^1$HNMR (400 MHz, DMSO-d$_6$) δ (ppm) 7.03-7.12 (m, 4H), 6.77-6.79 (m, 2H), 6.68-6.71 (m, 1H), 5.47 (d, J=8.3 Hz, 1H), 4.82 (d, J=4.1 Hz, 1H), 4.18-4.21 (m, 3H), 4.00 (m, 1H), 3.86 (dd, J=3.6 Hz, 13.6 Hz, 1H), 3.77 (d, J=13.2 Hz, 1H), 3.64 (s, 2H), 3.41-3.53 (m, 3H), 3.17-3.31 (m, 2H), 2.73-2.83 (m, 5H), 2.00 (s, 3H), 1.84-1.89 (m, 2H), 1.27-1.29 (m, 2H); LC-MS (m/z): 493 [M+H]$^+$.

Compound 53 was synthesized in a method similar to that for compound 24a/24b in Example 6, using 7'-bromo-2',3'-dihydro-1'H-spiro[cyclopropane-1,4'-isoquinolin]-1'-one (example 34) as intermediate. $^1$HNMR (400 MHz, DMSO-d$_6$) δ (ppm) 7.18 (s, 1H), 7.02-7.11 (m, 4H), 6.71 (s, 1H), 5.58 (d, J=8.3 Hz, 1H), 4.76 (d, J=3.8 Hz, 1H), 4.19 (d, J=13.5 Hz, 1H), 4.03 (m, 1H), 3.75-3.81 (m, 2H), 3.63 (s, 2H), 3.36-3.50 (m, 3H), 3.16-3.21 (m, 2H), 2.72-2.82 (m, 5H), 2.47-2.51 (m, 2H), 2.00 (s, 3H), 1.84-1.89 (m, 2H), 1.28-1.30 (m, 2H), 0.88 (s, 4H); LC-MS (m/z): 503 [M+H]$^+$.

(52a)

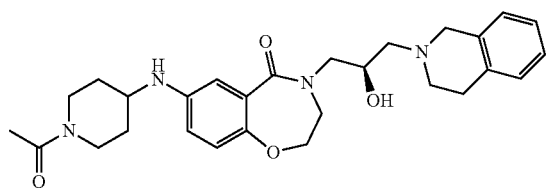

(53a)

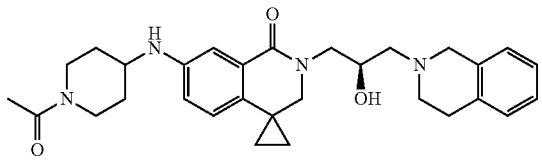

(52b)

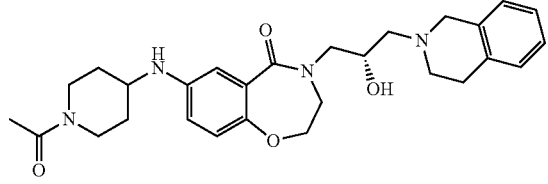

(53b)

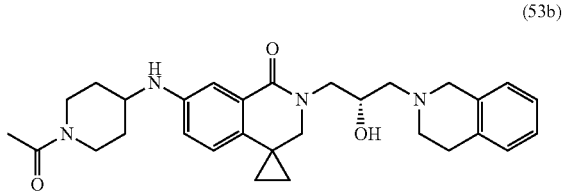 [SMILES: CC(=O)N1CCC(Nc2ccc3c(c2)C(=O)N(CC(O)CN2CCc4ccccc4C2)CC32CC2)CC1]

Compound 52a and compound 52b were prepared by chiral separation of compound 52. $^1$HNMR (400 MHz, DMSO-d$_6$) δ (ppm) 7.03-7.12 (m, 4H), 6.77-6.79 (m, 2H), 6.68-6.71 (m, 1H), 5.47 (d, J=8.3 Hz, 1H), 4.82 (d, J=4.1 Hz, 1H), 4.18-4.21 (m, 3H), 4.00 (m, 1H), 3.86 (dd, J=3.6 Hz, 13.6 Hz, 1H), 3.77 (d, J=13.2 Hz, 1H), 3.64 (s, 2H), 3.41-3.53 (m, 3H), 3.17-3.31 (m, 2H), 2.73-2.83 (m, 5H), 2.00 (s, 3H), 1.84-1.89 (m, 2H), 1.27-1.29 (m, 2H); LC-MS (m/z): 493 [M+H]$^+$.

Compound 53a and compound 53b were prepared by chiral separation of compound 53. $^1$HNMR (400 MHz, DMSO-d$_6$) δ (ppm) 7.18 (s, 1H), 7.02-7.11 (m, 4H), 6.71 (s, 1H), 5.58 (d, J=8.3 Hz, 1H), 4.76 (d, J=3.8 Hz, 1H), 4.19 (d, J=13.5 Hz, 1H), 4.03 (m, 1H), 3.75-3.81 (m, 2H), 3.63 (s, 2H), 3.36-3.50 (m, 3H), 3.16-3.21 (m, 2H), 2.72-2.82 (m, 5H), 2.47-2.51 (m, 2H), 2.00 (s, 3H), 1.84-1.89 (m, 2H), 1.28-1.30 (m, 2H), 0.88 (s, 4H); LC-MS (m/z): 503 [M+H]$^+$.

Example 52: (R)-7-((1-acetylpiperidin-4-yl)amino)-4-(3-(3,4-dihydroisoquinolin-2(1H)-yl)-2-hydroxypropyl)-9-fluoro-3,4-dihydrobenzo[f][1,4]oxazepin-5(2H)-one (2a) and (S)-7-((1-acetylpiperidin-4-yl)amino)-4-(3-(3,4-dihydroisoquinolin-2(1H)-yl)-2-hydroxypropyl)-9-fluoro-3,4-dihydrobenzo[f][1,4]oxazepin-5(2H)-one (2b)

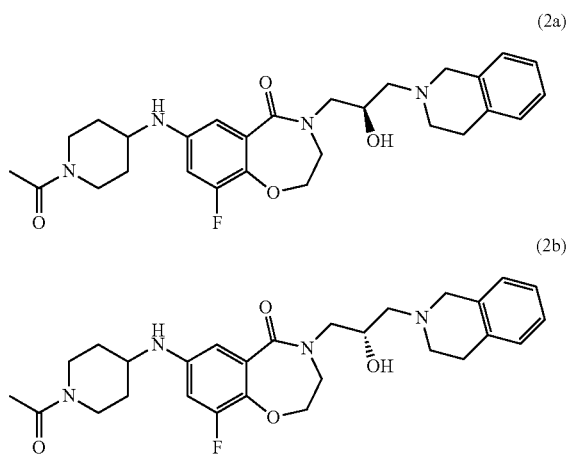

Compound 2a and 2b were synthesized in a procedure similar to that for compound 51 in Example 49, and were separated by chiral column chromatography. ¹HNMR (400 MHz, DMSO-d₆) δ (ppm) 7.03-7.11 (m, 4H), 6.58-6.65 (m, 2H), 5.79 (d, J=8.2 Hz, 1H), 4.87 (s, 1H), 4.18-4.25 (m, 3H), 4.00 (m, 1H), 3.75-3.88 (m, 2H), 3.43-3.64 (m, 5H), 3.17-3.29 (m, 2H), 2.73-2.82 (m, 5H), 2.50-2.51 (m, 2H), 2.00 (s, 3H), 1.84-1.88 (m, 2H), 1.25-1.28 (m, 2H); LC-MS (m/z): 511 [M+H]⁺.

Example 53: (R)-7-((1-acetylpiperidin-4-yl)amino)-4-(3-(3,4-dihydroisoquinolin-2(1H)-yl)-2-hydroxypropyl)-8-fluoro-3,4-dihydrobenzo[f][1,4]oxazepin-5(2H)-one (17a) and (S)-7-((1-acetylpiperidin-4-yl)amino)-4-(3-(3,4-dihydroisoquinolin-2(1H)-yl)-2-hydroxypropyl)-8-fluoro-3,4-dihydrobenzo[f][1,4]oxazepin-5(2H)-one (17b)

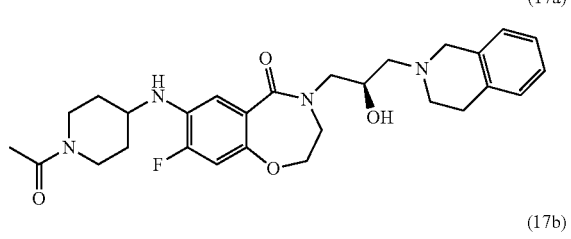

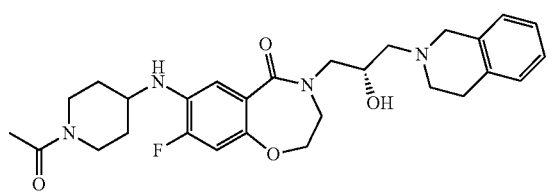

Compound 17a and 17b were synthesized in a procedure similar to that for compound 51 in Example 49, and were separated by chiral column chromatography. ¹HNMR (400 MHz, DMSO-d₆) δ (ppm) 7.03-7.12 (m, 4H), 6.95 (d, J=10.0 Hz, 1H), 6.79 (d, J=12.2 Hz, 1H), 5.11 (d, J=7.4 Hz, 1H), 4.85 (d, J=4.8 Hz, 1H), 4.26-4.32 (m, 3H), 4.01-4.04 (m, 1H), 3.79-3.90 (m, 2H), 3.50-3.63 (m, 5H), 3.15-3.26 (m, 2H), 2.68-2.81 (m, 5H), 2.48-2.50 (m, 2H), 2.00 (s, 3H), 1.84-1.99 (m, 2H), 1.25-1.28 (m, 2H); LC-MS (m/z): 511 [M+H]⁺.

Example 54: 7-((1-acetylpiperidin-4-yl)amino)-4-(3-(3,4-dihydroisoquinolin-2(1H)-yl)-2-hydroxy propyl)-6-fluoro-3,4-dihydrobenzo[f][1,4]oxazepin-5(2H)-one (46)

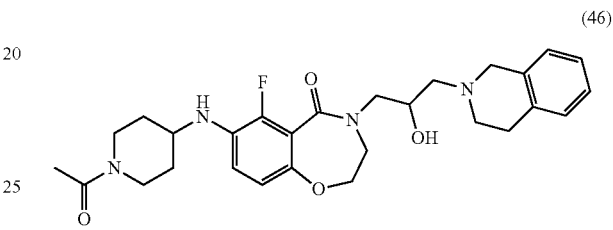

Compound 46 was synthesized in a method similar to that for compound 24a/24b in Example 6, using 7-bromo-6-fluoro-3,4-dihydrobenzo[f][1,4]oxazepin-5(2H)-one as intermediate. ¹HNMR (400 MHz, DMSO-d₆) δ (ppm) 7.04-7.09 (m, 4H), 6.87 (t, J=8.4 Hz, 1H), 6.71 (d, J=8.5 Hz, 1H), 5.07 (d, J=6.7 Hz, 1H), 4.86 (brs, 1H), 4.32 (d, J=12.0 Hz, 1H), 4.16 (s, 2H), 3.99 (s, 1H), 3.82 (t, J=14.3 Hz, 2H), 3.52-3.63 (m, 5H), 3.07-3.31 (m, 3H), 2.67-2.81 (m, 5H), 2.50 (m, 2H), 1.99 (s, 3H), 1.84-1.92 (m, 2H), 1.20-1.40 (m, 2H); LC-MS (m/z): 511 [M+H]⁺.

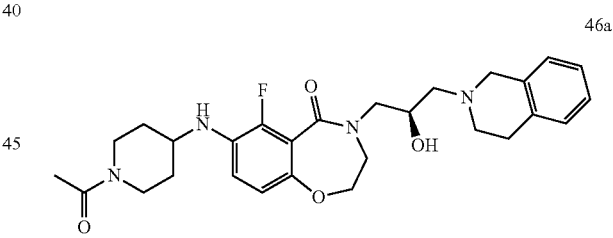

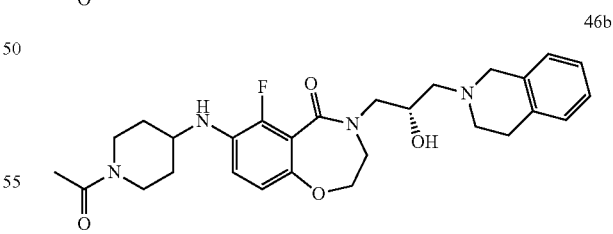

Compound 46a and compound 46b were prepared by chiral separation of compound 46. ¹HNMR (400 MHz, DMSO-d₆) δ (ppm) 7.04-7.09 (m, 4H), 6.87 (t, J=8.4 Hz, 1H), 6.71 (d, J=8.5 Hz, 1H), 5.07 (d, J=6.7 Hz, 1H), 4.86 (brs, 1H), 4.32 (d, J=12.0 Hz, 1H), 4.16 (s, 2H), 3.99 (s, 1H), 3.82 (t, J=14.3 Hz, 2H), 3.52-3.63 (m, 5H), 3.07-3.31 (m, 3H), 2.67-2.81 (m, 5H), 2.50 (m, 2H), 1.99 (s, 3H), 1.84-1.92 (m, 2H), 1.20-1.40 (m, 2H); LC-MS (m/z): 511 [M+H]⁺.

Example 55: 7-((2-acetyl-2-azaspiro[3.3]heptan-6-yl)amino)-4-(3-(3,4-dihydroisoquinolin-2(1H)-yl)-2-hydroxypropyl)-3,4-dihydrobenzo[f][1,4]oxazepin-5(2H)-one (54)

Example 57: 7-((3-acetyl-3-azabicyclo[3.1.0]hexan-6-yl)amino)-4-(3-(3,4-dihydroisoquinolin-2(1H)-yl)-2-hydroxypropyl)-3,4-dihydrobenzo[f][1,4]oxazepin-5(2H)-one (56)

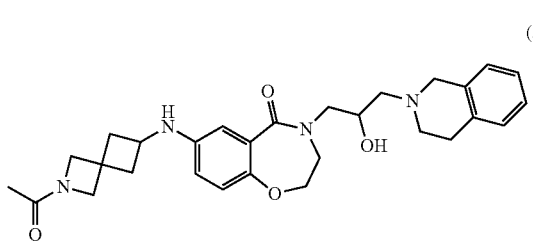
(54)

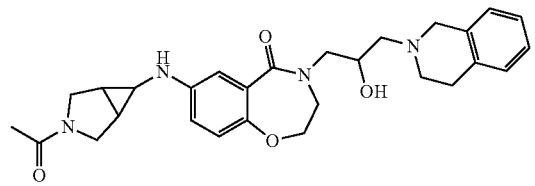
(56)

Compound 54 was synthesized in a method similar to that for compound 24a/24b in Example 6, using 1-(6-amino-2-azaspiro[3.3]heptan-2-yl)ethan-1-one as the starting material. $^1$H NMR (400 MHz, DMSO-$d_6$) δ (ppm) 7.03-7.11 (m, 4H), 6.78 (d, J=8.6 Hz, 1H), 6.66 (d, J=2.8 Hz, 1H), 6.57 (dd, J=2.9 Hz, 8.6 Hz, 1H), 5.81 (dd, J=2.0 Hz, 6.6 Hz, 1H), 4.82 (d, J=4.7 Hz, 1H), 4.16-4.21 (m, 3H), 4.01-4.04 (m, 2H), 3.85-3.88 (m, 2H), 3.76 (s, 1H), 3.63 (m, 3H), 3.50-3.52 (m, 2H), 3.26-3.30 (m, 1H), 2.80-2.81 (m, 2H), 2.73-2.74 (m, 2H), 2.56-2.60 (m, 2H), 2.50 (m, 2H), 1.95-1.99 (m, 2H), 1.71-1.73 (m, 3H); LC-MS (m/z): 505 [M+H]$^+$.

Compound 56 was synthesized in a method similar to that for compound 24a/24b in Example 6, using 1-(6-amino-3-azabicyclo[3.1.0]hexan-3-yl)ethan-1-one as the starting material. $^1$HNMR (400 MHz, DMSO-$d_6$) δ (ppm) 7.13-7.17 (m, 3H), 7.03-7.05 (m, 2H), 6.91 (d, J=8.6 Hz, 1H), 6.77 (dd, J=2.9 Hz, 8.6 Hz, 1H), 4.35 (m, 2H), 4.11-4.15 (m, 2H), 3.53-3.95 (m, 10H), 2.62-2.99 (m, 7H), 2.23 (s, 1H), 2.05 (s, 3H); LC-MS (m/z): 491 [M+H]$^+$.

Example 58: (R)-8-((1-acetylpiperidin-4-yl)amino)-2-(3-(3,4-dihydroisoquinolin-2(1H)-yl)-2-hydroxypropyl)-2,3,4,5-tetrahydro-1H-3,5-methanobenzo[c]azepin-1-one (57a) and (S)-8-((1-acetylpiperidin-4-yl)amino)-2-(3-(3,4-dihydroisoquinolin-2(1H)-yl)-2-hydroxypropyl)-2,3,4,5-tetrahydro-1H-3,5-methanobenzo[c]azepin-1-one (57b)

Example 56: 7-((8-acetyl-8-azabicyclo[3.2.1]octan-3-yl)amino)-4-(3-(3,4-dihydroisoquinolin-2(1H)-yl)-2-hydroxypropyl)-3,4-dihydrobenzo[f][1,4]oxazepin-5(2H)-one (55)

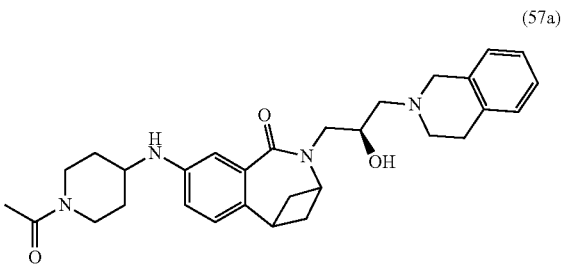
(57a)

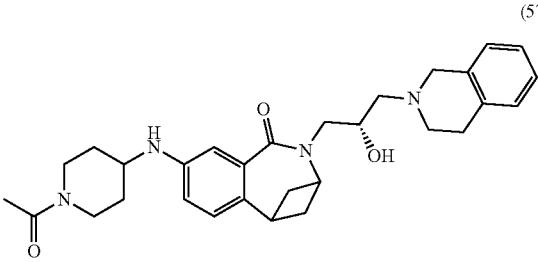
(57b)

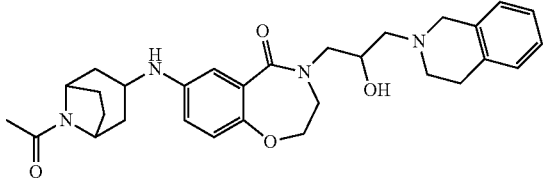
(55)

Compound 55 was synthesized in a method similar to that for compound 24a/24b in Example 6, using 1-(3-amino-8-azabicyclo[3.2.1]octan-8-yl)ethan-1-one as the starting material. $^1$H NMR (400 MHz, DMSO-$d_6$) δ (ppm) 7.03-7.10 (m, 4H), 6.70-6.78 (m, 3H), 5.29 (d, J=9.0 Hz, 1H), 4.83 (d, J=4.8 Hz, 1H), 4.44 (m, 1H), 4.18-4.22 (m, 3H), 4.00-4.04 (m, 1H), 3.84-3.88 (m, 1H), 3.70-3.80 (m, 1H), 3.63 (s, 2H), 3.50-3.52 (m, 2H), 3.26-3.28 (m, 2H), 2.72-2.83 (m, 4H), 2.50 (m, 2H), 1.97-1.99 (m, 4H), 1.78-1.88 (m, 4H), 1.34-1.37 (m, 2H); LC-MS (m/z): 519 [M+H]$^+$.

Compound 57a and 57b were synthesized in a method similar to that for compound 52a and 52b in Example 50, using 8-Bromo-2,3,4,5-tetrahydro-3,5-methano-1H-2-benzazepin-1-one as starting material which was prepared according to reported procedure in patent WO2013120980. $^1$HNMR (400 MHz, DMSO-$d_6$) δ (ppm) 7.79 (d, J=2.4 Hz, 1H), 7.02-7.10 (m, 3H), 6.95 (d, J=8.1 Hz, 1H), 6.60 (dd, J=2.5 Hz, 8.1 Hz, 1H), 5.60 (d, 1H), 4.71 (d, J=4.7 Hz, 1H), 4.18-4.22 (m, 2H), 3.94-4.00 (m, 2H), 3.76 (m, 1H), 3.60 (s, 2H), 3.46-3.48 (m, 1H), 3.18-3.28 (m, 3H), 2.70-2.84 (m, 5H), 2.43-2.45 (m, 2H), 2.01 (s, 3H), 1.85-1.93 (m, 2H), 1.53-1.60 (m, 2H), 1.18-1.31 (m, 4H); LC-MS (m/z): 503 [M+H]⁺.

Example 59: PRMT5 Biochemical Inhibitory Assay

Human recombinant PRMT5 in complex with human recombinant MEP50, co-expressed in an insect cell/baculovirus expression system was purchased from Reaction Biology (Malvern, Pa.). Biotin-labeled Histone H4 peptide (1-21) substrate was purchased from Anaspec (Fremont, Calif.). Anti-H4R3-Me AlphaLISA acceptor beads and Streptavidin labeled AlphaLISA donor beads were obtained from PerkinElmer (Waltham, Mass.). S-adenosylmethionine (SAM), Tween20, dimethylsulfoxide (DMSO), and Tris buffer were obtained from Sigma at the highest level of purity available.

General Procedure for PRMT5/MEP50 AlphaLISA Enzyme Inhibitory Assays: Assays were performed in the buffer consisting of 50 mM Tris, pH 8.5, 5 mM MgCl₂, 50 mM NaCl with 0.01% Tween20 and 1 mM DTT added right before the assay. 2.5 μL of compound solution in the assay buffer with 4% DMSO and 5 μL of PRMT5/MRP50 complex/SAM mixture solution in the assay buffer which was pre-incubated for 30 minutes were added into a white low volume 384 well microtiter plate. This mixture solution was incubated for 15 minutes with gentle shaking at room temperature. Methyl transfer reaction was initiated by adding 2.5 μL of Biotin-H4 (1-21) peptide substrate solution in the assay buffer. Final concentrations of PRMT5/MEP50, SAM, Biotin-H4 peptide substrate, and DMSO were 25 nM, 10 μM, 30 nM, and 1%, respectively. The reaction was allowed to perform for 120 minutes in dark with gentle shaking at room temperature after which 5 μL of Anti-H4R3-Me AlphaLISA acceptor beads in detection buffer from the manufacturer was added into the reaction mixture followed by incubation for 60 minutes. 10 μL of Streptavidin labeled AlphaLISA donor beads in detection buffer was added into the mixture followed by 30 minute incubation. Final acceptor and donor beads concentrations were 10 μg/mL. Plates were read on an Envision multimode plate reader from PerkinElmer (Waltham Mass., USA) with an excitation wavelength of 680 nm and emission wavelength of 615 nm. IC50 values of inhibitors were obtained by fitting the fluorescence intensity vs inhibitor concentrations in a sigmoidal dose-response curve (variable slopes, four parameters) using Prism 7 (La Jolla, Calif.). Results for representative compounds described herein are shown in Table 2, in which C1 stands for Ref 1 (EPZ-015666a); C2 stands for EPZ-015666b; and C3 stands for Ref 2 (EPZ-015938a).

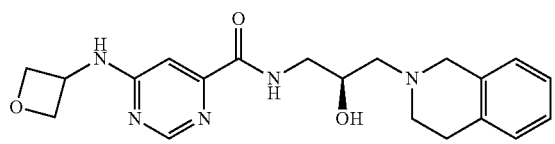

EPZ015666a

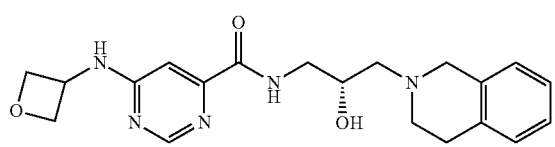

EPZ015666b

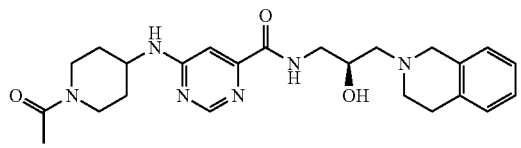

EPZ015938a

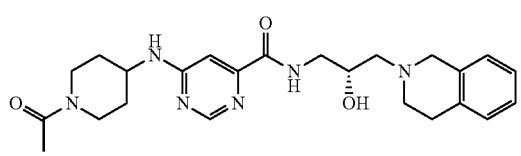

EPZ015938b

TABLE 2

| Compound | IC50 (nM) |
|---|---|
| C1 | 85 |
| C2 | 794 |
| C3 | 38 |
| 1 | 97 |
| 2a | 57 |
| 2b | 159 |
| 3 | 568 |
| 4 | 303 |
| 5 | 131 |
| 6 | 77 |
| 7 | 236 |
| 8 | 232 |
| 9 | 2441 |
| 10 | 1012 |
| 11 | 462 |
| 12 | 29 |
| 12a | 12 |
| 12b | 235 |
| 13 | 578 |
| 14 | 158 |
| 15 | 217 |
| 16 | 447 |
| 17a | 248 |
| 17b | 722 |
| 18 | 2225 |
| 19 | 623 |
| 20 | 132 |
| 21 | 480 |
| 22 | 21 |
| 23 | 61 |
| 24 | 14 |
| 24a | 13 |
| 24b | 19 |
| 25 | 10 |
| 26 | 487 |
| 27 | 21 |
| 28 | 11.4 |
| 28a | 4.9 |
| 28b | 296 |
| 29 | 39 |
| 29a | 8.4 |
| 29b | 126 |
| 30 | 13 |
| 30a | 4.6 |
| 30b | 36 |
| 31 | 179 |
| 32 | 37.2 |
| 33 | 22.4 |
| 34 | 15.7 |
| 35 | 6.1 |
| 36 | 10.3 |
| 37 | 9.9 |
| 38 | 13.6 |
| 39 | 22.5 |
| 40 | 12.2 |
| 41 | 9.9 |

TABLE 2-continued

| Compound | IC50 (nM) |
|---|---|
| 42 | 20.2 |
| 43 | 51.7 |
| 44 | 6.9 |
| 45 | 9.6 |
| 46 | 138 |
| 47 | 56.3 |
| 48 | 15.8 |
| 49 | 690 |
| 50 | 7.7 |
| 51 | 6.5 |
| 52a | 80 |
| 52b | 108 |
| 53a | — |
| 53b | — |
| 54 | 138 |
| 55 | 195 |
| 56 | 1103 |
| 57a | 92.5 |
| 57b | 209 |

Example 60: Cell Proliferation Inhibition Assay

Materials and Cell Lines: Z-138, U251, and MIA PaCa2 cells were purchased from ATCC (American Type Culture Collection, Manassas, Va.) and Chinese Academy of Science (Shanghai, China). Iscove's Modified Dulbecco's Medium (IMDM), Dulbecco's Modified Eagle Medium (DMEM), penicillin-streptomycin, heat inactivated fetal bovine serum (FBS), and horse serum was purchased from ThermoFisher, Waltham, Mass., USA. Corning 96- and 384-well cell culture plates were purchased from ThermoFisher, Waltham, Mass., USA. Cell-Titer Glo® was purchased from Promega Corporation, Madison, Wis., USA.

In order to evaluate the inhibitory ability of compounds synthesized on the proliferation of the Mantle Cell Lymphoma Z-138 cell, exponentially growing cells were seeded in the media of IMDM with 10% horse serum and 1% penicillin-streptomycin at a concentration of 30000 cells/ml in a 96-well plate with 100 ul per well and incubated overnight at 37° C., 5% $CO_2$ incubator. Compounds were prepared as 10-point, 3-fold serial dilutions in DMSO, beginning at 6 mM. 1 µl of DMSO solutions from the compound stock plates were added to 99 ul of cell culture media (final top concentration of compound in the assay was 30 uM and the final concentration of DMSO was 0.5%). 100 µL of compound solutions in media were added to each well of Z-138 cell plates. After adding compound solutions, assay plates were incubated for 4 days at 37° C., 5% $CO_2$. Cell viability was measured using the Cell Counting Kit-8 (CCK8) obtained from the Beyotime Biotehnology, Shanghai, China. 20 ul of CCK8 reagent was added to each well of the Z-138 assay plate which was incubated at 37° C. for 2 hours. O.D. at 450 nm was read with the FlexStation 3 microplate reader (Molecular Devices, Sunnyvale, Calif. 94089 USA). The concentrations of compounds inhibiting cell viability by 50% (IC50 values) were determined using a sigmoidal dose-response model (variable slopes, four parameters) in Prism 7 (La Jolla, Calif.).

In order to evaluate the inhibitory ability of compounds synthesized on the proliferation of the Glioblastoma U-251 cell, exponentially growing cells were seeded in the cell culture media of DMEM with 10% FBS and 1% penicillin-streptomycin at a concentration of 10000 cells/ml in a 384-well plate with 20 ul per well and incubated overnight at 37° C., 5% $CO_2$ incubator. Compounds were prepared as 10-point, 3-fold serial dilutions in DMSO, beginning at 6 mM. 1 µl of DMSO solutions from the compound stock plates were added to 99 ul of cell culture media (final top concentration of compound in the assay was 30 uM and the final concentration of DMSO was 0.5%). 20 µL of compound solutions in media were added to each well of U-251 cell plates. After adding compound solutions, assay plates were incubated for 12 days at 37° C., 5% $CO_2$. During this incubation period, cell culture media with freshly dissolved testing compounds was changed every 4 days. After removing old media from cell plates, 40 ul of media with testing compounds dissolved, which were prepared by adding 1 ul of compound DMSO serial solutions to 199 ul of cell media, were added to the assay plates with the same layout as they were initially prepared. After 8 or 12 days, cell viability was measured using the CellTiter-Glo assay kit from Promega (Madison, Wis., USA) by quantitating the ATP present in the cell cultures. 20 µL of CellTiter-Glo reagent was added to each well of the cell plates. Luminescence was read after 10 minute of incubation with the Envision multiple plate reader from PerkinElmer (Waltham, Mass., USA). The concentrations of compounds inhibiting cell viability by 50% (IC50 values) were determined using a sigmoidal dose-response model (variable slopes, four parameters) in Prism 7 (La Jolla, Calif., USA).

In order to evaluate the inhibitory ability of compounds synthesized on the proliferation of the Pancreatic Carcinoma MIA PaCa-2 cell, exponentially growing cells were seeded in the culture media of DMEM with 10% FBS, 2.5% horse serum, 1 mM of Sodium Pyruvate and 1% penicillin-streptomycin at a concentration of 2500 cells/ml in a 384-well plate with 20 ul per well and incubated overnight at 37° C., 5% CO2 incubator. Compounds were prepared as 10-point, 3-fold serial dilutions in DMSO, beginning at 6 mM. 1 µl of DMSO solutions from the compound stock plates were added to 99 ul of cell media (final top concentration of compound in the assay was 30 uM and the final concentration of DMSO was 0.5%). 20 µL of compound solutions in media were added to each well of MIA PaCa-2 cell plates. After adding compound solutions, assay plates were incubated for 12 days at 37° C., 5% $CO_2$. During this incubation period, cell media was changed every 4 days. After removing old media from cell plates, 40 ul of media with testing compounds dissolved, which were prepared by adding 1 ul of compound DMSO serial solutions to 199 ul of cell media, were added to the assay plates with the same layout as they were initially prepared. After 8 or 12 days, cell viability was measured using the CellTiter-Glo assay kit from Promega (Madison, Wis., USA) by quantitating the ATP present in the cell cultures. 20 µL of CellTiter-Glo reagent was added to each well of the cell plates. Luminescence was read after 10 minute of incubation with the Envision multiple plate reader from PerkinElmer (Waltham, Mass., USA). The concentrations of compounds inhibiting cell viability by 50% (IC50 values) were determined using a sigmoidal dose-response model (variable slopes, four parameters) in Prism 7 (La Jolla, Calif., USA). Results for representative compounds described herein are shown in Table 3.

TABLE 3

| | IC50 (µM) | | |
|---|---|---|---|
| | Z-138 | U-251 | MIA PaCa2 |
| Ref 1 (EPZ-015666a) | 0.11, 0.16 | 1.2 | 2.0 |
| EPZ-015666b | 9.1 | 28.3 | 12.1 |

TABLE 3-continued

| | IC50 (μM) | | |
|---|---|---|---|
| | Z-138 | U-251 | MIA PaCa2 |
| Ref 2 (EPZ-015938a) | 0.07 | 0.17 | 0.15 |
| EPZ-015938b | 0.6 | 14.4 | 6.0 |
| 2a | 0.041 | | 0.024 |
| 12a | 0.13 | 0.48 | 0.66 |
| 24a | 0.014 | 0.097 | 0.13 |
| 28a | 0.029 | 0.50 | 0.68 |
| 29a | 0.073 | 0.14 | 0.40 |
| 30a | 0.018 | 0.18 | 0.23 |
| 52a | 0.014 | 0.293 | 0.114 |
| 52b | 0.137 | 5.8 | 0.83 |

Example 61: Cell Proliferation Inhibitory Activity Screening on Breast, Liver and Lung Cancer Cell Line Panels Inhibitory ability of compounds synthesized on the proliferation of three panels of cancer cell lines, including 5 breast cancer, 6 liver cancer, and 3 lung cancer cell lines were evaluated. Exponentially growing cells were seeded in the media of choice at various cell densities in 384-well plates with 20 ul per well and incubated overnight at 37° C., 5% $CO_2$ incubator. Exact cell culture media and cell densities of each individual cell line were listed in Table 4. Compounds were prepared as 10-point, 3-fold serial dilutions in DMSO, beginning at 6 mM. 1 μl of DMSO solutions from the compound stock plates were added to 99 ul of cell media (final top concentration of compound in the assay was 30 uM and the final concentration of DMSO was 0.5%). 20 μL of compound solutions in media were added to each well of plates with cells seeded. After adding compound solutions, assay plates were incubated for 8 and 12 days, respectively, at 37° C., 5% $CO_2$. During this incubation period, cell media was changed every 4 days. After removing old media from cell plates, 40 ul of media with testing compounds dissolved, which were prepared by adding 1 ul of compound DMSO serial solutions to 199 ul of cell media, were added to the assay plates with the same layout as they were initially prepared. After 8 or 12 days, cell viability was measured using the CellTiter-Glo assay kit from Promega (Madison, Wis., USA) by quantitating the ATP present in the cell cultures. 20 μL of CellTiter-Glo reagent was added to each well of the cell plates. Luminescence was read after 10 minute of incubation with the Envision multiple plate reader from PerkinElmer (Waltham, Mass., USA). The concentrations of compounds inhibiting cell viability by 50% (IC50 values) were determined using a sigmoidal dose-response model (variable slopes, four parameters) in Prism 7 (La Jolla, Calif., USA).

TABLE 4

Cell culture media and cell densities used for three cancer cell panels' proliferation inhibition screening

| | Cell Culture Media | Cell density cells/well (8/12 Days) |
|---|---|---|
| Breast Cancer | | |
| BT474 | RPMI1640 + 10% FBS + 1% PS | 1500/500 |
| MCF-7 | DMEM + 10% FBS + 1% PS | 300/100 |
| MDA-MB-231 | DMEM + 10% FBS + 1% PS | 300/100 |
| MDA-MB-453 | DMEM + 10% FBS + 1% PS | 300/100 |
| MDA-MB-468 | DMEM + 10% FBS + 1% PS | 300/100 |
| Liver Cancer | | |
| Hep G2 | 87% MEM + 10% FBS + 1% NEAA + 1% NaP + 1% PS | 800/300 |
| Huh1 | DMEM + 10% FBS + 1% PS | 400/150 |
| Huh7 | DMEM + 10% FBS + 1% PS | 400/150 |
| SNU398 | 1640 + 10% FBS + 1% PS | 400/150 |
| SNU475 | 1640 + 10% FBS + 1% PS | 300/100 |
| MHCC-97H | DMEM + 10% FBS + 1% PS | 300/100 |
| Lung Cancer | | |
| A-549 | F-12K + 10% FBS + 1% PS | 300/100 |
| EBC-1 | 87% MEM + 10% FBS + 1% NEAA + 1% NaP + 1% PS | 100/50 |
| HCC827 | 88% 1640 + 10% FBS + 1% NaP + 1% Glutamax + 1% PS | 80/30 |

Results for representative compounds described herein are shown in Table 5 below.

TABLE 5

| | IC50 (μM) | | | | | |
|---|---|---|---|---|---|---|
| | 8 days | | | 12 days | | |
| Cell Lines | Ref 2 | 24a | 52a | Ref 2 | 24a | 52a |
| Breast Cancers | | | | | | |
| BT474 | 0.14 | 0.11 | 0.041 | 0.056 | 0.057 | 0.030 |
| MCF-7 | 0.037 | 0.016 | 0.025 | 0.029 | 0.026 | 0.021 |
| MDA-MB-231 | 0.70 | 0.49 | 0.17 | 0.096 | 0.075 | 0.064 |
| MDA-MB-453 | 1.22 | 0.28 | 0.14 | 0.16 | 0.19 | 0.060 |
| MDA-MB-468 | 0.044 | 0.042 | 0.022 | 0.0074 | 0.0041 | 0.0038 |
| Liver Cancers | | | | | | |
| Hep G2 | >10 | 2.87 | 3.09 | 3.26 | 0.77 | 0.97 |
| Huh1 | 1.92 | 0.44 | 0.54 | 0.085 | 0.041 | 0.075 |
| Huh7 | 0.23 | 0.28 | 0.26 | 0.073 | 0.072 | 0.092 |
| SNU398 | 0.83 | 0.54 | 0.45 | 0.41 | 0.25 | 0.12 |
| SNU475 | 0.66 | 0.21 | 0.29 | 0.86 | 0.32 | 0.35 |
| MHCC-97H | 0.089 | 0.020 | 0.023 | 0.086 | 0.029 | 0.024 |
| Lung Cancers | | | | | | |
| A-549 | 0.096 | 0.064 | 0.13 | 0.066 | 0.037 | 0.028 |
| EBC-1 | 0.062 | 0.025 | 0.028 | 0.057 | 0.030 | 0.031 |
| HCC827 | 0.34 | 0.19 | 0.16 | 0.50 | 0.11 | 0.089 |

Example 62: Pharmacokinetic Study in Mouse, Rat and Dog

Male CD-1 mice (16-24 g; 6-8 weeks; purchased from Shanghai SLAC laboratory animal CO. LTD; n=18, with 3 per time point) were treated with a single dose of compounds being tested at 2 mg/kg by intravenous tail-vein injection and 10 mg/kg by oral gavage administration, with both doses formulated in 20% N,N-dimethylacetamide in water. Animals upon PO administration were fasted overnight and fed 4 hours after dosing. Animals upon IV administration were free access to food and water. The study was performed in accordance with the guidelines and standards of the Association for Assessment and Accreditation of Laboratory Animal Care (AAALAC International) and the National Institutes of Health.

The animals were anesthetized via isoflurane at the designated time points, and approximately 110 μL of blood sample was collected via retro-orbital puncture or cardiac puncture for stagger bleeding under the anesthesia with Isoflurane inhalation into EDTA-2K tubes. The blood samples were maintained in wet ice first and centrifuged to obtain plasma (2000 g, 4° C., 5 min) within 15 minutes post sampling. Plasma samples were stored at approximately −70° C. until analysis. For plasma samples not diluted, an aliquot of 20 μL sample was added with 200 μL IS (Propranolol, 100 ng/mL) in ACN. The mixture was vortexed for 10 min and centrifuged at 5800 rpm for 10 min. An aliquot of 0.5 μL supernatant was injected for LC-MS/MS analysis. For 10-fold diluted plasma samples, an aliquot of 2 μL sample was added with 18 μL blank diluted plasma, the dilution factor was 10. The followed operation was the same as no diluted plasma samples. Standard calibration curves were constructed by analyzing a series of control plasma aliquots containing Propranolol (100 ng/mL) as an internal standard and 1.0-3,000 ng/mL testing compounds. Compound concentrations were determine with UPLC-MS/MS-33 (Triple Quad™ 6500 Plus).

Male SD rats (185-265 g; purchased from Shanghai SLAC laboratory animal CO. LTD; n=18, with 3 per compound) were treated with a single dose of compounds being tested at 2 mg/kg by intravenous tail-vein injection and 10 mg/kg by oral gavage administration, with both doses formulated in 5% DMSO+45% PEG400 in water. Animals upon PO administration were fasted overnight and fed 4 hours after dosing. Animals upon IV administration were free access to food and water. The study was performed in accordance with the guidelines and standards of the Association for Assessment and Accreditation of Laboratory Animal Care (AAALAC International) and the National Institutes of Health.

The animal is restrained manually. Approximately 150 μL whole blood/time point is collected in K2EDTA tube via tail vein. Blood sample will be put on ice and centrifuged at 2000 g for 5 min to obtain plasma sample within 15 minutes. Plasma samples were stored at approximately −70° C. until analysis. An aliquot of 20 μL sample was added with 200 μL IS (Diclofenac, 100 ng/mL) in ACN. The mixture was vortexed for 10 min and centrifuged at 5800 rpm for 10 min. An aliquot of 1 μL supernatant was injected for LC-MS/MS analysis. For 10×-diluted sample, an aliquot of 2 μL sample was added with 18 μL blank plasma. The sample preparation procedure is same with no-diluted sample. Standard calibration curves were constructed by analyzing a series of control plasma aliquots containing Diclofenac (100 ng/mL) as an internal standard and 1.0-3,000 ng/mL testing compounds. Compound concentrations were determined with UPLC-MS/MS-22 (Triple Quad™ 6500).

None naïve male beagle dogs (8-10 kg; purchased from Beijing Marshall Biotechnology Co. LTD; n=18, with 3 per compound) were treated with a single dose of compounds being tested at 2 mg/kg by intravenous tail-vein injection and 10 mg/kg by oral gavage administration, with both doses formulated in 5% DMSO+45% PEG400 in water. Animals upon PO administration were fasted overnight and fed 4 hours after dosing. Animals upon IV administration were free access to food and water. The study was performed in accordance with the guidelines and standards of the Association for Assessment and Accreditation of Laboratory Animal Care (AAALAC International) and the National Institutes of Health.

The animal was restrained manually at the designated time points, and approximately 500 μL of each blood/time point was collected via cephalic vein and put on wet ice, then centrifuged at 2000 g for 5 min (4° C.) within 15 minutes post sampling. Plasma samples were stored at approximately −70° C. until analysis. An aliquot of 20 μL sample was added with 200 μL IS (Diclofenac, 100 ng/mL) in ACN. The mixture was vortexed for 10 min and centrifuged at 5800 rpm for 10 min. An aliquot of 1 μL supernatant was injected for LC-MS/MS analysis. For 10×-diluted sample, an aliquot of 2 μL sample was added with 18 μL blank plasma. The sample preparation procedure is same with no-diluted sample. Standard calibration curves were constructed by analyzing a series of control plasma aliquots containing Diclofenac (100 ng/mL) as an internal standard and 3-3,000 ng/mL testing compounds. Compound concentrations were determined with UPLC-MS/MS-22 (Triple Quad™ 6500). Results for representative compounds described herein are shown in Tables 6a-6c.

TABLE 6a

Mouse PK Parameters of representative compounds

| | | Ref 2 | 24a | 52a |
|---|---|---|---|---|
| Mouse PK (IV) 2 mpk | $Cl_{int}$ (L/h/kg) | 2.68 | 2.14 | 3.04 |
| | $V_{ss}$ (L/kg) | 1.48 | 2.48 | 2.25 |
| Mouse PK (PO) 10 mpk | $T\frac{1}{2}$ (h) | 0.798 | 1.22 | 2.86 |
| | $T_{max}$ (h) | 2 | 0.25 | 0.25 |
| | $C_{max}$ (ng/ml) | 761 | 3576 | 3084 |
| | F (%) | 64.9 | 73.3 | 83 |
| | $AUC_{last}$ (h*ng/mL) | 2415 | 3412 | 2725 |

TABLE 6b

Rat PK Parameters of representative compounds

| | | Ref 2 | 24a | 52a |
|---|---|---|---|---|
| Rat PK (IV) 2 mpk | $Cl_{int}$ (L/h/kg) | 2.13 ± 0.237 | 1.90 ± 0.259 | 2.12 ± 0.124 |
| | $V_{ss}$ (L/kg) | 2.17 ± 0.0643 | 7.15 ± 2.86 | 5.02 ± 0.389 |
| Rat PK (PO) 10 mpk | $T\frac{1}{2}$ (h) | 1.50 ± 0.123 | 3.13 ± 0.415 | 3.02 ± 0.413 |
| | $T_{max}$ (h) | 1.67 ± 0.577 | 1.17 ± 0.764 | 1.33 ± 0.577 |
| | $C_{max}$ (ng/ml) | 364 ± 82.5 | 798 ± 247 | 563 ± 233 |
| | F (%) | 30.5 ± 13.0 | 62.0 ± 15.1 | 48.1 ± 16.1 |
| | $AUC_{last}$ (h*ng/mL) | 1403 ± 601 | 3282 ± 805 | 2264 ± 764 |

TABLE 6c

| Dog PK Parameters of representative compounds | | | | |
|---|---|---|---|---|
| | | Ref 2 | 24a | 52a |
| Dog PK (IV) 2 mpk | $Cl_{int}$ (L/h/kg) | 0.808 ± 0.164 | 0.256 ± 0.033 | 0.310 ± 0.043 |
| | $V_{ss}$ (L/kg) | 1.32 ± 0.144 | 1.807 ± 0.130 | 1.564 ± 0.041 |
| Dog PK (PO) 10 mpk | $T^{1/2}$ (h) | 3.37 ± 0.640 | 3.76 ± 0.195 | 4.81 ± 1.00 |
| | $T_{max}$ (h) | 1.67 ± 0.577 | 2.00 ± 0.00 | 1.33 ± 0.577 |
| | $C_{max}$ (ng/ml) | 3001 ± 567 | 4440 ± 680 | 5552 ± 1587 |
| | F (%) | 105 ± 25.5 | 89.8 ± 20.5 | 133 ± 38.6 |
| | $AUC_{last}$ (h*ng/mL) | 13303 ± 3279 | 35080 ± 7989 | 42112 ± 13248 |

Example 63: Mantle Cell Lymphoma (MCL) Z-138 Xenograft Efficacy Studies

All of the procedures related to animal handling, care and treatment in this study were performed according to the guidelines approved by the Institutional Animal Care and Use Committee (IACUC) of Shanghai Chempartner following the guidance of the AAALAC.

For the in vivo efficacy studies, CB-17 female SCID mice (19-21 g; 10-12 weeks) were purchased from Shanghai SLAC laboratory animal CO. LTD. Each mouse was inoculated subcutaneously at the right flank with Z-138 tumor cells ($5 \times 10^6$ cells/mouse, 50% Matrigel) in 0.2 mL of a mixture of base media and Matrigel (RPMI:Matrigel, 1:1) for tumor development. The treatments were started when the mean tumor size reached 121.55 mm³, which was 11 days after inoculation. Mice were assigned into groups using a randomized block design. Testing compounds or vehicle (5% DMSO+45% PEG400+50% $H_2O$) was administered orally BID for 21 days. Body weights were measured three times per week for the whole duration of the study. Tumor size was measured at the same schedule in two dimensions using a caliper, and the volume was expressed in cubic millimeters. Animals were euthanized 6 h after the final dose on day 21, at which time tumors were collected for analysis. Results for representative compounds described herein are shown in FIG. 1. FIG. 1 shows the tumor volume change after the treatment with compound (52a).

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A compound represented by Formula (I), or a pharmaceutically acceptable salt, ester, prodrug, complex, solvate, hydrate, or stereoisomer thereof, in any crystalline form or in amorphous form:

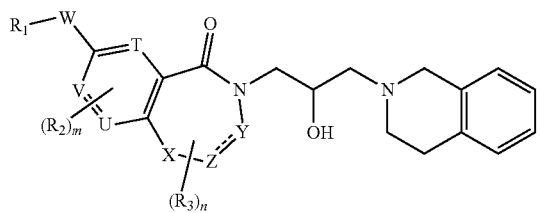

wherein $R_1$ is a non-hydrogen monovalent group; W is a direct bond or —NH—; T, U, and V are independently of each other selected from carbon and nitrogen; $R_2$ is a hydrogen or a halo; m is 1 or 2; X is a carbon, a nitrogen, or an oxygen; Y is a carbon or a nitrogen; Z is a direct bond or a carbon; $R_3$ is a hydrogen, a non-hydrogen monovalent group, an oxo group or carbonyl group (O =), a bivalent spiro ring-forming group, or a bivalent bridge-forming group; n is 1 or 2; and ====== stands for a single bond or a double bond.

2. The compound according to claim 1, wherein Formula (I) is Formula (Ia-1) or Formula (Id-1):

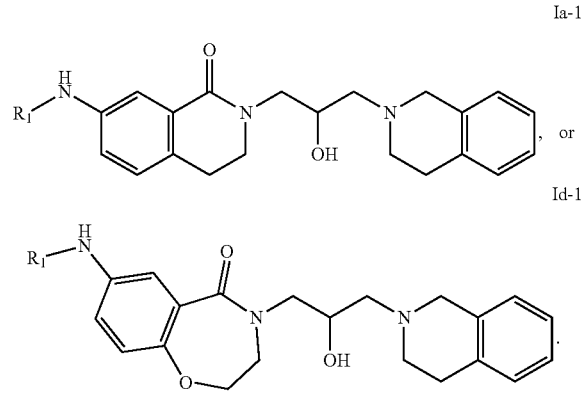

3. The compound according to claim 1, wherein Ri is piperidinyl, acetylpiperidinyl, a $C_3$-$C_{12}$ spiro-, fused-, or bridged-bicyclic group containing 0-2 hetero atoms, azaspiroheptanyl, acetylazaspiroheptanyl, azetidinyl, acetylazetidinyl, (methyl sulfonyl)azetidinyl, azabicyclooctanyl, acetylazabicyclooctanyl, azabicyclohexanyl, acetylazabicyclohexanyl, cycloalkyl, pyrrolidinyl, oxopyrrolidinyl, alkyloxopyrrolidinyl, methyloxopyrrolidinyl, methylazetidinyl, pyrazolyl, alkylpyrazolyl, alkyl-1H-pyrazolyl, methyl-oxodihydropyridinyl, methyl-oxadiazolyl, oxetanyl, (oxetanyl)-1H-pyrazolyl, pyrimidinyl, pyridazinyl, tetrahydrofuranyl, tetrahydropyranyl, or tetrahydropyranyl-pyrazolyl.

4. The compound according to claim 1, wherein $R_1$ is 1-acetylpiperidin-4-yl, 2-acetyl-2-azaspiro[3.3]heptan-6-yl, 1-acetylazetidin-3-yl, 8-acetyl-8-azabicyclo[3.2.1]octan-3-yl, 3-acetyl-3-azabicyclo[3.1.0]hexan-6-yl, cyclobutyl, 1-methyl-5-oxopyrrolidin-3-yl, 1-(methylsulfonyl)azetidin-3-yl, 1-methylazetidin-3-yl, 1-methyl-1H-pyrazol-4-yl, 1-methyl-1H-pyrazol-3-yl, 1-methyl-1H-pyrazol-5-yl, 1-methyl-2-oxo-1,2-dihydropyridin-4-yl, 5-methyl-1,3,4-oxadiazol-2-yl, oxetan-3-yl, 1-(oxetan-3-yl)-1H-pyrazol-4-yl, pyrimidin-5-yl, pyrimidin-4-yl, pyridazin-4-yl, pyridazin-3-yl, pyrazin-2-yl, tetrahydro-furan-3-yl, tetrahydro-2H-pyran-4-yl, or 1-(tetrahydro-2H-pyran-4-yl)-1H-pyrazol-4-yl.

5. The compound according to claim 1, wherein $R_2$ is H or F, and m=1.

6. The compound according to claim 1, wherein $R_3$ is H, a C1-C6 alkyl, an oxo group or carbonyl (O=), a bivalent C2-C6 spiro ring-forming group, or a bivalent C1-C4 bridge-forming group; and n=1 or 2.

7. The compound according to claim 1, which is one of the following compounds:

2-(3-(3,4-dihydroisoquinolin-2(1H)-yl)-2-hydroxypropyl)-7-(oxetan-3-ylamino)-3,4-dihydroisoquinolin-1(2H)-one (1)

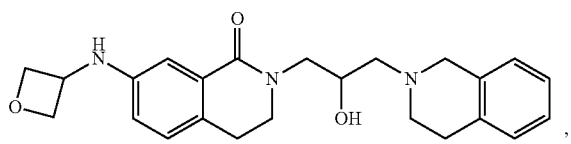

(R)-7-((1-acetylpiperidin-4-yl)amino)-4-(3-(3,4-dihydroisoquinolin-2(1H)-yl)-2-hydroxypropyl)-9-fluoro-3,4-dihydrobenzo[f][1,4]oxazepin-5(2H)-one (2a)

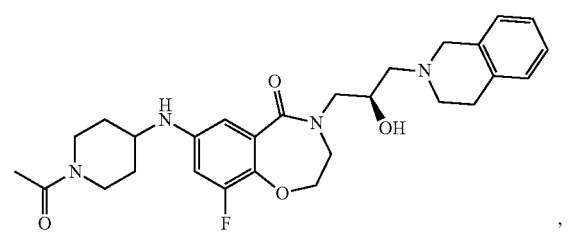

(S)-7-((1-acetylpiperidin-4-yl)amino)-4-(3-(3,4-dihydroisoquinolin-2(1H)-yl)-2-hydroxypropyl)-9-fluoro-3,4-dihydrobenzo[f][1,4]oxazepin-5(2H)-one (2b)

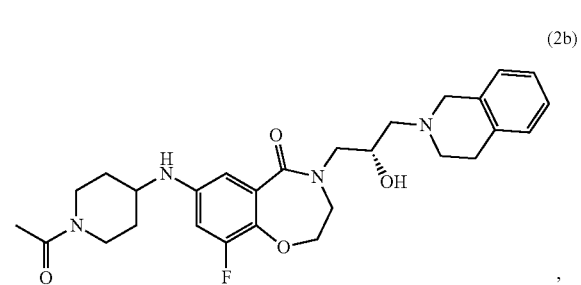 [SMILES: CC(=O)N1CCC(Nc2cc(F)c3c(c2)C(=O)N(C[C@@H](O)CN2CCc4ccccc4C2)CCO3)CC1]

3-(3-(3,4-dihydroisoquinolin-2(1H)-yl)-2-hydroxypropyl)-6-(oxetan-3-ylamino)quinazolin-4(3H)-one (3)

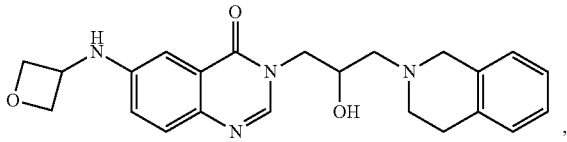

2-(3-(3,4-dihydroisoquinolin-2(1H)-yl)-2-hydroxypropyl)-7-(oxetan-3-ylamino)isoquinolin-1(2H)-one (4)

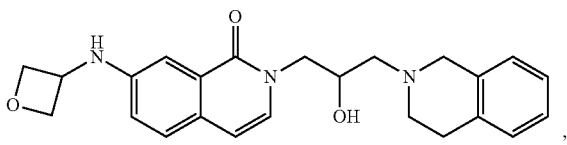

4-(3-(3,4-dihydroisoquinolin-2(1H)-yl)-2-hydroxypropyl)-7-(oxetan-3-ylamino)-3,4-dihydrobenzo[f][1,4]oxazepin-5(2H)-one (5)

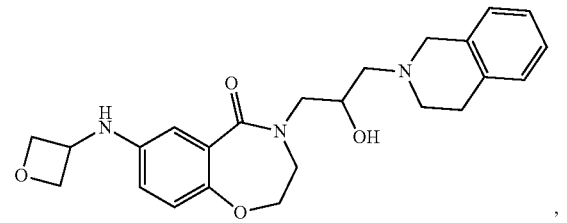

7-((1-acetylazetidin-3-yl)amino)-2-(3-(3,4-dihydroisoquinolin-2(1H)-yl)-2-hydroxypropyl)-3,4-dihydroisoquinolin-1(2H)-one (6)

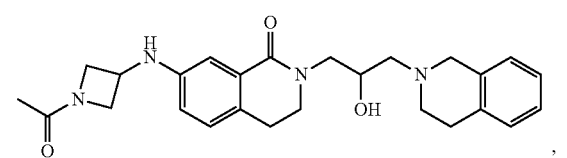

7-(cyclobutylamino)-2-(3-(3,4-dihydroisoquinolin-2(1H)-yl)-2-hydroxypropyl)-3,4-dihydroisoquinolin-1(2H)-one (7)

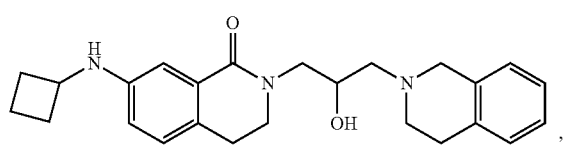

(S)-2-(3-(3,4-dihydroisoquinolin-2(1H)-yl)-2-hydroxypropyl)-7-(((1-(methylsulfonyl)azetidin-3-yl)amino)-3,4-dihydroisoquinolin-1(2H)-one (8)

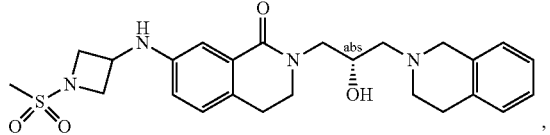

(S)-2-(3-(3,4-dihydroisoquinolin-2(1H)-yl)-2-hydroxypropyl)-7-(((1-methylazetidin-3-yl)amino)-3,4-dihydroisoquinolin-1(2H)-one (9)

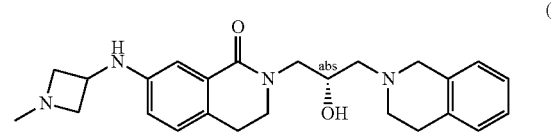

2-((S)-3-(3,4-dihydroisoquinolin-2(1H)-yl)-2-hydroxypropyl)-7-(((S)-tetrahydrofuran-3-yl)amino)-3,4-dihydroisoquinolin-1(2H)-one (10)

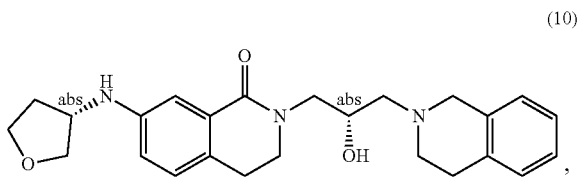 [SMILES: O=C1c2cc(N[C@H]3CCOC3)ccc2CCN1C[C@@H](O)CN1CCc2ccccc2C1]

2-((S)-3-(3,4-dihy droi soquinolin-2(1H)-yl)-2-hydroxypropyl)-7-(((R)-tetrahydrofuran-3-yl)amino)-3,4-dihy droi soquinolin-1(2H)-one (11)

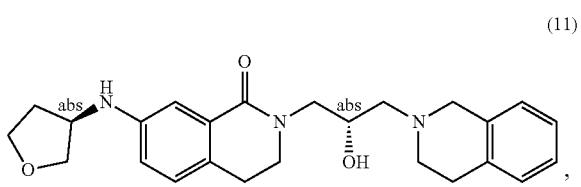 [SMILES: O=C1c2cc(N[C@@H]3CCOC3)ccc2CCN1C[C@@H](O)CN1CCc2ccccc2C1]

2-(3-(3,4-dihydroisoquinolin-2(1H)-yl)-2-hydroxypropyl)-7-(1-methyl-1H-pyrazol-4-yl)amino)-3,4-dihydroisoquinolin-1(2H)-one (12)

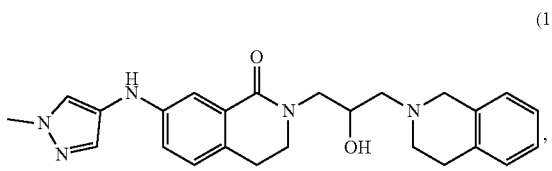

(R)-2-(3-(3,4-dihydroisoquinolin-2(1H)-yl)-2-hydroxypropyl)-7-(1-methyl-1H-pyrazol-4-yl)amino)-3,4-dihydroisoquinolin-1(2H)-one (12a)

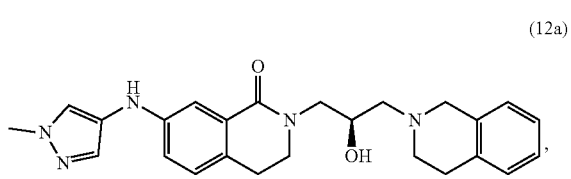 [SMILES: Cn1cc(Nc2ccc3c(c2)C(=O)N(C[C@H](O)CN2CCc4ccccc4C2)CC3)cn1]

(S)-2-(3-(3,4-dihydroisoquinolin-2(1H)-yl)-2-hydroxypropyl)-7-(1-methyl-1H-pyrazol-4-yl)amino)-3,4-dihydroisoquinolin-1(2H)-one (12b)

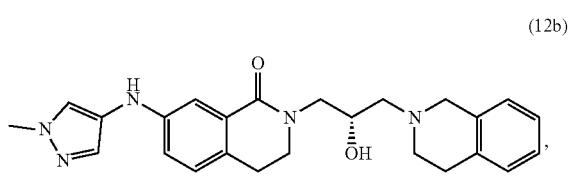 [SMILES: Cn1cc(Nc2ccc3c(c2)C(=O)N(C[C@@H](O)CN2CCc4ccccc4C2)CC3)cn1]

(S)-2-(3-(3,4-dihydroisoquinolin-2(1H)-yl)-2-hydroxypropyl)-7-(1-methyl-1H-pyrazol-4-yl)-3,4-dihydroisoquinolin-1(2H)-one (13)

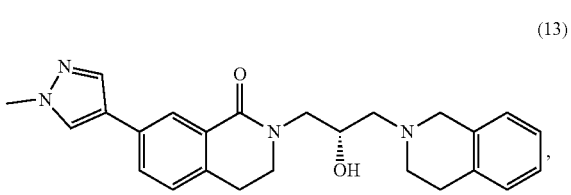 [SMILES: Cn1cc(-c2ccc3c(c2)C(=O)N(C[C@@H](O)CN2CCc4ccccc4C2)CC3)cn1]

2-(3-(3,4-dihydroisoquinolin-2(1H)-yl)-2-hydroxypropyl)-7-(pyrimidin-5-yl)-3,4-dihydroisoquinolin-1(2H)-one (14)

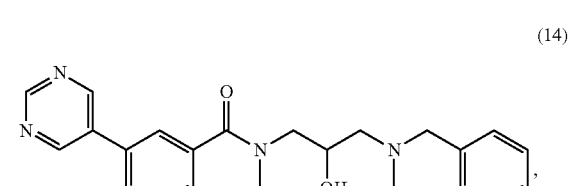

2-(3-(3,4-dihydroisoquinolin-2(1H)-yl)-2-hydroxypropyl)-4,4-dimethyl-7-(oxetan-3-ylamino)-3,4-dihydroisoquinolin-1(2H)-one (15)

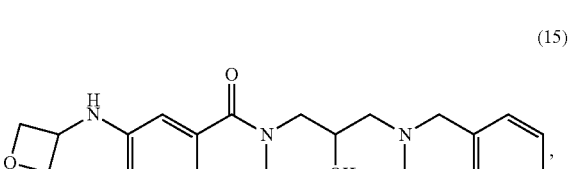

6-(3-(3,4-dihydroisoquinolin-2(1H)-yl)-2-hydroxypropyl)-3-(oxetan-3-ylamino)-7,8-dihydro-1,6-naphthyridin-5(6H)-one (16)

(16)

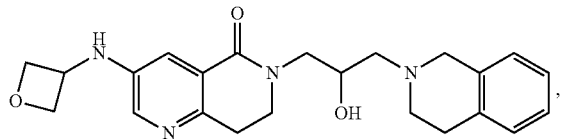

(R)-7-((1-acetylpiperidin-4-yl)amino)-4-(3-(3,4-dihydroisoquinolin-2(1H)-yl)-2-hydroxypropyl)-8-fluoro-3,4-dihydrobenzo[f][1,4]oxazepin-5(2H)-one (17a)

(17a)

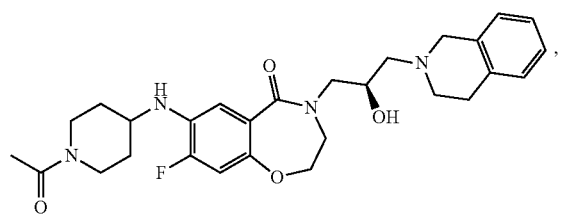

(S)-7-((1-acetylpiperidin-4-yl)amino)-4-(3-(3,4-dihydroisoquinolin-2(1H)-yl)-2-hydroxypropyl)-8-fluoro-3,4-dihydrobenzo[f][1,4]oxazepin-5(2H)-one (17b)

(17b)

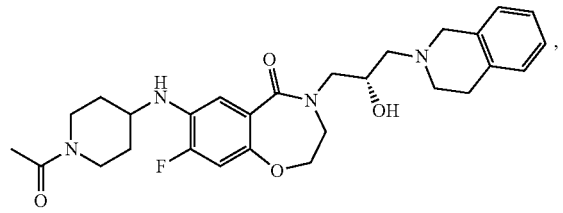

6-(3-(3,4-dihydroisoquinolin-2(1H)-yl)-2-hydroxypropyl)-3-((tetrahydro-2H-pyran-4-yl)amino)-7,8-dihydro-1,6-naphthyridin-5(6H)-one (18)

(18)

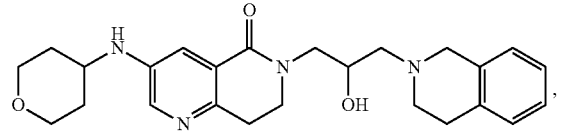

3-((1-acetylpiperidin-4-yl)amino)-6-(3-(3,4-dihydroisoquinolin-2(1H)-yl)-2-hydroxypropyl)-7,8-dihydro-1,6-naphthyridin-5(6H)-one (19)

(19)

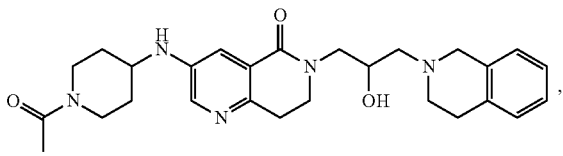

6-(3-(3,4-dihydroisoquinolin-2(1H)-yl)-2-hydroxypropyl)-3-(1-methyl-1H-pyrazol-4-yl)amino)-7,8-dihydro-1,6-naphthyridin-5(6H)-one (20)

(20)

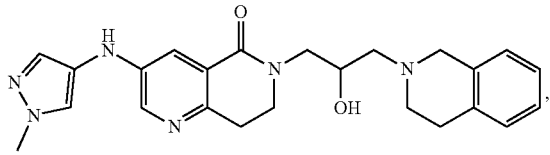

2-(3-(3,4-dihydroisoquinolin-2(1H)-yl)-2-hydroxypropyl)-3-methyl-7-(oxetan-3-ylamino)-3,4-dihydroisoquinolin-1(2H)-one (21)

(21)

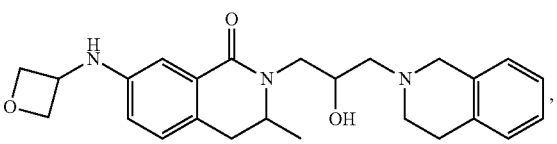

2-(3-(3,4-dihydroisoquinolin-2(1H)-yl)-2-hydroxypropyl)-74(1-(oxetan-3-yl)-1H-pyrazol-4-yl) amino)-3,4-dihydroisoquinolin-1(2H)-one (22)

(22)

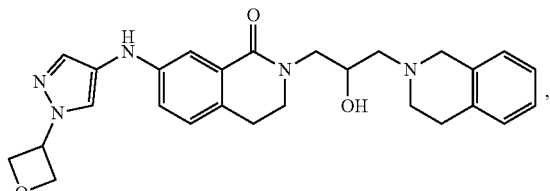

2-(3-(3,4-dihydroisoquinolin-2(1H)-yl)-2-hydroxypropyl)-7-(1-methyl-1H-pyrazol-3-yl)amino)-3,4-dihydroisoquinolin-1(2H)-one (23)

(23)

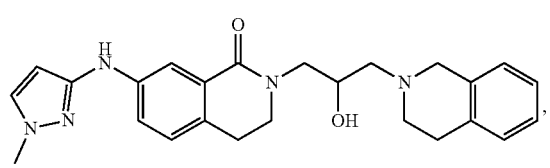

7-((1-acetylpiperidin-4-yl)amino)-2-(3-(3,4-dihydroiso-quinolin-2(1H)-yl)-2-hydroxy propyl)-3,4-dihydroiso-quinolin-1(2H)-one (24)

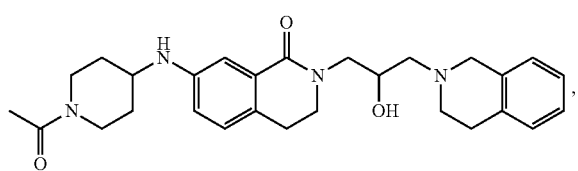

(R)-7-((1-acetylpiperidin-4-yl)amino)-2-(3-(3,4-dihy-droisoquinolin-2(1H)-yl)-2-hydroxypropyl)-3,4-dihy-droisoquinolin-1(2H)-one (24a)

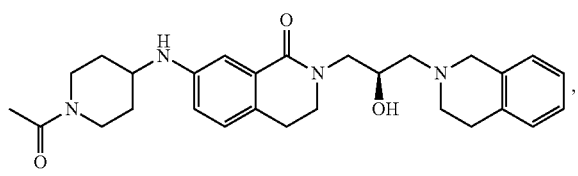

(S)-7-((1-acetylpiperidin-4-yl)amino)-2-(3-(3,4-dihy-droisoquinolin-2(1H)-yl)-2-hydroxypropyl)-3,4-dihy-droisoquinolin-1(2H)-one (24b)

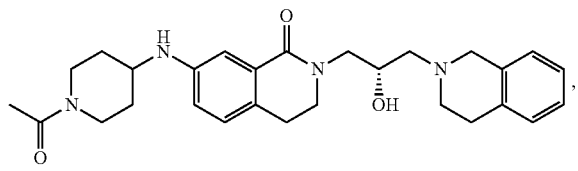

2-(3-(3,4-dihydroisoquinolin-2(1H)-yl)-2-hydroxypro-pyl)-7-((1-(tetrahydro-2H-pyran-4-yl)-1H-pyrazol-4-yl)amino)-3,4-dihydroisoquinolin-1(2H)-one (25)

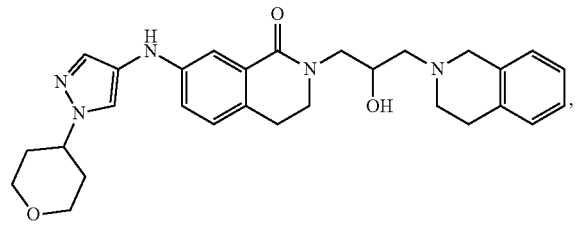

6-chloro-2-(3-(3,4-dihydroisoquinolin-2(1H)-yl)-2-hy-droxypropyl)-7-((1-methyl-1H-pyrazol-4-yl)amino)-3,4-dihydroisoquinolin-1(2H)-one (26),

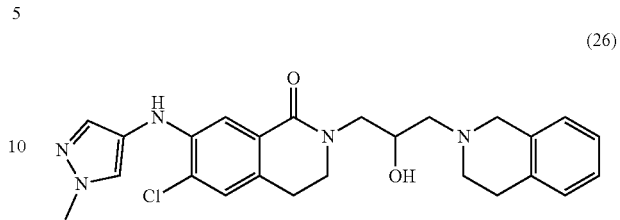

2-(3-(3,4-dihydroisoquinolin-2(1H)-yl)-2-hydroxypro-pyl)-74(1-methyl-2-oxo-1,2-dihydropyridin-4-yl)amino)-3,4-dihydroisoquinolin-1(2H)-one (27)

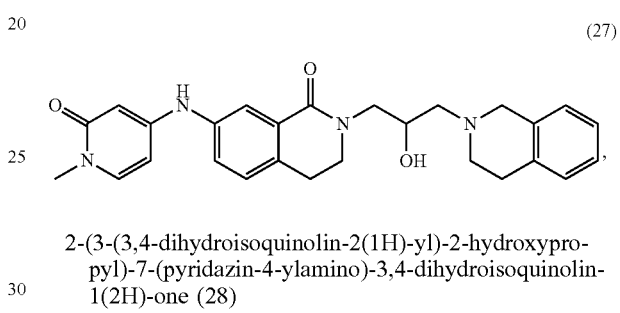

2-(3-(3,4-dihydroisoquinolin-2(1H)-yl)-2-hydroxypro-pyl)-7-(pyridazin-4-ylamino)-3,4-dihydroisoquinolin-1(2H)-one (28)

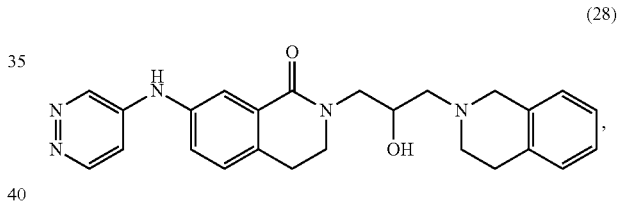

(R)-2-(3-(3,4-dihydroisoquinolin-2(1H)-yl)-2-hydroxy-propyl)-7-(pyridazin-4-ylamino)-3,4-dihydroisoquino-lin-1(2H)-one (28a)

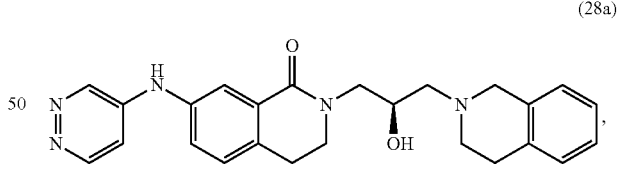

(S)-2-(3-(3,4-dihydroisoquinolin-2(1H)-yl)-2-hydroxy-propyl)-7-(pyridazin-4-ylamino)-3,4-dihydroisoquino-lin-1(2H)-one (28b)

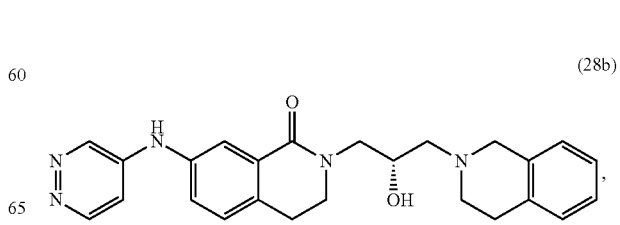

4-(3-(3,4-dihydroisoquinolin-2(1H)-yl)-2-hydroxypropyl)-7-(1-methyl-1H-pyrazol-4-yl)amino)-3,4-dihydrobenzo[f][1,4]oxazepin-5(2H)-one (29)

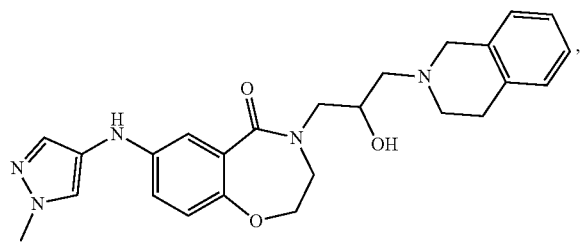
(29)

(R)-4-(3-(3,4-dihydroisoquinolin-2(1H)-yl)-2-hydroxypropyl)-7-(1-methyl-1H-pyrazol-4-yl)amino)-3,4-dihydrobenzo[f][1,4]oxazepin-5(2H)-one (29a)

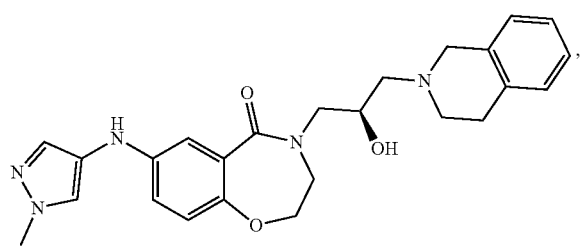
(29a)

(S)-4-(3-(3,4-dihydroisoquinolin-2(1H)-yl)-2-hydroxypropyl)-7-(1-methyl-1H-pyrazol-4-yl)amino)-3,4-dihydrobenzo[f][1,4]oxazepin-5(2H)-one (29b)

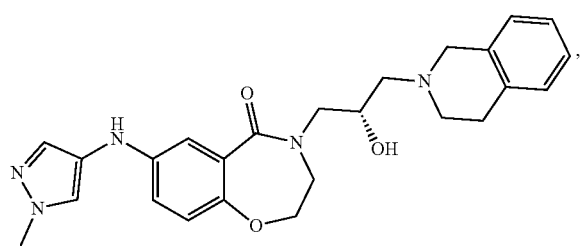
(29b)

4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (30)

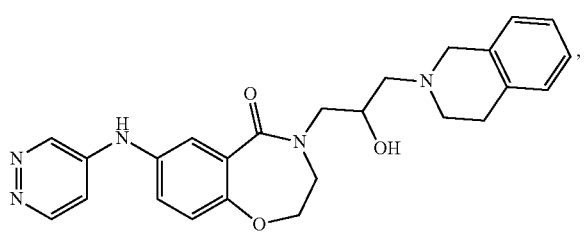
(30)

(R)-4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (30a)

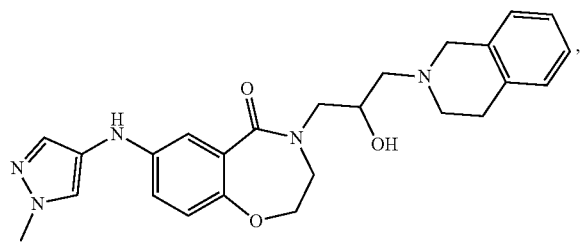
(30a)

(S)-4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (30b)

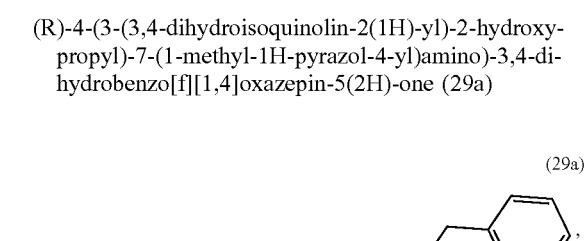
(30b)

3-(3-(3,4-dihydroisoquinolin-2(1H)-yl)-2-hydroxypropyl)-6-(pyridazin-4-ylamino)quinazolin-4(3H)-one (31)

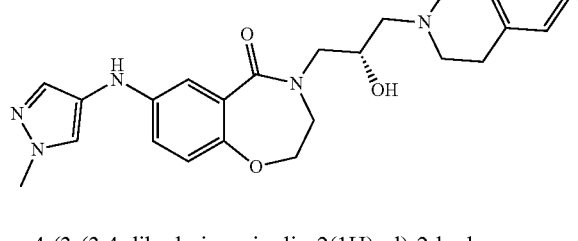
(31)

2-(3-(3,4-dihydroisoquinolin-2(1H)-yl)-2-hydroxypropyl)-7-(pyridazin-4-ylamino)isoquinolin-1(2H)-one (32)

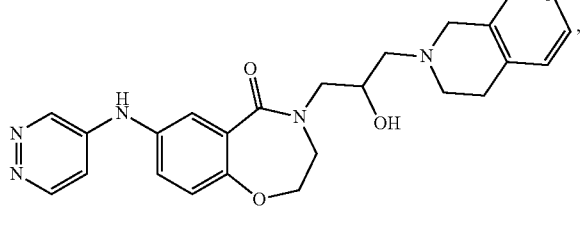
(32)

2-(3-(3,4-dihydroisoquinolin-2(1H)-yl)-2-hydroxypropyl)-7-(pyridazin-4-ylamino)phthalazin-1(2H)-one (33)

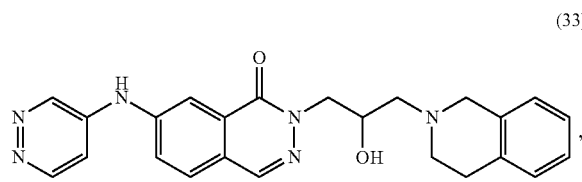 [SMILES: O=c1c2cc(Nc3ccnnc3)ccc2cnn1CC(O)CN1CCc2ccccc2C1]
(33)

2-(3-(3,4-dihydroisoquinolin-2(1H)-yl)-2-hydroxypropyl)-4,4-dimethyl-7-(pyridazin-4-ylamino)-3,4-dihydroisoquinolin-1(2H)-one (34)

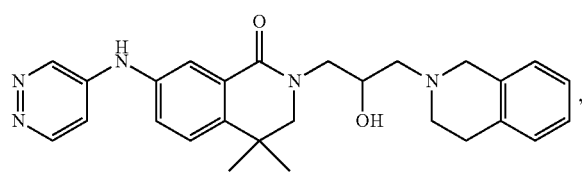
(34)

2'-(3-(3,4-dihydroisoquinolin-2(1H)-yl)-2-hydroxypropyl)-7'-(pyridazin-4-ylamino)-2',3'-dihydro-1'H-spiro[cyclopropane-1,4'-isoquinolin]-1'-one (35)

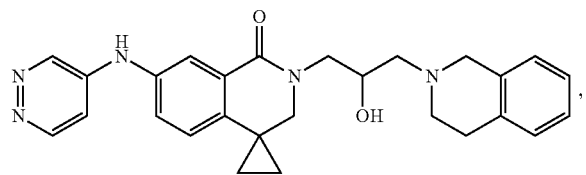
(35)

(R)-4-(3-(3,4-dihydroisoquinolin-2(1H)-yl)-2-hydroxypropyl)-7-(pyrimidin-5-ylamino)-3,4-dihydrobenzo[f][1,4]oxazepin-5(2H)-one (36)

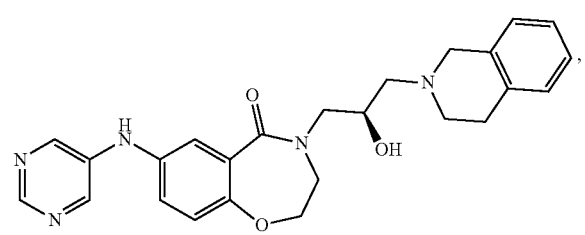
(36)

(R)-4-(3-(3,4-dihydroisoquinolin-2(1H)-yl)-2-hydroxypropyl)-7-(pyrimidin-4-ylamino)-3,4-dihydrobenzo[f][1,4]oxazepin-5(2H)-one (37)

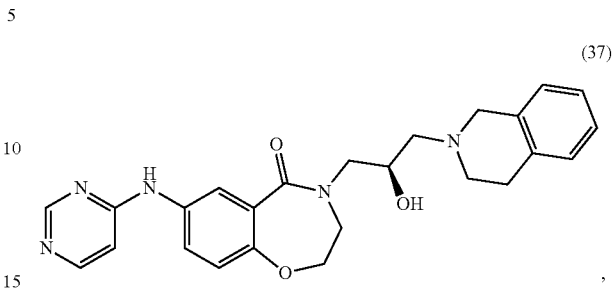
(37)

(R)-4-(3-(3,4-dihydroisoquinolin-2(1H)-yl)-2-hydroxypropyl)-7-(pyrazin-2-ylamino)-3,4-dihydrobenzo[f][1,4]oxazepin-5(2H)-one (38)

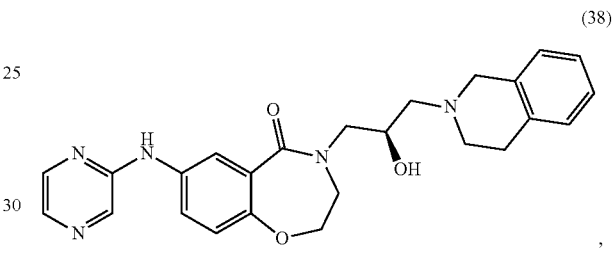
(38)

(R)-4-(3-(3,4-dihydroisoquinolin-2(1H)-yl)-2-hydroxypropyl)-7-(pyridazin-3-ylamino)-3,4-dihydrobenzo[f][1,4]oxazepin-5(2H)-one (39)

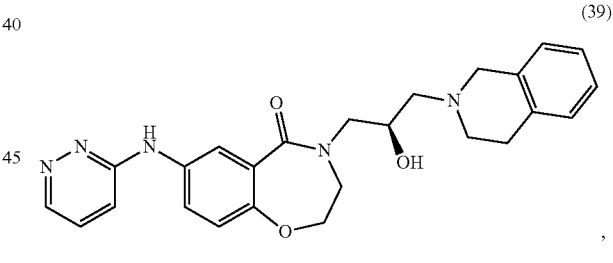
(39)

(R)-4-(3-(3,4-dihydroisoquinolin-2(1H)-yl)-2-hydroxypropyl)-7-((1-methyl-2-oxo-1,2-dihydropyridin-4-yl)amino)-3,4-dihydrobenzo[f][1,4]oxazepin-5(2H)-one (40)

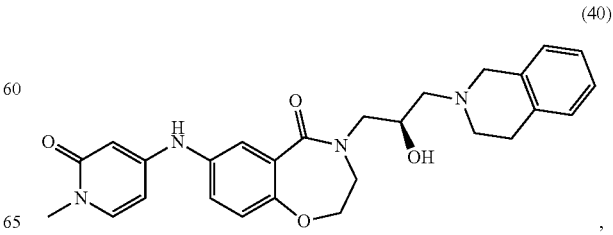
(40)

(R)-4-(3-(3,4-dihydroisoquinolin-2(1H)-yl)-2-hydroxy-
  propyl)-7-((1-methyl-1H-pyrazol-5-yl)amino)-3,4-di-
  hydrobenzo[f][1,4]oxazepin-5(2H)-one (41)

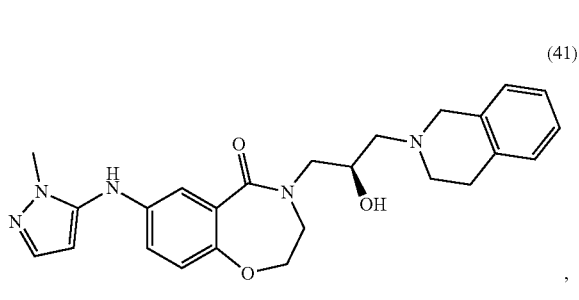 [SMILES: Cn1nccc1Nc1ccc2c(c1)C(=O)N(C[C@H](O)CN1CCc3ccccc3C1)CCO2]

(41)

(R)-4-(3-(3,4-dihydroisoquinolin-2(1H)-yl)-2-hydroxy-
  propyl)-7-((5-methyl-1,3,4-oxadiazol-2-yl)amino)-3,4-
  dihydrobenzo[f][1,4]oxazepin-5(2H)-one (42)

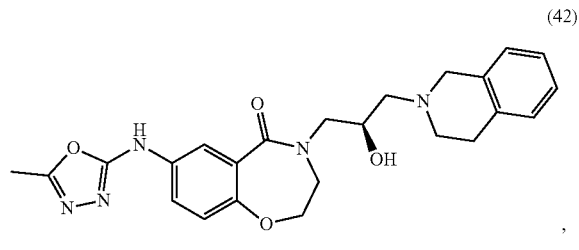 [SMILES: Cc1nnc(Nc2ccc3c(c2)C(=O)N(C[C@H](O)CN2CCc4ccccc4C2)CCO3)o1]

(42)

4-((R)-3-(3,4-dihydroi soquinolin-2(1H)-yl)-2-hydroxy-
  propyl)-7-((l-methyl-5-oxopyrroli din-3-yl)amino)-3,
  4-dihydrobenzo[f][1,4]oxazepin-5(2H)-one (43)

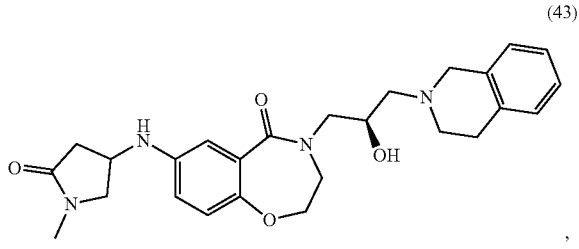 [SMILES: CN1CC(Nc2ccc3c(c2)C(=O)N(C[C@H](O)CN2CCc4ccccc4C2)CCO3)CC1=O]

(43)

4-(3-(3,4-dihydroisoquinolin-2(1H)-yl)-2-hydroxypro-
  pyl)-1-methyl-7-(pyridazin-4-ylamino)-3,4-dihydro-
  1H-benzo[e][1,4]diazepine-2,5-dione (44)

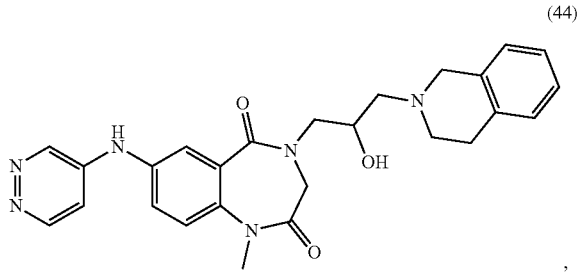 [SMILES: CN1C(=O)CN(CC(O)CN2CCc3ccccc3C2)C(=O)c2cc(Nc3ccnnc3)ccc21]

(44)

4-(3-(3,4-dihydroisoquinolin-2(1H)-yl)-2-hydroxypro-
  pyl)-1-methyl-7-(pyridazin-4-ylamino)-1,2,s3,4-tetra-
  hydro-5H-benzo[e][1,4]diazepin-5-one (45)

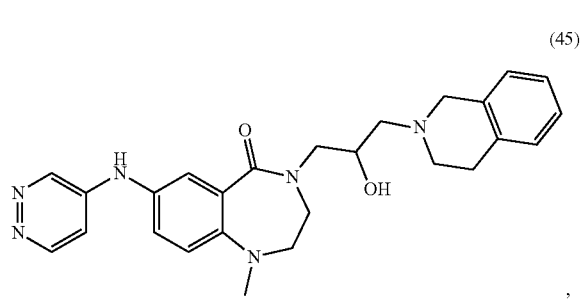 [SMILES: CN1CCN(CC(O)CN2CCc3ccccc3C2)C(=O)c2cc(Nc3ccnnc3)ccc21]

(45)

7-((1-acetylpiperidin-4-yl)amino)-4-(3-(3,4-dihydroiso-
  quinolin-2(1H)-yl)-2-hydroxy propyl)-6-fluoro-3,4-di-
  hydrobenzo[f][1,4]oxazepin-5(2H)-one (46)

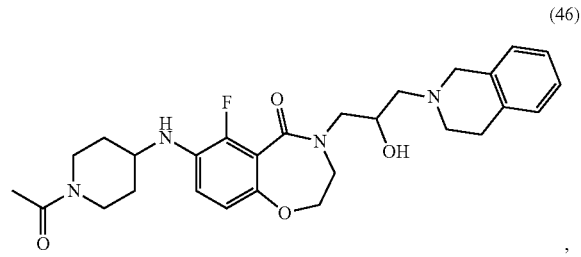 [SMILES: CC(=O)N1CCC(Nc2ccc3c(c2F)C(=O)N(CC(O)CN2CCc4ccccc4C2)CCO3)CC1]

(46)

(R)-7-((1-acetylpiperidin-4-yl)amino)-4-(3-(3,4-dihy-
  droisoquinolin-2(1H)-yl)-2-hydroxypropyl)-6-fluoro-
  3,4-dihydrobenzo[f][1,4]oxazepin-5(2H)-one (46a)

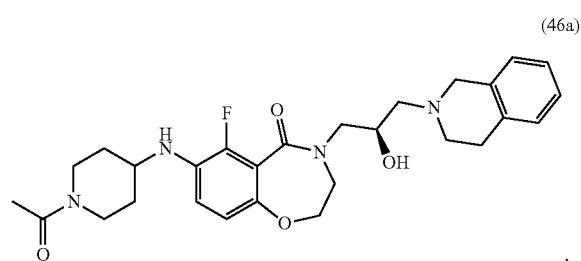 [SMILES: CC(=O)N1CCC(Nc2ccc3c(c2F)C(=O)N(C[C@H](O)CN2CCc4ccccc4C2)CCO3)CC1]

(46a)

(S)-7-((1-acetylpiperidin-4-yl)amino)-4-(3-(3,4-dihy-
  droisoquinolin-2(1H)-yl)-2-hydroxypropyl)-6-fluoro-
  3,4-dihydrobenzo[f][1,4]oxazepin-5(2H)-one (46b)

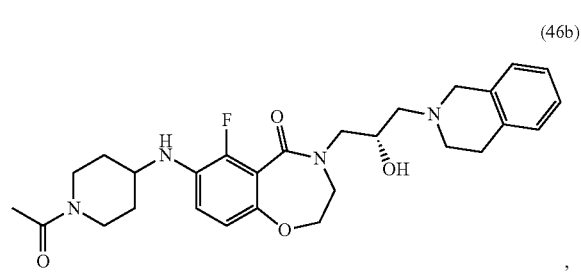 [SMILES: CC(=O)N1CCC(Nc2ccc3c(c2F)C(=O)N(C[C@@H](O)CN2CCc4ccccc4C2)CCO3)CC1]

(46b)

4-(3-(3,4-dihydroisoquinolin-2(1H)-yl)-2-hydroxypropyl)-7-(pyridazin-4-ylamino)-3,4-dihydropyrido[3,2-f][1,4]oxazepin-5(2H)-one (47)

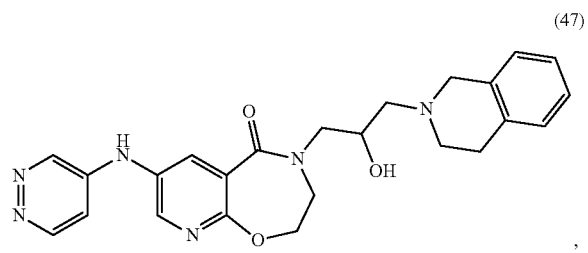 [SMILES: O=C1c2cc(Nc3ccnnc3)cnc2OCCN1CC(O)CN1CCc2ccccc2C1]

(47)

4-(3-(3,4-dihydroisoquinolin-2(1H)-yl)-2-hydroxypropyl)-7-(pyridazin-4-ylamino)-3,4-dihydropyrido[4,3-f][1,4]oxazepin-5(2H)-one (48)

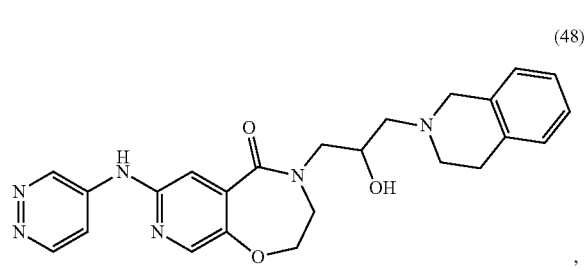 [SMILES: O=C1c2cc(Nc3ccnnc3)ncc2OCCN1CC(O)CN1CCc2ccccc2C1]

(48)

4-(3-(3,4-dihydroisoquinolin-2(1H)-yl)-2-hydroxypropyl)-7-(pyridazin-4-ylamino)-3,4-dihydropyrido[2,3-f][1,4]oxazepin-5(2H)-one (49)

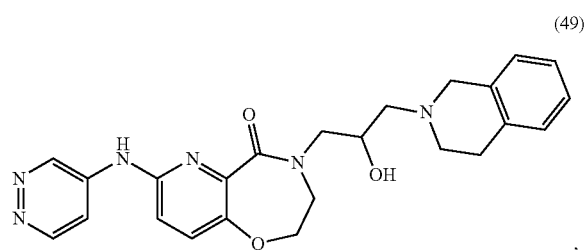 [SMILES: O=C1c2nc(Nc3ccnnc3)ccc2OCCN1CC(O)CN1CCc2ccccc2C1]

(49)

4-(3-(3,4-dihydroisoquinolin-2(1H)-yl)-2-hydroxypropyl)-8-fluoro-7-(pyridazin-4-ylamino)-3,4-dihydrobenzo[f][1,4]oxazepin-5(2H)-one (50)

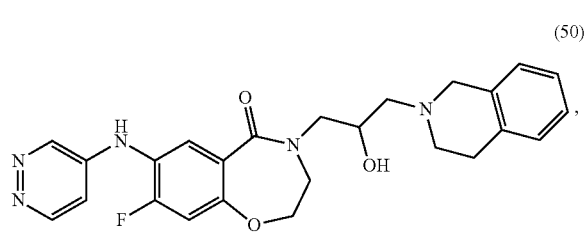 [SMILES: O=C1c2cc(Nc3ccnnc3)c(F)cc2OCCN1CC(O)CN1CCc2ccccc2C1]

(50)

4-(3-(3,4-dihydroisoquinolin-2(1H)-yl)-2-hydroxypropyl)-9-fluoro-7-(pyridazin-4-ylamino)-3,4-dihydrobenzo[f][1,4]oxazepin-5(2H)-one (51)

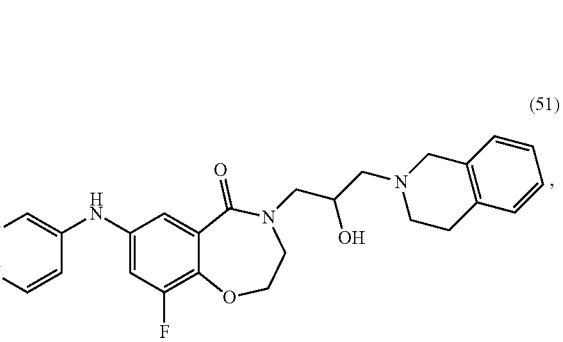

(51)

7-((1-acetylpiperidin-4-yl)amino)-4-(3-(3,4-dihydroisoquinolin-2(1H)-yl)-2-hydroxy propyl)-3,4-dihydrobenzo[f][1,4]oxazepin-5(2H)-one (52)

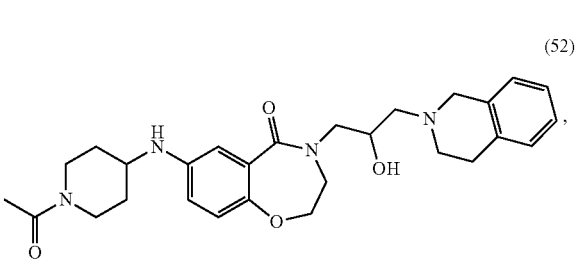

(52)

(R)-7-((1-acetylpiperidin-4-yl)amino)-4-(3-(3,4-dihydroisoquinolin-2(1H)-yl)-2-hydroxypropyl)-3,4-dihydrobenzo[f][1,4]oxazepin-5(2H)-one (52a)

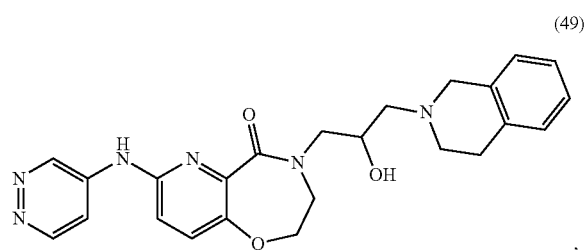 [SMILES: O=C1c2nc(Nc3ccnnc3)ccc2OCCN1CC(O)CN1CCc2ccccc2C1]

(52a)

(S)-7-((1-acetylpiperidin-4-yl)amino)-4-(3-(3,4-dihydroisoquinolin-2(1H)-yl)-2-hydroxypropyl)-3,4-dihydrobenzo[f][1,4]oxazepin-5(2H)-one (52b)

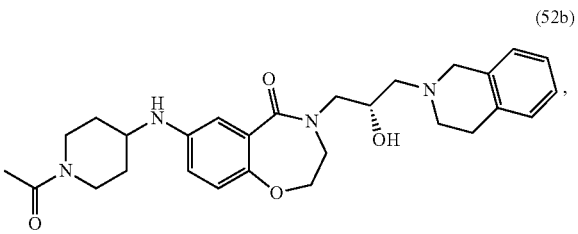 [SMILES: CC(=O)N1CCC(Nc2ccc3c(c2)C(=O)N(CC(O)CN2CCc4ccccc4C2)CCO3)CC1]

(52b)

7'-((1-acetylpiperidin-4-yl)amino)-2'-(3-(3,4-dihydroiso-
quinolin-2(1H)-yl)-2-hydroxy propyl)-2',3'-dihydro-
1'H-spiro[cyclopropane-1,4'-isoquinolin]-1'-one (53)

(53)

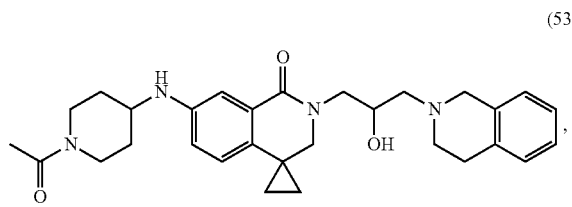

(R)-7'-((l-acetylpiperidin-4-yl)amino)-2'-(3-(3,4-dihy-
droisoquinolin-2(1H)-yl)-2-hydroxypropyl)-2',3'-di-
hydro-1'H-spiro[cyclopropane-1,4'-isoquinolin]-1'-one
(53a)

(53a)

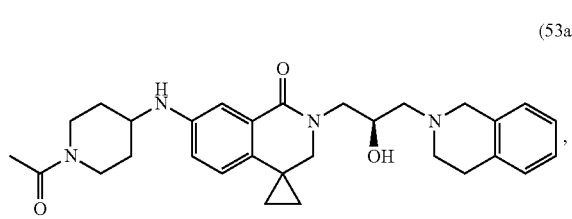

(S)-7'-(1-acetylpiperidin-4-yl)amino)-T-(3-(3,4-dihy-
droisoquinolin-2(1H)-yl)-2-hydroxypropyl)-2',3'-di-
hydro-1'H-spiro[cyclopropane-1,4'-isoquinolin]-1'-one
(53b)

(53b)

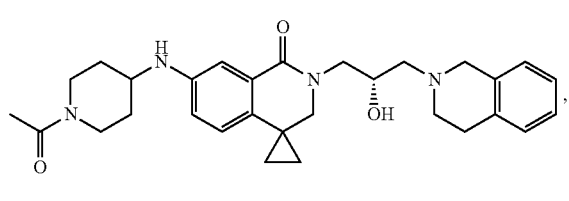

74(2-acetyl-2-azaspiro[3.3]heptan-6-yl)amino)-4-(3-(3,4-
dihydroisoquinolin-2(1H)-yl)-2-hydroxypropyl)-3,4-
dihydrobenzo[f][1,4]oxazepin-5(2H)-one (54)

(54)

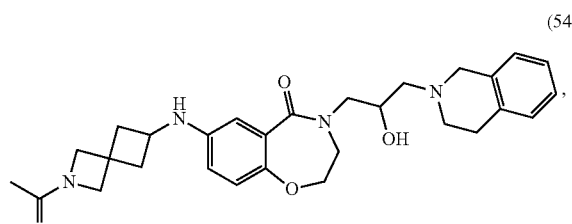

7-((8-acetyl-8-azabicyclo[3.2.1]octan-3-yl)amino)-4-(3-
(3,4-dihydroisoquinolin-2(1H)-yl)-2-hydroxypropyl)-
3,4-dihydrobenzo[f][1,4]oxazepin-5(2H)-one (55)

(55)

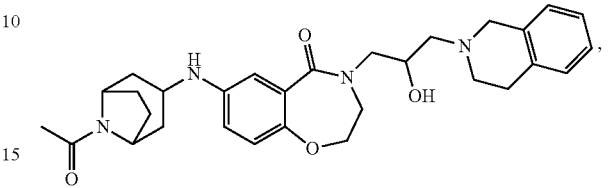

743-acetyl-3-azabicyclo[3.1.0]hexan-6-yl)amino)-4-(3-
(3,4-dihydroisoquinolin-2(1H)-yl)-2-hydroxypropyl)-
3,4-dihydrobenzo[f][1,4]oxazepin-5(2H)-one (56)

(56)

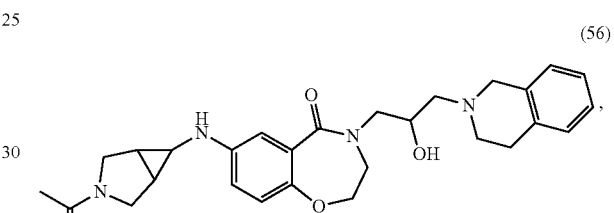

8-((1-acetylpiperidin-4-yl)amino)-2-(3-(3,4-dihydroiso-
quinolin-2(1H)-yl)-2-hydroxypropyl)-2,3,4,5-tetra-
hydro-lH-3,5-methanobenzo[c]azepin-1-one (57)

(57)

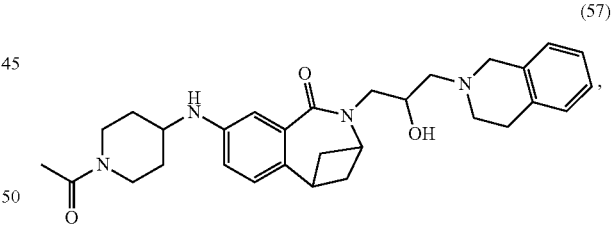

(R)-8-((1-acetylpiperidin-4-yl)amino)-2-(3-(3,4-dihy-
droisoquinolin-2(1H)-yl)-2-hydroxypropyl)-2,3,4,5-
tetrahydro-lH-3,5-methanobenzo[c]azepin-1-one (57a)

(57a)

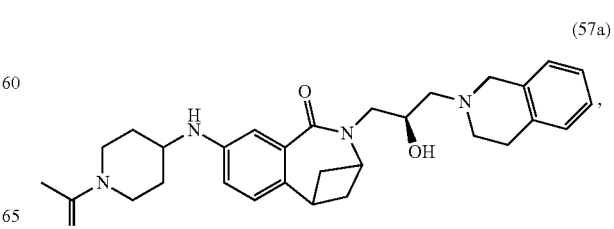

or
(S)-8-((1-acetylpiperidin-4-yl)amino)-2-(3-(3,4-dihydroisoquinolin-2(1H)-yl)-2-hydroxypropyl)-2,3,4,5-tetrahydro-1H-3,5-methanobenzo[c]azepin-1-one (57b)

(57b)

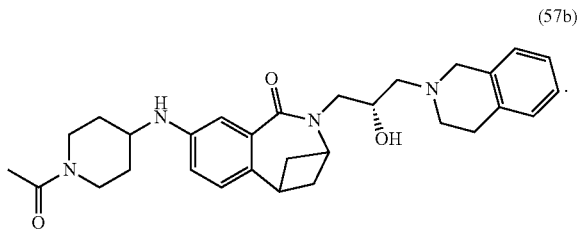 [SMILES: CC(=O)N1CCC(Nc2ccc3c(c2)C(=O)N(C[C@@H](O)CN2CCc4ccccc4C2)C2CC3C2)CC1]

8. The compound according to claim 1, wherein R₁ is 1-acetylpiperidin-4-yl, 1-methyl-1H-pyrazol-4-yl, or pyridazin-4-yl; W is —NH—; T, U, and V are all carbon atoms; R₂ is H or F; m is 1; X is a carbon atom or an oxygen atom; Y is a carbon atom; Z is a direct bond or a carbon atom; R₃ is H; and ===== stands for a single bond.

9. The compound according to claim 1, which is one of the following compounds:
(R)-7-(1-acetylpiperidin-4-yl)amino)-4-(3-(3,4-dihydroisoquinolin-2(1H)-yl)-2-hydroxypropyl)-9-fluoro-3,4-dihydrobenzo[f][1,4]oxazepin-5(2H)-one (2a)

(2a)

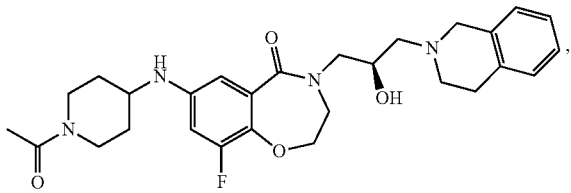

(R)-2-(3-(3,4-dihydroisoquinolin-2(1H)-yl)-2-hydroxypropyl)-7-(1-methyl-1H-pyrazol-4-yl)amino)-3,4-dihydroisoquinolin-1(2H)-one (12a)

(12a)

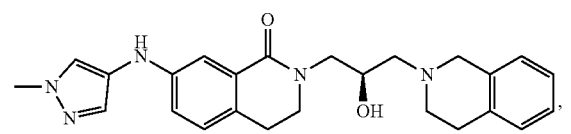

(R)-7-((1-acetylpiperidin-4-yl)amino)-2-(3-(3,4-dihydroisoquinolin-2(1H)-yl)-2-hydroxypropyl)-3,4-dihydroisoquinolin-1(2H)-one (24a)

(24a)

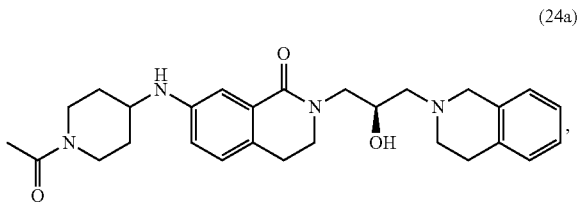 [SMILES: CC(=O)N1CCC(Nc2ccc3c(c2)C(=O)N(C[C@H](O)CN2CCc4ccccc4C2)CC3)CC1]

(R)-2-(3-(3,4-dihydroisoquinolin-2(1H)-yl)-2-hydroxypropyl)-7-(pyridazin-4-ylamino)-3,4-dihydroisoquinolin-1(2H)-one (28a)

(28a)

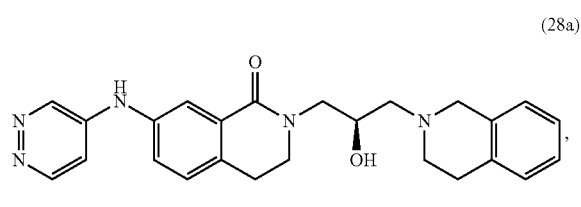 [SMILES: O=C1c2cc(Nc3ccnnc3)ccc2CCN1C[C@H](O)CN1CCc2ccccc2C1]

(R)-4-(3-(3,4-dihydroisoquinolin-2(1H)-yl)-2-hydroxypropyl)-7-(1-methyl-1H-pyrazol-4-yl)amino)-3,4-dihydrobenzo[f][1,4]oxazepin-5(2H)-one (29a)

(29a)

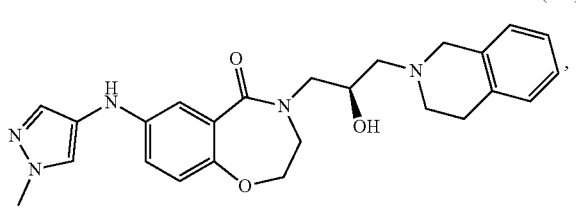

(R)-4-(3-(3,4-dihydroisoquinolin-2(1H)-yl)-2-hydroxypropyl)-7-(pyridazin-4-ylamino)-3,4-dihydrobenzo[f][1,4]oxazepin-5(2H)-one (30a)

(30a)

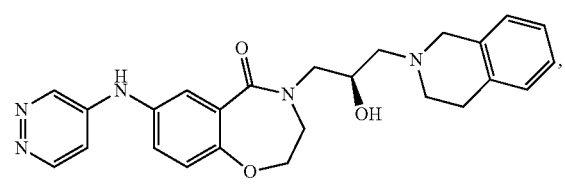

(R)-7-((1-acetylpiperidin-4-yl)amino)-4-(3-(3,4-dihydroisoquinolin-2(1H)-yl)-2-hydroxypropyl)-3,4-dihydrobenzo[f][1,4]oxazepin-5(2H)-one (52a)

(52a)

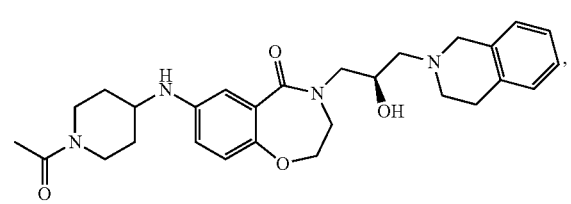

and (S)-7-((1-acetylpiperidin-4-yl)amino)-4-(3-(3,4-dihydroisoquinolin-2(1H)-yl)-2-hydroxypropyl)-3,4-dihydrobenzo[f][1,4]oxazepin-5(2H)-one (52b)

(52b)

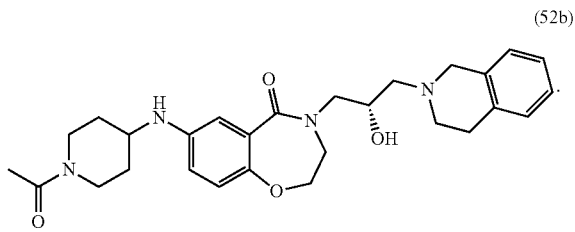 [SMILES: CC(=O)N1CCC(Nc2ccc3c(c2)C(=O)N(C[C@@H](O)CN2CCc4ccccc4C2)CCO3)CC1]

10. The compound according to claim 1, which is
(R)-7-((1-acetylpiperidin-4-yl)amino)-2-(3-(3,4-dihydroisoquinolin-2(1H)-yl)-2-hydroxypropyl)-3,4-dihydroisoquinolin-1(2H)-one (24a)

(24a)

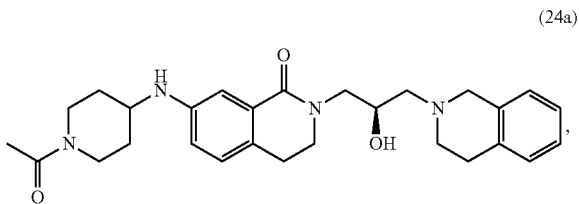 [SMILES: CC(=O)N1CCC(Nc2ccc3c(c2)C(=O)N(C[C@H](O)CN2CCc4ccccc4C2)CC3)CC1]

or (R)-7-((1-acetylpiperidin-4-yl)amino)-4-(3-(3,4-dihydroisoquinolin-2(1H)-yl)-2-hydroxypropyl)-3,4-dihydrobenzo[f] [1,4] oxazepin-5(2H)-one (52a)

(52a)

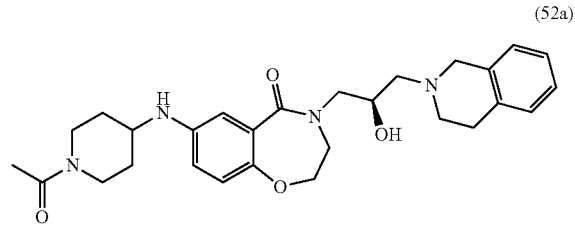 [SMILES: CC(=O)N1CCC(Nc2ccc3c(c2)C(=O)N(C[C@H](O)CN2CCc4ccccc4C2)CCO3)CC1]

11. A pharmaceutical composition comprising a therapeutically effective amount of the compound according to claim 1, or a pharmaceutically acceptable salt, ester, prodrug, complex, solvate, stereoisomer, or hydrate thereof, in any crystalline form or in amorphous form, and a pharmaceutically acceptable carrier or excipient.

12. A kit or packaged pharmaceutical comprising a therapeutically effective amount of the compound according to claim 1, or a pharmaceutically acceptable salt, ester, prodrug, complex, solvate, stereoisomer, or hydrate thereof, in any crystalline form or in amorphous form, and instructions for use thereof.

13. A method of inhibiting a protein arginine methyltransferase 5 (PRMT5) enzyme, comprising: contacting the PRMT5 enzyme with an effective amount of a compound of claim 1, or a pharmaceutically acceptable salt, ester, prodrug, complex, solvate, stereoisomer, or hydrate thereof, in any crystalline form or in amorphous form.

14. A method of altering gene expression or altering transcription comprising contacting a cell in vitro or in a subject with an effective amount of a compound of claim 1, or a pharmaceutically acceptable salt, ester, prodrug, complex, solvate, stereoisomer, or hydrate thereof, in any crystalline form or in amorphous form.

15. A method of treating a disorder or disease mediated by PRMT5 or associated with aberrant PRMT5 activity, comprising administering to a subject in need thereof a therapeutically effective amount of a compound of claim 1, or a pharmaceutically acceptable salt, ester, prodrug, complex, solvate, stereoisomer, or hydrate thereof, in any crystalline form or in amorphous form; or a pharmaceutical composition thereof.

16. The method according to claim 15, wherein the disorder or disease is a proliferative disorder, a metabolic disorder, a blood disorder, an autoimmune disease, or an inflammatory disease.

17. The method according to claim 15, wherein the disorder or disease is breast cancer, lung cancer, pancreatic cancer, prostate cancer, colon cancer, ovarian cancer, skin cancer, testicular cancer, uterine cancer, cervical cancer, esophageal cancer, bladder cancer, gastric cancer, liver cancer, epidermoid cancer, brain cancer, hematopoietic cancer, acute myeloid leukemia (AML), acute lymphocytic leukemia, chronic myeloid leukemia, hairy cell leukemia, myelodysplasia, myeloproliferative disorders, acute myelogenous leukemia (AML), chronic myelogenous leukemia(CML), mastocytosis, chronic lymphocytic leukemia (CLL), multiple myeloma (MM), myelodysplastic syndrome (MDS), beta-thalassemia, sickle cell disease (SCD), lymphoma, medulloblastoma, rectum adenocarcinoma, colon adenocarcinoma, adenoid cystic carcinoma, lung adenocarcinoma, head and neck squamous cell carcinoma, hepatocellular carcinoma, renal cell carcinoma, oligodendroglioma, ovarian clear cell carcinoma, ovarian serous cystadenocarcinoma, melanoma, or any combination thereof.

18. The method according to claim 15, wherein the disorder or disease comprises lymphoma representable by cell lines Raji, SU-DHL4, and Z138; or glioma representable by cell lines U87MG, U251 and T98G.

19. The method according to claim 15, wherein the disorder or disease is pancreas cancer representable by cell lines IMIMPC2, MIA PaCa2, Aspc1, A6L, SKPC1 and Panc-1.

20. The method according to claim 15, wherein the disorder or disease is breast cancer representable by cell lines such as 600MPE, AU565, BT-20, BT-474, BT-483, BT-549, Evsa-T, Hs578T, MCF-7, MDA-MB-231, MDA-MB-453, MDA-MB-468, SkBr3, and T-47D; liver cancer representable by cell lines such as Hep G2, Huhl, Huh7, SNU398, SNU475, and MHCC-97H; or lung cancer representable by cell lines such as A 549, EBC-1, and HCC827.

* * * * *